(12) United States Patent
Stern et al.

(10) Patent No.: US 7,258,857 B2
(45) Date of Patent: *Aug. 21, 2007

(54) RAGE-RELATED METHODS FOR TREATING INFLAMMATION

(75) Inventors: David M. Stern, Cincinnati, OH (US); Kevan Herold, Scarsdale, NY (US); Shi Du Yan, Tenafly, NJ (US); Ann Marie Schmidt, Franklin Lakes, NJ (US); Ira Lamster, Wyckoff, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 120 days.

This patent is subject to a terminal disclaimer.

(21) Appl. No.: 09/872,185

(22) Filed: Jun. 1, 2001

(65) Prior Publication Data

US 2002/0122799 A1 Sep. 5, 2002

Related U.S. Application Data

(63) Continuation-in-part of application No. PCT/US99/23303, filed on Oct. 6, 1999, which is a continuation-in-part of application No. 09/263,312, filed on Mar. 5, 1999, now Pat. No. 6,555,340, which is a continuation-in-part of application No. 09/167,705, filed on Oct. 6, 1998, now Pat. No. 7,081,241, and a continuation-in-part of application No. 08/948,131, filed on Oct. 9, 1997, now Pat. No. 6,555,651, and a continuation-in-part of application No. 08/755,235, filed on Nov. 22, 1996, now Pat. No. 6,790,443.

(51) Int. Cl.
*A61K 39/395* (2006.01)
*C07K 16/28* (2006.01)

(52) U.S. Cl. ............... 424/130.1; 424/133.1; 424/134.1; 424/143.1; 514/825

(58) Field of Classification Search ............... 514/2, 514/8, 12, 824, 855, 921, 826, 816; 424/130.1, 424/139.1, 142.1, 143.1
See application file for complete search history.

(56) References Cited

U.S. PATENT DOCUMENTS

| 5,864,018 | A | * | 1/1999 | Morser et al. | 530/387.1 |
| 5,998,408 | A | * | 12/1999 | Baker et al. | 514/224.2 |
| 6,555,340 | B1 | | 4/2003 | Schmidt et al. | |
| 7,081,241 | B1 | | 7/2006 | Schmidt et al. | |
| 2001/0053357 | A1 | | 12/2001 | Stern et al. | |
| 2003/0059423 | A1 | | 3/2003 | Stern et al. | |

FOREIGN PATENT DOCUMENTS

WO WO 00/20621 4/2000

OTHER PUBLICATIONS

Ritthaler et al. (1995), Expression of Receptors for Advance Glycation End Products in Peripheral Occlusive Vascular Disease, Am.J. Path. vol. 146, No. 3, pp. 668-694.*
Hofmann et al. RAGE Mediates a Novel Proinflammatory Axis: A Central Cell Surface Receptor for S100/Calgranulin Polypeptide (1999), Cell, vol. 97, pp. 889-901.*
Liotta et al. Cancer: Checkpoint for invasion (2000), Nature, vol. 405, pp. 287-288.*
Baynes. J. (1991). Role of oxidative stress in development of complications in diabetes. Diabetes 40:405-412. (Exhibit 1).
Behl. C., et al. (1994). Hydrogen Peroxide Mediates Amyloid β Protein Toxicity Cell 77, 817-827. (Exhibit 2).
Vlassara. H., et al. (1994). Pathogenic effects of advanced glycosylation: biochemical. biologic, and clinical implications for diabetes and aging. Lab. Invest. 70: 138-151. (Exhibit 3).
Schmidt. A.M., SD Yan. and D. Stern.(1995). The Dark Side of Glucose (News and Views). Nature Medicine 1:1002-1004. (Exhibit 4).
Schmidt, A.M., Vianna.M., Gerlach. M., Brett. J., Ryan. J., Kao. J., Esposito. C., Hegarty. H., Hurley. W., Clauss. M., Wang. F., Pan. Y.C., Tsang. T.C. and Stern. D. (1992). Isolation and characterization of binding proteins for advanced glycosylation endproducts from lung tissue which are present on the endothelial cell surface. J.Biol. Chem. 267,14987-14997.(Exhibit 5).
Brett, J, et al., (1993). Survey of the distribution of a newly-characterized receptor for AGEs in tissues. *Am. J. Pathol.* 143:1699-1712. (Exhibit 6).
Hori O., J. Brett. T. Slattery, R. Cao. J.Zhang. J. Chen, M. Nagashima, D. Nitecki, J. Morser, D. Stern. A.M. Schmidt.(1995). The Receptor for Advanced Glycation Endproducts (RAGE) is a cellular binding site for amphoterin: mediation of neurite outgrowth and co-expression of RAGE and amphoterin in the developing nervous system. J.Biol. Chem. 270:25752-25761. (Exhibit 7).
Schmidt, A-M. et al. (1994). Cellular Receptors for Advanced Glycation Endproducts. *Arterioscler. Thromb.*, 14:1521-1528. (Exhibit 8).
Schmidt. A-M. et al. (1994). Receptor for advanced glycation endproducts (AGEs) has a central role in vessel wall interactions and gene activation in response to circulating AGE proteins. *Proc. Natl. Acad. Sci. (USA)*. 91:8807-8811. (Exhibit 9).
Sell. D., and Monnier, V. (1989). Structure elucidation of a senescene cross-link from human extracellular matrix: implication of pentoses in the aging process.J.Biol. Chem. 10 264. 21597-21602. (Exhibit 10).

(Continued)

*Primary Examiner*—Christine J. Saoud
*Assistant Examiner*—Jegatheesan Seharaseyon
(74) *Attorney, Agent, or Firm*—John P. White; Cooper & Dunham LLP

(57) ABSTRACT

The present invention provides a method for treating inflammation in a subject which comprises administering to the subject soluble receptor for advanced glycation endproduct (sRAGE) in an amount effective to inhibit binding of advanced glycation endproducts (AGEs) to RAGE thereby treating inflammation in the subject. The present invention also provides for a method for treating inflammation in a subject which comprises administering to the subject an agent in an amount effective to inhibit the interaction between receptor for advanced glycation endproduct (RAGE) and its ligand thereby treating inflammation in the subject.

11 Claims, 32 Drawing Sheets

OTHER PUBLICATIONS

Giardino, I. et al. (1994). Nonenzymatic glycosylation in Vitro and in bovine endothelial cells after basic fibroblast growth factor activity. J. Clin. Invest. 94:110-117. (Exhibit 11).

Park. I.., et al. (1997). A murine model of accelerated diabetic atherosclerosis: suppression by soluble receptor for advanced glycation endproducts. Circulation Supplement. Abstract 3079, (Exhibit 12).

Wautier, J.-I.., et al. (1996). Interaction of diabetic erythrocytes bearing advanced glycation endproducts with the endothelial receptor AGE induces generation of reactive oxygen intermediates and cellular dysfunction. Circulation Supplement 94(8):4139. (Enxhibit 13).

Wu J. Rogers L. Stern D. Schmidt AM and Chiu DTW.(1997). The soluble receptor for Advanced Glycation Endproducts (sRAGE) ameliorates impaired wound healing in diabetic mice. Plastic Surgery Research Council. Abstract #77, p. 43. (Exhibit 14).

Schmidt, A-M. et al. (1994). Cellular receptors for advanced glycation end products. *Arterioscler. Thromb.*, 14:1521-1528. t. 92:2155-2168. (Exhibit 15).

U.S. Appl. No. 60/469,428, filed May 9, 2003, Schmidt et al.

U.S. Appl. No. 10/840,927, filed May 7, 2004, Schmidt et al.

\* cited by examiner

Figure 9

ATGACTAAGCTGGAGGACCACCTGGAGGAATCATCAACATCTTC
CACCAGTACTCCGTTCGGGTGGGGCATTTCGACACCCTCAACAAG
CGTGAGCTGAAGCAGCTGATCACAAAGGAACTTCCCAAAACCCT
CCAGAACACCAAAGACCAACCTACCATTGACAAAATATTCCAAGA
CCTGGATGCCGATAAAGACGGAGCCGTCAGCTTTGAGGAATTCGT
AGTCCTGGTGTCCAGGGTGCTGAAAACAGCCCACATAGATATCCA
CAAAGAGTAGGTTTCCAGCAATGTTCCCAAGAAGACTTACCCTTCT
CCTCCCTGAGGCTGCTCCCCGAGGAGAGAGAATTATAAACGTAC
TTTGGCAAATTCTTAGCAAAAAAAAAAAAAAAA

FIGURE 11D

|  | Lane | 1 | 2 | 3 | 4 | 5 | 6 | 7 | 8 | 9 | 10 | 11 | 12 | 13 | 14 | 15 | |
|---|---|---|---|---|---|---|---|---|---|---|---|---|---|---|---|---|---|
|  |  |  |  |  |  |  | mock | | | | | wild-type | | | | | mutation |
|  |  |  |  |  |  |  |  |  |  |  |  |  |  |  |  |  | p44 MAPK<br>p42 MAPK |
| BSA |  | + | - | - | - | - | + | - | - | - | - | + | - | - | - | - |
| EN-RAGE |  | - | + | + | + | + | - | + | + | + | + | - | + | + | + | + |
| s-RAGE |  | - | - | + | - | - | - | - | + | - | - | - | - | + | - | - |
| α-RAGE IgG |  | - | - | - | + | - | - | - | - | + | - | - | - | - | + | - |
| α-N.I. IgG |  | - | - | - | - | + | - | - | - | - | + | - | - | - | - | + |

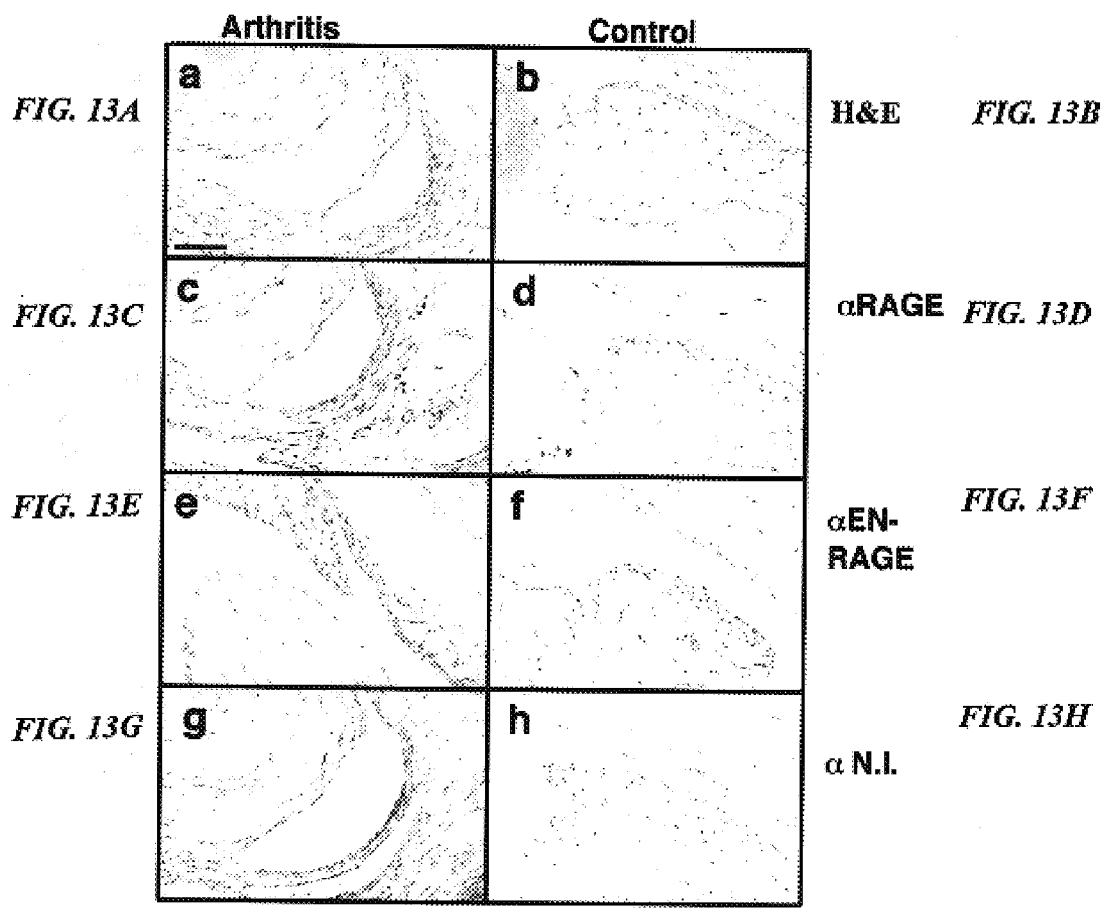

-20 kDa

FIGURE 19A
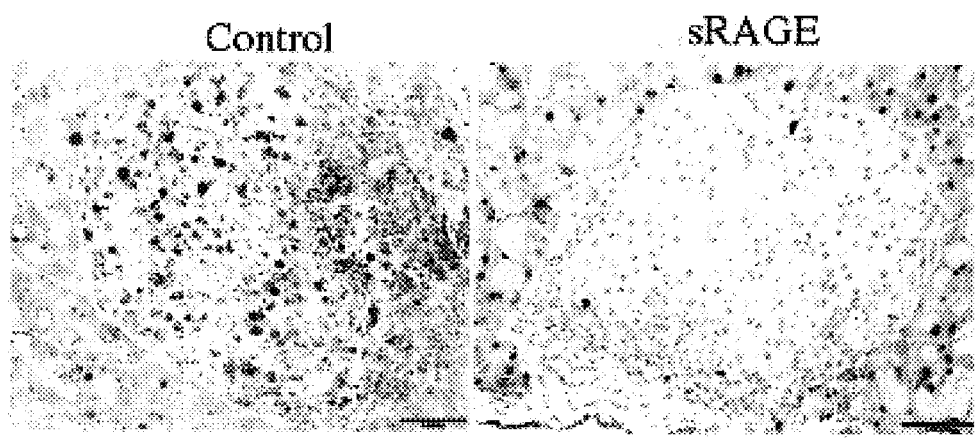
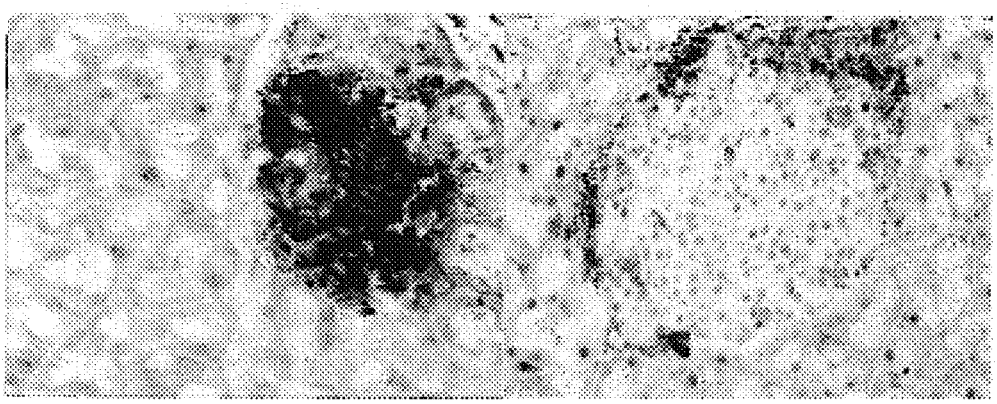
FIGURE 19B

SEQUENCE LISTING

<160> NUMBER OF SEQ ID NOS: 16

<210> SEQ ID NO 1
<211> LENGTH: 112
<212> TYPE: PRT
<213> ORGANISM: Human

<400> SEQUENCE: 1

```
Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110
```

<210> SEQ ID NO 2
<211> LENGTH: 332
<212> TYPE: PRT
<213> ORGANISM: Human

<400> SEQUENCE: 2

```
Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
            115                 120                 125

Pro Ala Gly Thr Leu Ser Trp His Leu Asp Gly Lys Pro Leu Val Pro
        130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175
```

```
Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
            195                 200                 205

Glu Pro Val Pro Leu Glu Glu Val Gln Leu Val Val Glu Pro Glu Gly
            210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
            245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
            275                 280                 285

Gln Glu Ser Arg Ala Val Ser Ile Ser Ile Ile Glu Pro Gly Glu Glu
            290                 295                 300

Gly Pro Thr Ala Gly Ser Val Gly Gly Ser Gly Leu Gly Thr Leu Ala
305                 310                 315                 320

Leu Ala Leu Gly Ile Leu Gly Gly Leu Gly Thr Ala
            325                 330

<210> SEQ ID NO 3
<211> LENGTH: 30
<212> TYPE: PRT
<213> ORGANISM: Human

<400> SEQUENCE: 3

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys
            20                  25                  30

<210> SEQ ID NO 4
<211> LENGTH: 30
<212> TYPE: PRT
<213> ORGANISM: Murine

<400> SEQUENCE: 4

Gly Gln Asn Ile Thr Ala Arg Ile Gly Glu Pro Leu Val Leu Ser Cys
1               5                   10                  15

Lys Gly Ala Pro Lys Lys Pro Pro Gln Gln Leu Glu Trp Lys
            20                  25                  30

<210> SEQ ID NO 5
<211> LENGTH: 30
<212> TYPE: PRT
<213> ORGANISM: Rat

<400> SEQUENCE: 5

Gly Gln Asn Ile Thr Ala Arg Ile Gly Glu Pro Leu Met Leu Ser Cys
1               5                   10                  15

Lys Ala Ala Pro Lys Lys Pro Thr Gln Lys Leu Glu Trp Lys
            20                  25                  30

<210> SEQ ID NO 6
<211> LENGTH: 30
<212> TYPE: PRT
<213> ORGANISM: bovine

<400> SEQUENCE: 6
```

```
Asp Gln Asn Ile Thr Ala Arg Ile Gly Lys Pro Leu Val Leu Asn Cys
1               5                   10                  15

Lys Gly Ala Pro Lys Lys Pro Pro Gln Gln Leu Glu Trp Lys
            20              25                  30

<210> SEQ ID NO 7
<211> LENGTH: 30
<212> TYPE: PRT
<213> ORGANISM: Human

<400> SEQUENCE: 7

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys
            20              25                  30

<210> SEQ ID NO 8
<211> LENGTH: 10
<212> TYPE: PRT
<213> ORGANISM: Human

<400> SEQUENCE: 8

Ala Gln Asn Ile Thr Ala Arg Ile Gly Glu
1               5                   10

<210> SEQ ID NO 9
<211> LENGTH: 50
<212> TYPE: PRT
<213> ORGANISM: Bovine
<220> FEATURE:
<221> NAME/KEY: MISC_FEATURE
<222> LOCATION: (47)..(47)
<223> OTHER INFORMATION: Where Xaa = unknown

<400> SEQUENCE: 9

Thr Lys Leu Glu Asp His Leu Glu Gly Ile Ile Asn Ile Gly His Gln
1               5                   10                  15

Tyr Ser Val Arg Val Gly His Phe Asp Thr Leu Asn Lys Tyr Glu Leu
            20              25                  30

Lys Gln Leu Gly Thr Lys Glu Leu Pro Lys Thr Leu Gln Asn Xaa Lys
        35                  40                  45
    Asp Gln
        50

<210> SEQ ID NO 10
<211> LENGTH: 18
<212> TYPE: PRT
<213> ORGANISM: Bovine

<400> SEQUENCE: 10

Asp Gly Ala Val Ser Phe Glu Glu Phe Val Val Leu Val Ser Arg Val
1               5                   10                  15

Leu Lys

<210> SEQ ID NO 11
<211> LENGTH: 90
<212> TYPE: PRT
<213> ORGANISM: Bovine

<400> SEQUENCE: 11

Thr Lys Leu Glu Asp His Leu Glu Gly Ile Ile Asn Ile Phe His Gln
1               5                   10                  15
```

```
Tyr Ser Val Arg Val Gly His Phe Asp Thr Leu Asn Lys Arg Glu Leu
        20                  25                  30

Lys Gln Leu Ile Thr Lys Glu Leu Pro Lys Thr Leu Gln Asn Thr Lys
        35                  40                  45

Asp Gln Pro Thr Ile Asp Lys Ile Phe Gln Asp Leu Asp Ala Asp Lys
    50                  55                  60

Asp Gly Ala Val Ser Phe Glu Glu Phe Val Val Leu Val Ser Arg Val
65                  70                  75                  80

Leu Lys Thr Ala His Ile Asp Ile His Lys
                85                  90

<210> SEQ ID NO 12
<211> LENGTH: 90
<212> TYPE: PRT
<213> ORGANISM: Bovine

<400> SEQUENCE: 12

Thr Lys Leu Glu Asp His Leu Glu Gly Ile Ile Asn Ile Phe His Gln
1               5                   10                  15

Tyr Ser Val Arg Val Gly His Phe Asp Thr Leu Asn Lys Arg Glu Leu
        20                  25                  30

Lys Gln Leu Ile Thr Lys Glu Leu Pro Lys Thr Leu Gln Asn Thr Lys
        35                  40                  45

Asp Gln Pro Thr Ile Asp Lys Ile Phe Gln Asp Leu Asp Ala Asp Lys
    50                  55                  60

Asp Gly Ala Val Ser Phe Glu Glu Phe Val Val Leu Val Ser Arg Val
65                  70                  75                  80

Leu Lys Thr Ala His Ile Asp Ile His Lys
                85                  90

<210> SEQ ID NO 13
<211> LENGTH: 21
<212> TYPE: DNA
<213> ORGANISM: Human

<400> SEQUENCE: 13
gtaagcgggg ctcctgttgc a                                         21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Antisense
      Primer

<400> SEQUENCE: 14
ggccaaggct ggggttgaag g                                         21

<210> SEQ ID NO 15
<211> LENGTH: 9
<212> TYPE: PRT
<213> ORGANISM: Human
<220> FEATURE:
<221> NAME/KEY: MISC_FEATURE
<222> LOCATION: (1)..(9)
<223> OTHER INFORMATION: Peptide Conserved Across Mammals

<400> SEQUENCE: 15

Ala Ser Gln Arg Lys Pro Ser Gln Arg
1               5
```

```
<210> SEQ ID NO 16
<211> LENGTH: 395
<212> TYPE: DNA
<213> ORGANISM: Bovine

<400> SEQUENCE: 16
atgactaagc tggaggacca cctggaggga atcatcaaca tcttccacca gtactccgtt      60
cgggtggggc atttcgacac cctcaacaag cgtgagctga agcagctgat cacaaaggga     120
acttcccaaa accctccaga acaccaaaga ccaacctacc attgacaaaa tattccaaga     180
cctggatgcc gataaagacg gagccgtcag ctttgaggaa ttcgtagtcc tggtgtccag     240
ggtgctgaaa acagcccaca tagatatcca caaagagtag gtttccagca atgttcccaa     300
gaagacttac ccttctcctc cctgaggctg ctccccgagg gagagagaat tataaacgta     360
ctttggcaaa ttcttagcaa aaaaaaaaaa aaaaa                                395
```

RAGE-RELATED METHODS FOR TREATING INFLAMMATION

This application is a continuation-in-part of U.S. Ser. No. 08/755,235, filed Nov. 22, 1996, now U.S. Pat. No. 6,790,443, issued Sep. 14, 2004, and U.S. Ser. No. 08/948,131, filed Oct. 9, 1997, now U.S. Pat. No. 6,555,651, issued April 29, 2003, and PCT International Application No. PCT/US99/23303, filed Oct. 6, 1999, which is a continuation-in-part of U.S. Ser. No. 09/263,312, filed Mar. 5, 1999, now U.S. Pat. No. 6,555,340, issued Apr. 29, 2003 which is a continuation-in-part of U.S. Ser. No. 09/167,705, filed Oct. 6, 1998, now U.S. Pat. No. 7,081,241, issued Jul. 25, 2006, the contents of all of which are hereby incorporated by reference into this application.

The invention disclosed herein was made with Government support under Grant Nos. HL21006 and AG00603 from the National Institutes of Health, U.S. Department of Health and Human Services. Accordingly, the U.S. Government has certain rights in this invention.

BACKGROUND OF THE INVENTION

Throughout this application, various publications are referenced by author and date. Full citations for these publications may be found listed alphabetically at the end of each section of the Experimental Details section of the application. The disclosures of these publications in their entireties are hereby incorporated by reference into this application in order to more fully describe the state of the art as known to those skilled therein.

SUMMARY OF THE INVENTION

The present invention provides a method for treating inflammation in a subject which comprises administering to the subject soluble receptor for advanced glycation endproduct (sRAGE) in an amount effective to inhibit binding of advanced glycation endproducts (AGEs) to RAGE thereby treating inflammation in the subject.

BRIEF DESCRIPTION OF THE FIGURES

Wound Healing

FIG. 3A) and non-diabetic mice (db+/m+; FIG. 3B) were excised, fixed and sections stained with affinity-purified anti-AGE IgG. Magnification: 200×.

Periodontal Disease

Figure 4:
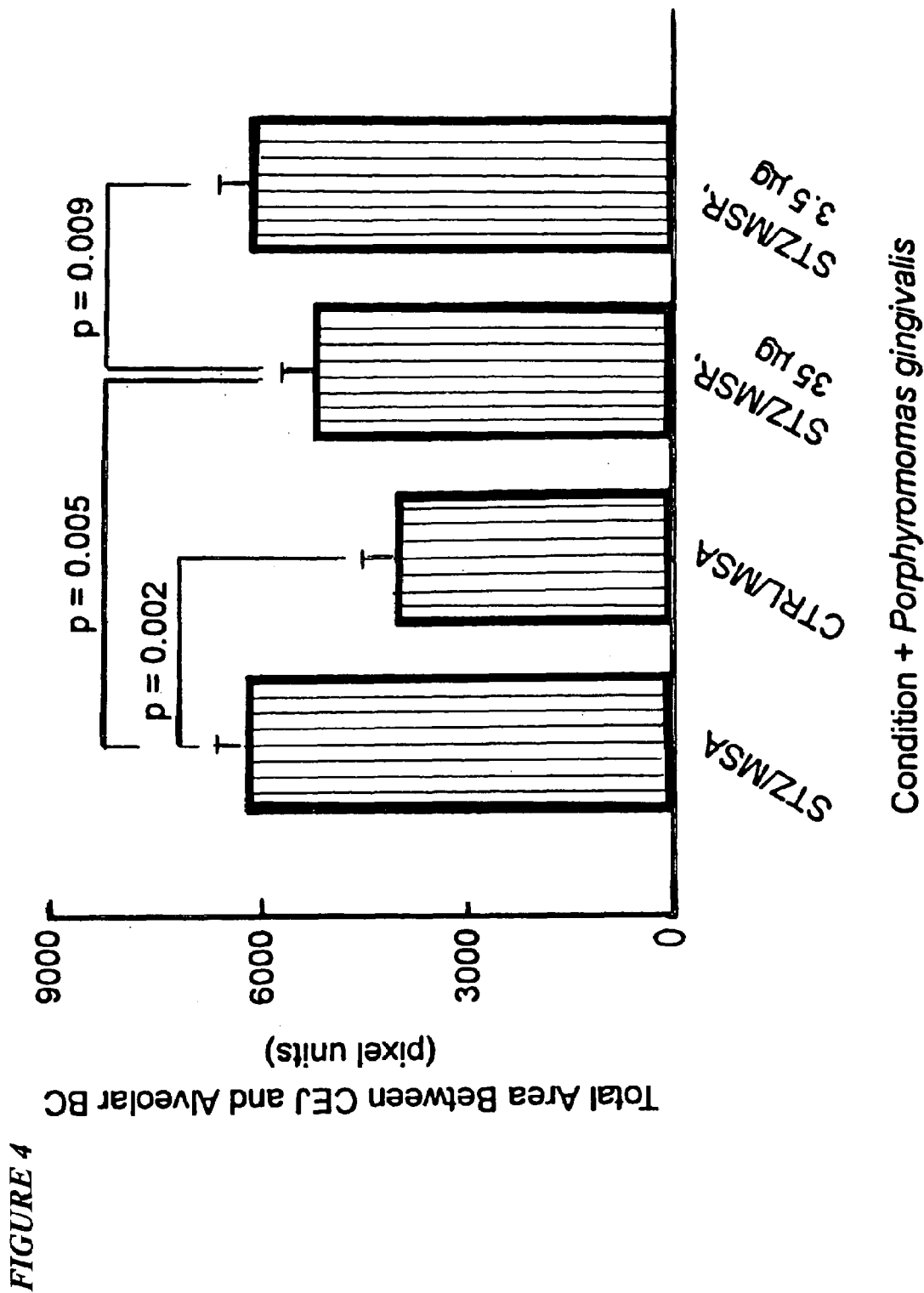

FIG. 4. Measurements of alveolar bone loss in mice treated with sRAGE. Statistical analysis=Group I vs. Group II—p=0.002; Group I vs. Group III—p=0.005; Group III vs. Group IV: p=0.009.

Delayed Type Hypersensitivity

Figure 5:
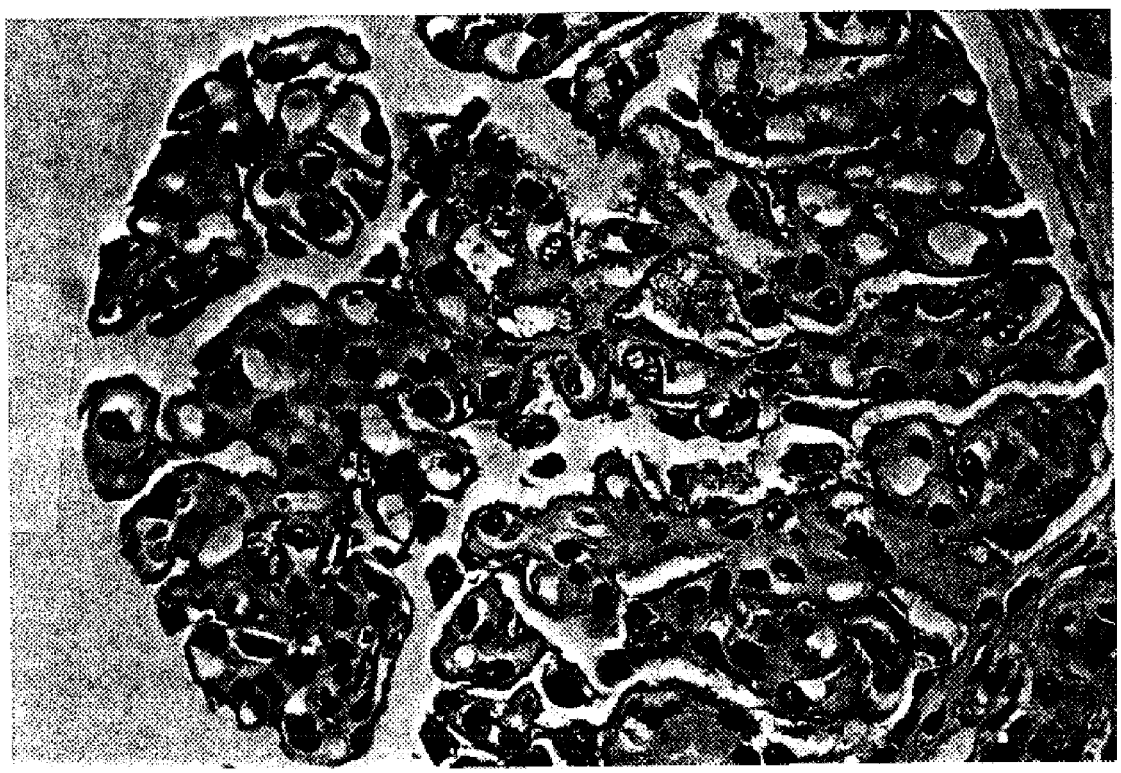

FIG. 5. Immunohistochemistry of human kidney (active lupus nephritis). Kidney tissue from a patient with active lupus nephritis was obtained, fixed in formalin and paraffin-embedded sections were prepared. Sections were stained with rabbit anti-RAGE IgG. Increased expression of RAGE was noted in the podocytes of the glomerulus.

Figure 6:
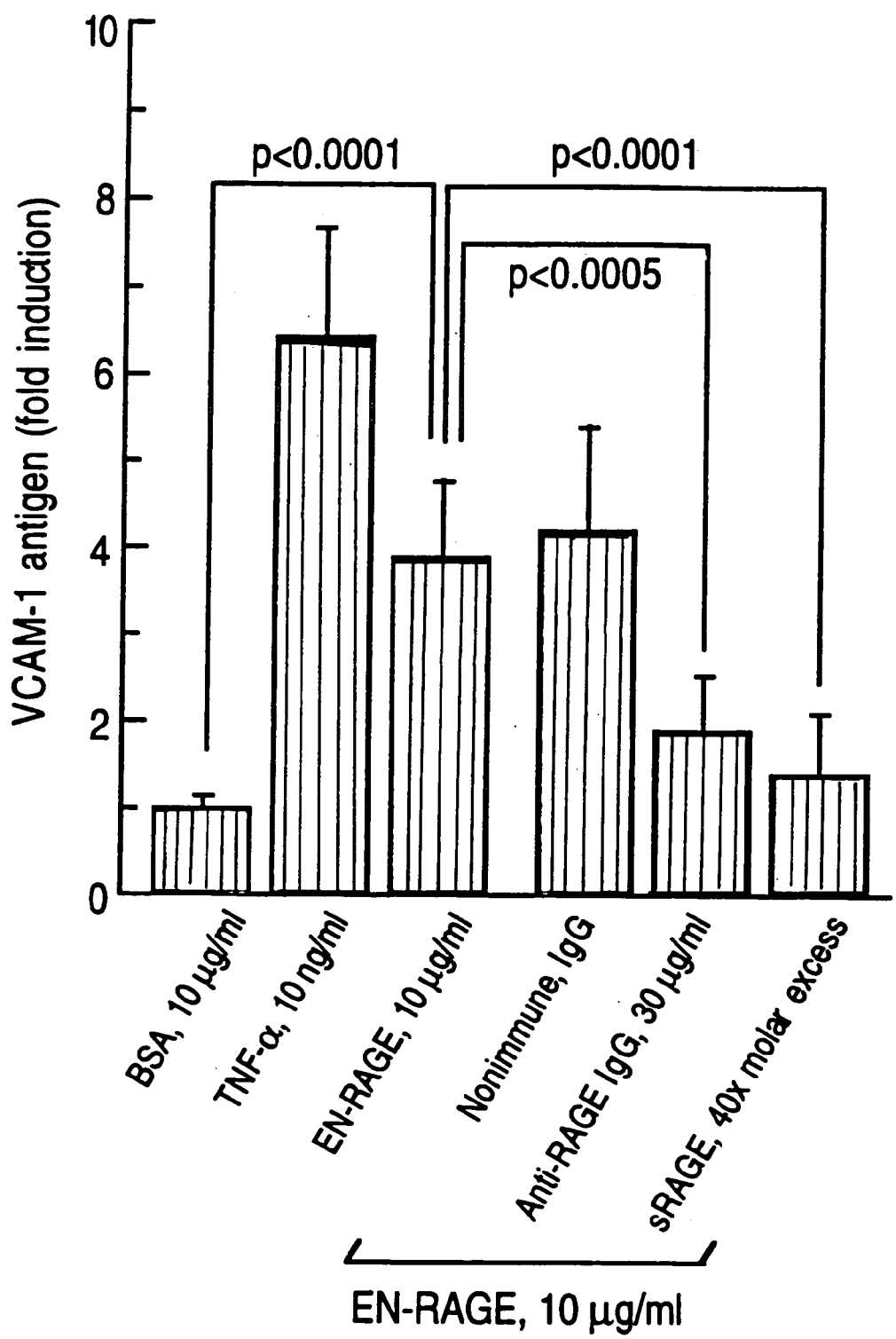

FIG. 6. Incubation of HUVECs with EN-RAGE results in increased cell surface VCAM-1. Human umbilical vein endothelial cells were cultured in serum-free RPMI 1640 without endothelial cell growth factor for 24 hrs and then stimulated with EN-RAGE or bovine serum albumin (BSA); both 10 μg/ml. Where indicated, cells were pretreated with rabbit anti-human RAGE IgG, nonimmune rabbit IgG; in certain cases, EN-RAGE was pretreated with the indicated concentration of soluble RAGE (sRAGE) for 2 hrs prior to stimulation with EN-RAGE. After eight hrs stimulation with EN-RAGE, cells were fixed as described above. Cell surface ELISA employing anti-VCAM-1 IgG was performed. Statistical considerations are shown in the figure.

Figure 7:
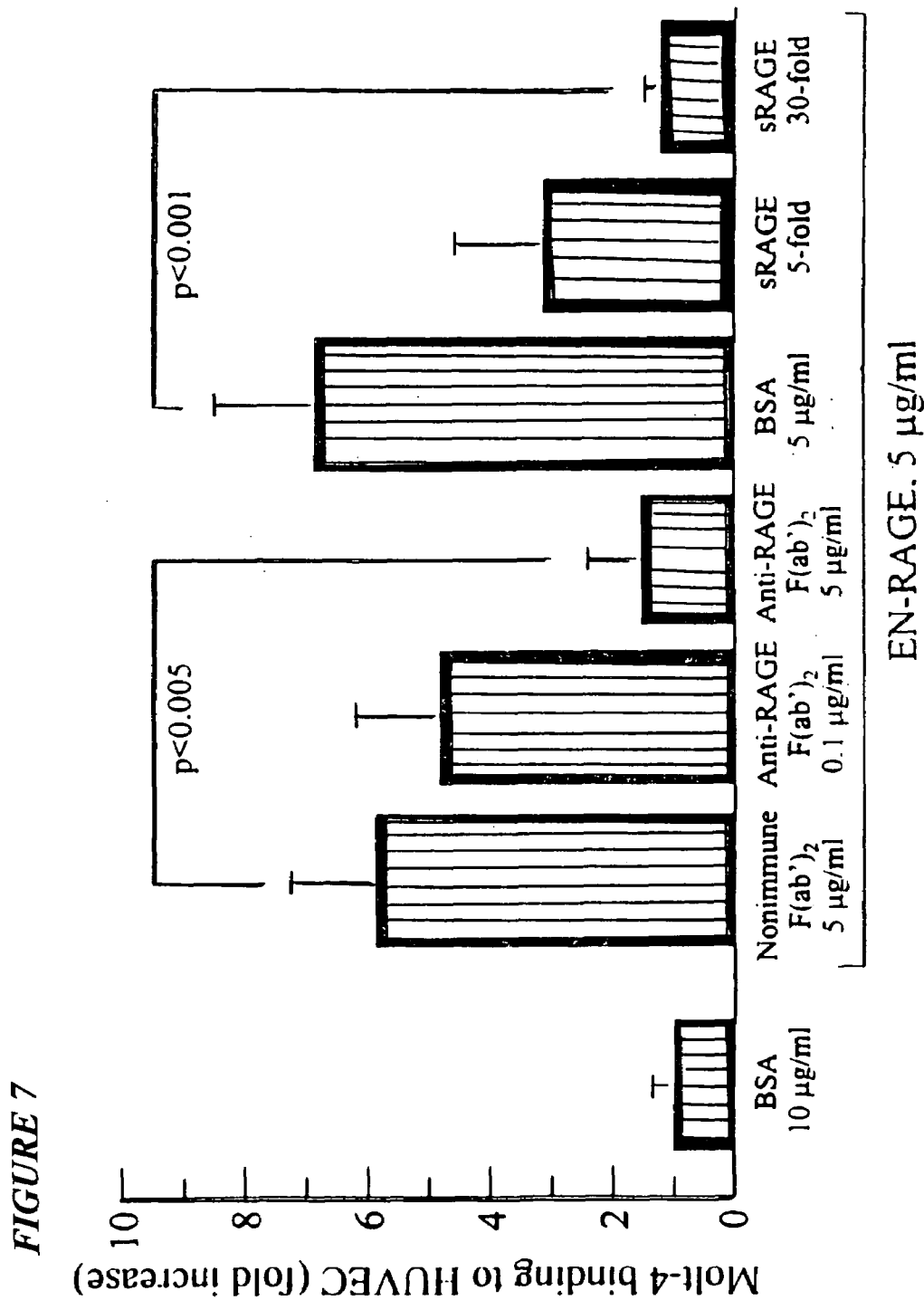

FIG. 7. Incubation of HUVECs with EN-RAGE increases VCAM-1 functional activity: increased binding of Molt-4 cells. Assessment of functional VCAM-1 activity was determined using $^{51}$Cr-labelled Molt-4 cells (ATCC) as described above. HUVEC were treated with either BSA (10 μg/ml) or EN-RAGE (5 μg/ml) for eight hrs. Molt-4 cells (5×10$^7$/ml) were incubated for 2 hrs in RPMI containing $^{51}$Cr (0.1 mCi). At the end of that time, cells were washed with PBS and then added to the monolayer of treated HUVEC for one hour. Unbound Molt-4 cells were removed by washing three times with PBS. Cells were then lysed in buffer containing triton-X 100 (2%) in order to release Molt-4 cell-bearing radioactivity. Statistical considerations are shown in the figure.

Figure 8:
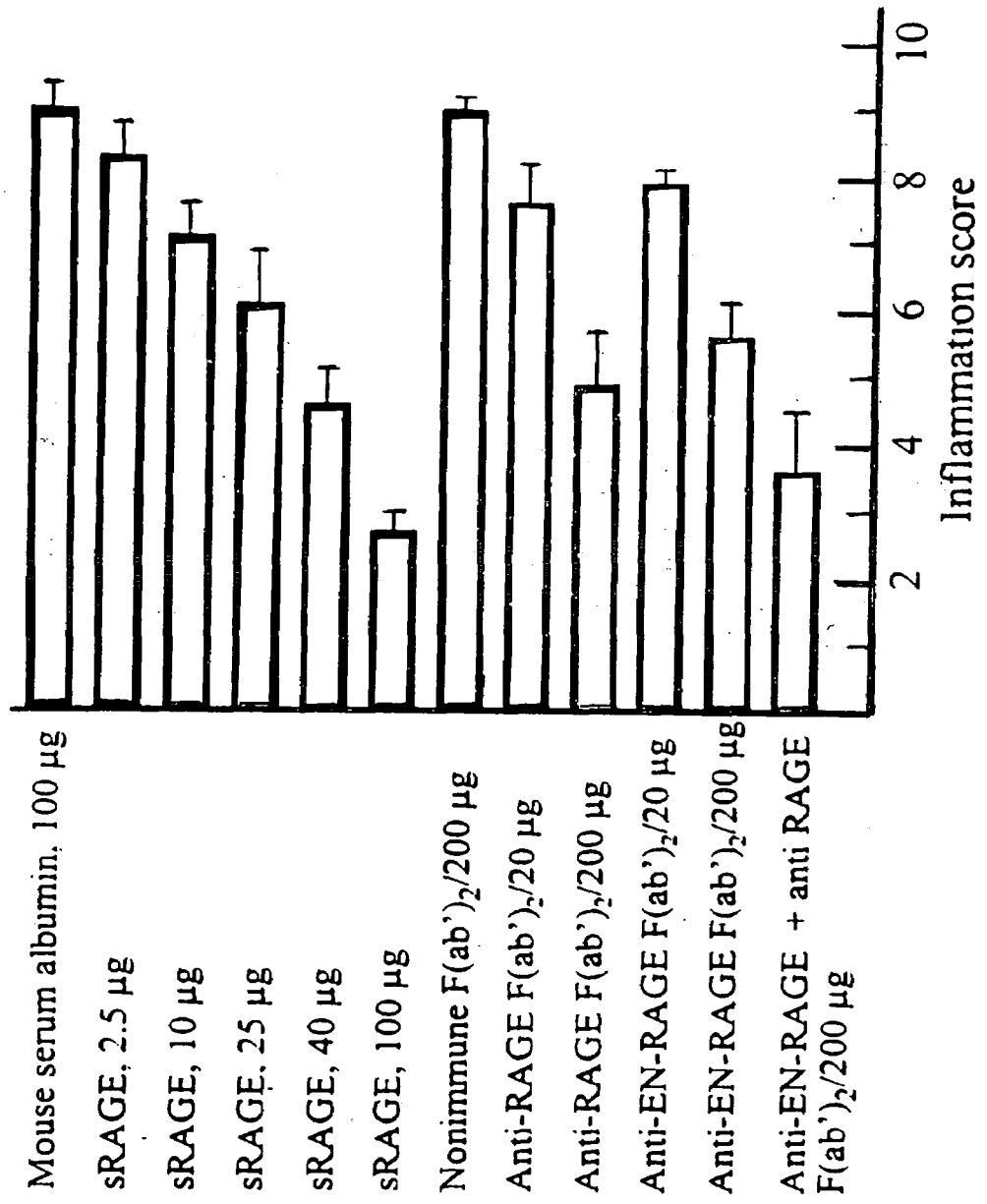

FIG. 8. Delayed hypersensitivity model: suppression of inflammation in the presence of soluble RAGE. CF-1 mice were sensitized with mBSA; after three weeks, mBSA was injected into the hind foot pad. Certain mice were treated with the indicated concentrations of mouse serum albumin, sRAGE or the indicated F(ab')$_2$ antibody fragments of RAGE or EN-PAGE. Inflammation score was defined as above (scale; 1–9).

FIG. 9. Nucleic Acid Sequence of bovine EN-RAGE. The cDNA for bovine EN-RAGE was cloned and deposited with Genbank at Accession No. AF 011757. (SEQ ID NO:16).

Collagen-Induced Arthritis

Figure 10:
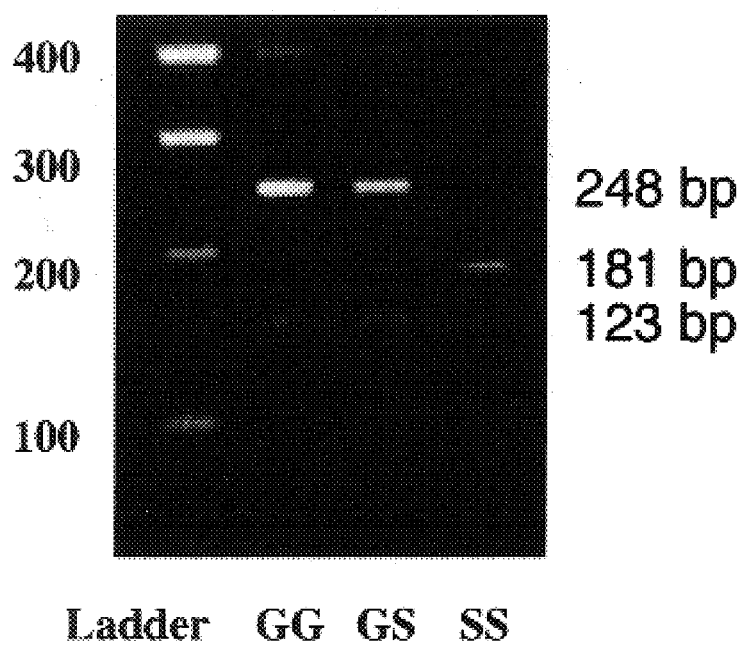

FIG. 10. Identification of wild-type RAGE and (G82S) and (S82S) polymorphisms. Genomic DNA was prepared from whole blood of controls, and subjects with RA. Amplification of exon 3 of the RAGE gene was performed as described; the resulting PCR products were digested with Alu 1. Upon agarose gel electrophoresis, identification of wild-type RAGE (G82G), and mutant RAGE (G82S) or (S82S) alleles was performed.

Figure 11A:
Figure 11B:
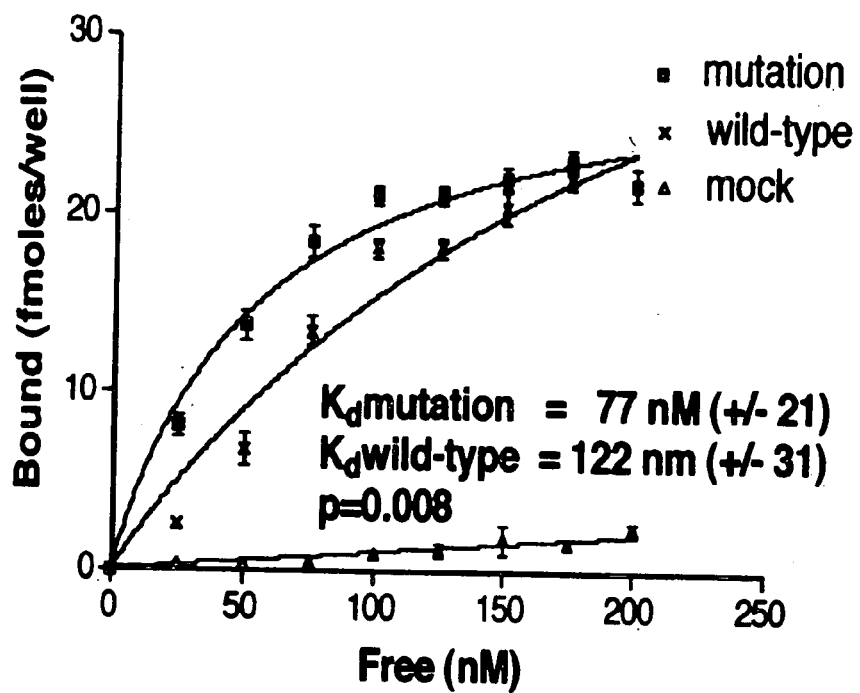
Figure 11C:
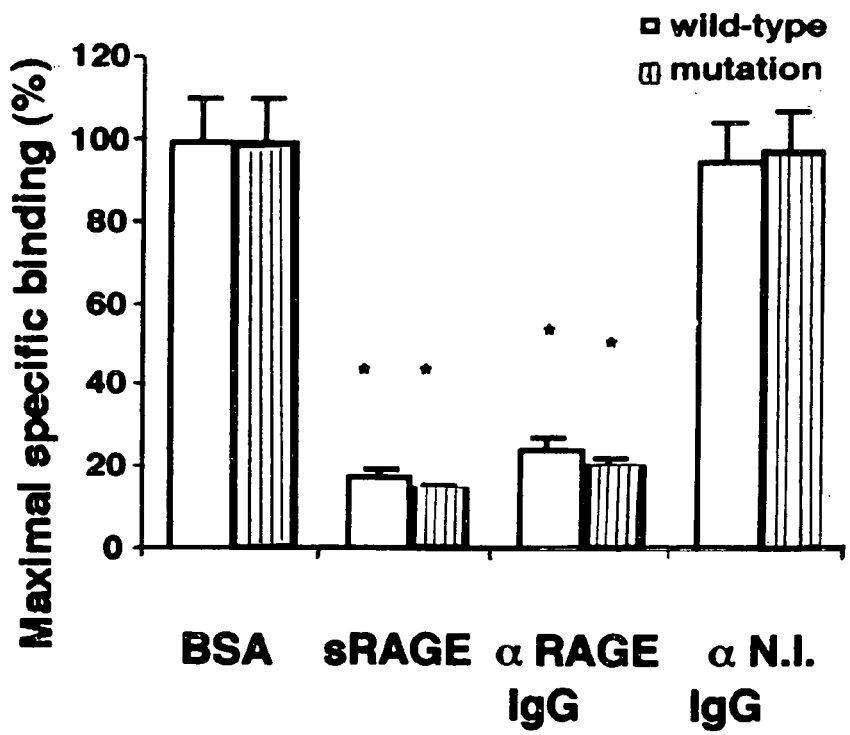
Figure 11E:
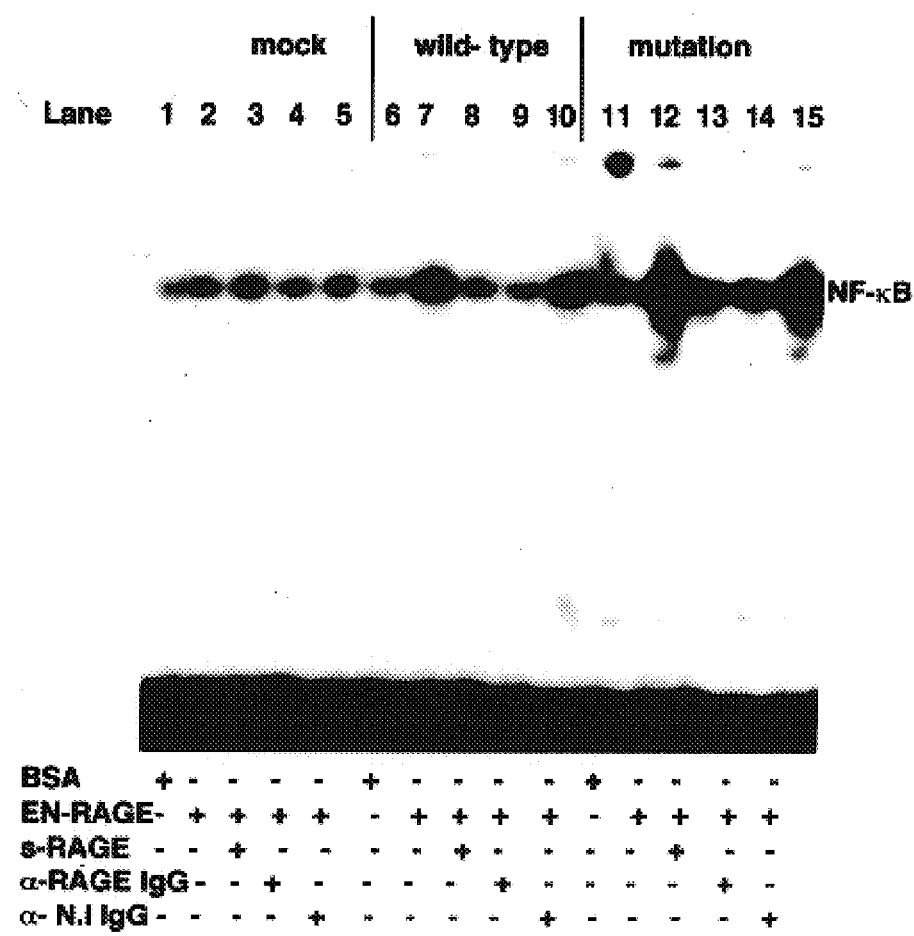

FIGS. 11A–11E. Transfection of CHO cells with mutant RAGE (82S) confers increased affinity and cellular responsiveness to EN-RAGE. CHO cells, which endogenously do not express RAGE, were stably-transfected with pcDNA3.1 vector containing cDNA encoding wild-type human RAGE or mutant (82S) human RAGE. "Mock" controls indicated empty vector. FIG. 11A. Immunoblotting. Lysates of stably-transfected CHO cells were prepared and subjected to immunoblotting using anti-human RAGE IgG (2 µg/ml). FIGS. 11B–C. Radioligand binding assays. Purified EN-RAGE was radiolabelled using $^{125}$-I and radioligand binding assays were performed in 96-well tissue culture dishes containing the indicated transfected CHO cells. Assays were performed in the presence of the indicated concentration of radiolabelled EN-RAGE±an 50-fold molar excess of unlabeled EN-RAGE. Elution of bound material was performed in a solution containing heparin. Equilibrium binding data were analyzed according to the equation of Klotz and Hunston. Where indicated, pretreatment with either antibodies (70 µg/ml), human soluble RAGE or bovine serum albumin (50-fold molar excess) was performed. The mean±standard deviation (SD) is shown. In FIG. 11C, * indicates $p<0.01$ versus respective controls. FIG. 11D. Activation of p44/p42 MAP kinases. The indicated stably-transfected CHO cells were incubated with EN-RAGE, 10 µg/ml, for one hr. Cell lysates were subjected to SDS-PAGE and transfer of the gels' contents to nitrocellulose. Immunoblotting was performed using anti-phosphorylated p44/p42 MAP kinase (1 µg/ml). Where indicated, pretreatment with either BSA or sRAGE (50-fold molar excess), or the indicated IgG (70 µg/ml), for 2 hrs was performed. Control immunoblotting using antibody to total p44/p42 MAP kinase revealed that there were no differences in levels of total p44/p42 in each group (not shown). FIG. 11E. Activation of NF-kB. Nuclear extracts were prepared from the indicated stably-transfected CHO cells incubated with EN-RAGE, 10 µg/ml, for 6 hrs, and EMSA was performed. Where indicated, cells were pretreated with either nonimmune/anti-RAGE IgG (70 µg/ml), soluble RAGE or BSA (50-fold molar excess) for 2 hrs prior to incubation with EN-RAGE. In FIGS. 11D–11E, bands were scanned into a densitometer, and band density was quantified using ImageQuant. These experiments were performed at least three times, and representative experiments are shown.

Figure 12A:
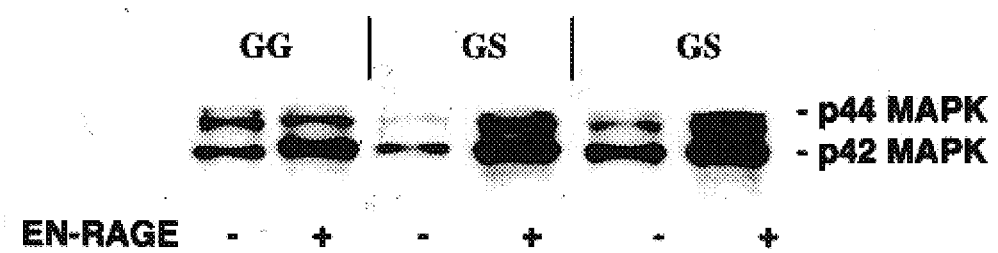
Figure 12B:
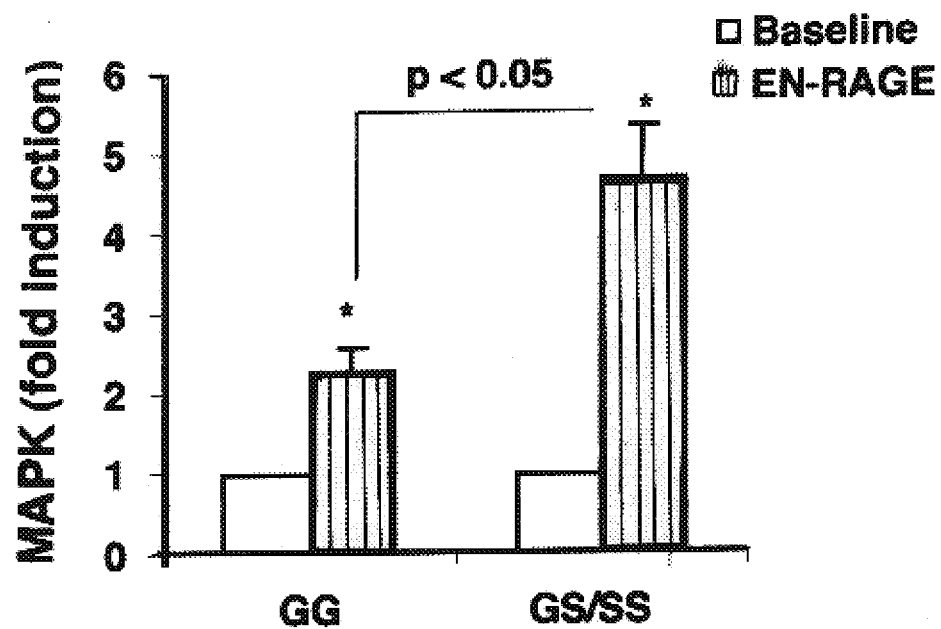
Figure 12C:
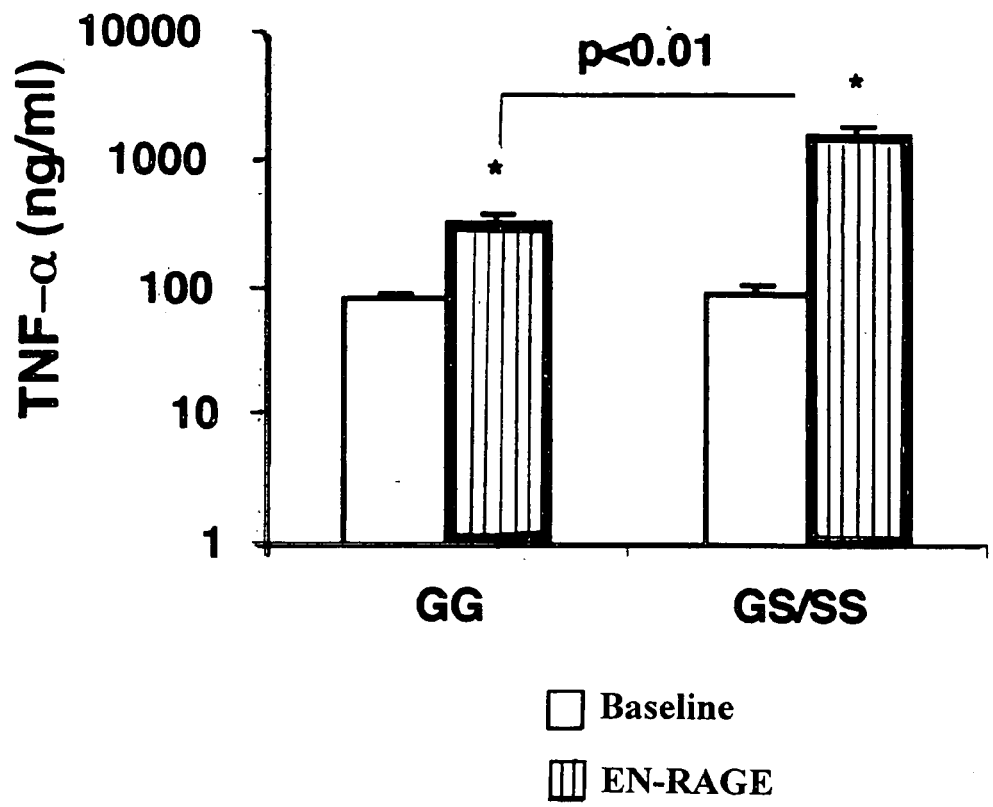
Figure 12D:
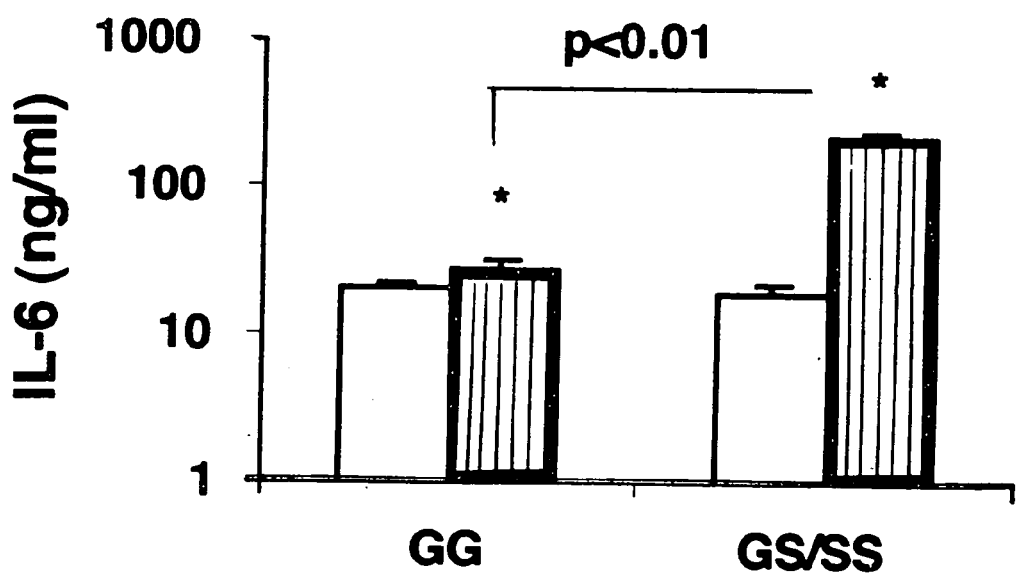
Figure 12E:
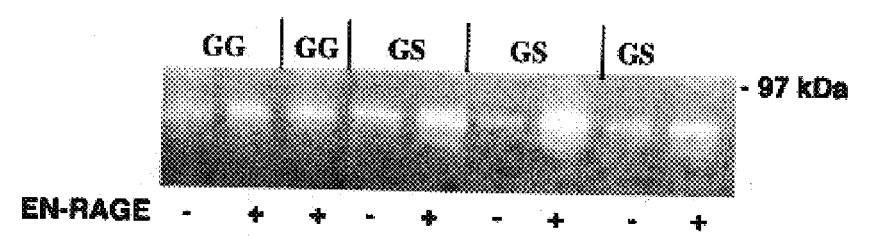
Figure 12F:
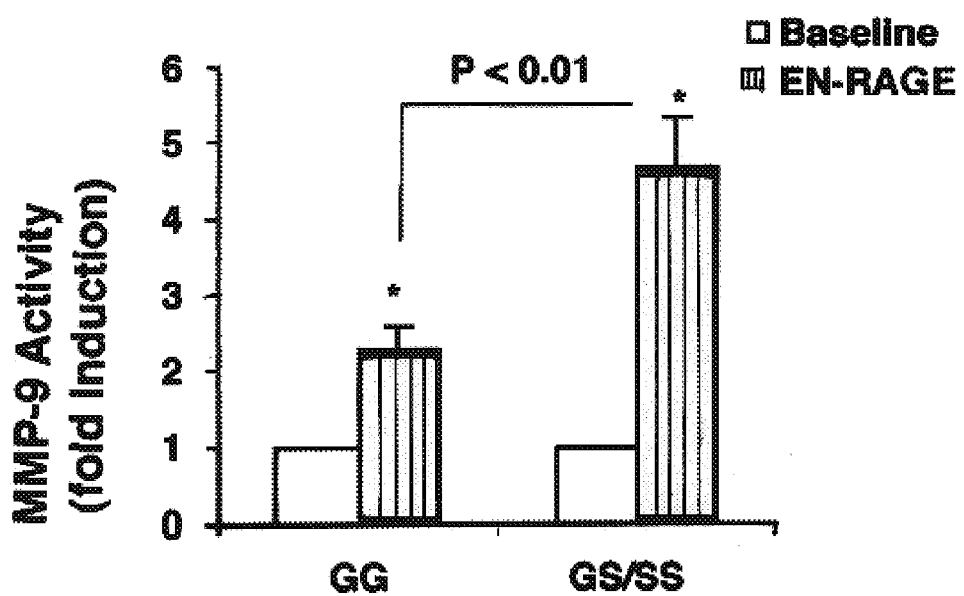

FIGS. 12A–F. Human peripheral blood mononuclear phagocytes (Mps) expressing RAGE (G82S) or (S82S) display increased responsiveness to EN-RAGE. MPs were purified from the blood of human subjects expressing wild-type RAGE, (G82S), or (S82S). For these experiments, MPs from 8 wild-type RAGE-bearing subjects, and 8 subjects bearing RAGE (G82S) or (S82S) were employed. FIGS. 12A–B. Activation of p44/p42 MAP kinases. The indicated MPs were incubated with EN-RAGE, 10 µg/ml, for one hr, or with no mediator. Cell lysates were prepared and immunoblotting performed using anti-phosphorylated p44/p42 MAP kinase. Densitometric analysis was performed and is shown in FIG. 12B. Since multiple experiments demonstrated that there were no differences in the extent of cellular activation in MPs bearing (G82S) or (S82S), these two groups were combined for analyses. Control immunoblotting using antibody to total p44/p42 MAP kinase revealed that there were no differences in levels of total p44/p42 in each group. The mean±SD is shown. FIGS. 12C–D. Generation of TNF-alpha (FIG. 12C) and IL-6 (FIG. 12D). Human MPs bearing the indicated RAGE alleles were cultured in the presence of either no mediator, or EN-RAGE, 10 µg/ml, for 14 hrs. Supernatants were retrieved and levels of TNF-alpha and IL-6 determined by ELISA. The mean±SD is shown. FIGS. 12E–F. Activity of MMP-9. Human MPs bearing the indicated RAGE alleles were cultured in the presence of either no mediator, or EN-RAGE, 10 µg/ml, for 14 hrs. Supernatants were retrieved and subjected to zymography to assess levels of activated MMP-9. Bands were scanned into a densitometer and band density was quantified. The mean±SD is shown. In FIGS. 12B, C, D and F, * indicates $p<0.01$ versus baseline. Other statistical comparisons are indicated.

Figure 13I:
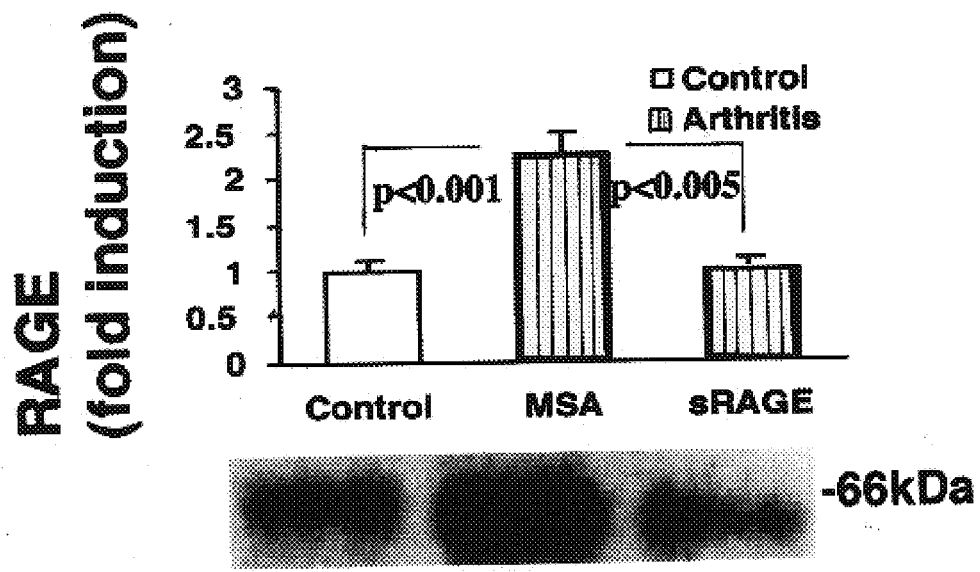
Figure 13J:
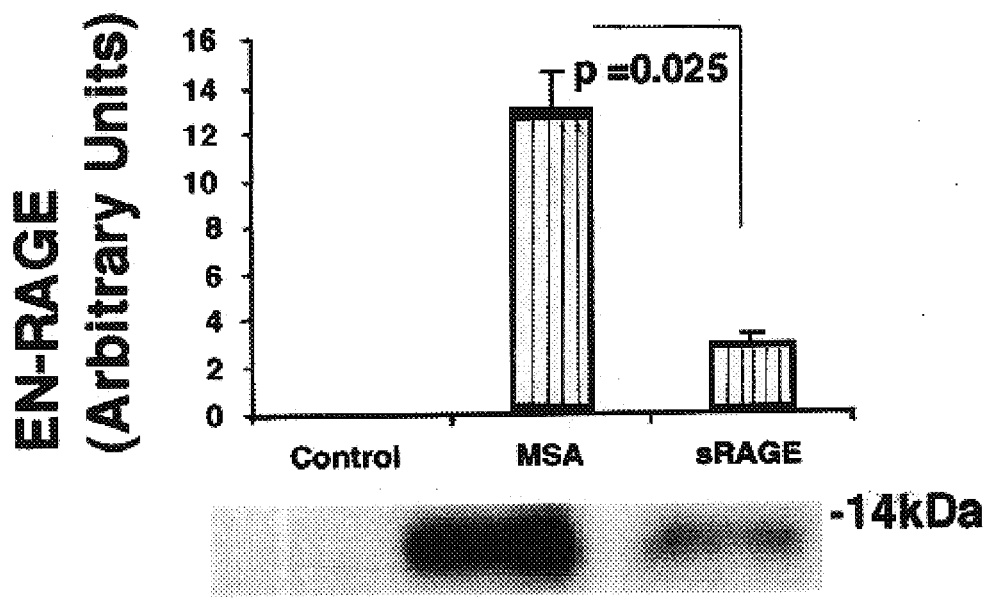

FIGS. 13A–J. Induction of arthritis by bovine type II collagen in dba/1 mice enhances expression of RAGE and EN-RAGEs. Dba/1 mice were immunized/challenged with bovine type II collagen. Control mice were not treated. Six weeks after immunization, joint tissue from the hind feet (FIGS. 13A–H) or stifle joint (FIGS. 13I–J) was prepared for study. FIGS. 13A–H. Histology. In FIGS. 13A–B, tissue was subjected to H&E analysis. Immunohistochemistry using anti-RAGE IgG (30 µg/ml) (FIGS. 13C–D); anti-EN-RAGE IgG (3 µg/ml) (FIGS. 13E–F); or rabbit nonimmune IgG (30 µg/ml) (FIGS. 13G–H) was performed. Scale bar: 300 Am. FIGS. 13I–J. Immunoblotting. Lysates were prepared from stifle joints and subjected to immunoblotting using anti-RAGE IgG (4.7 µg/ml) (FIG. 13I); or anti-EN-RAGE IgG (2 µg/ml) (FIG. 13J). For each group, n=3 mice per condition; representative bands are shown. Densitometric analysis of band intensity was performed, and the mean±SD is shown.

Figure 14B:
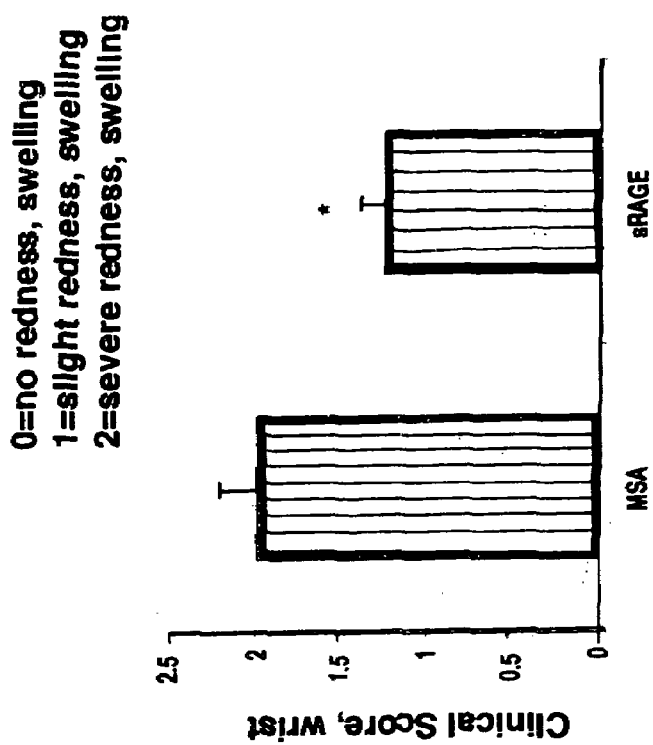
Figure 14A:
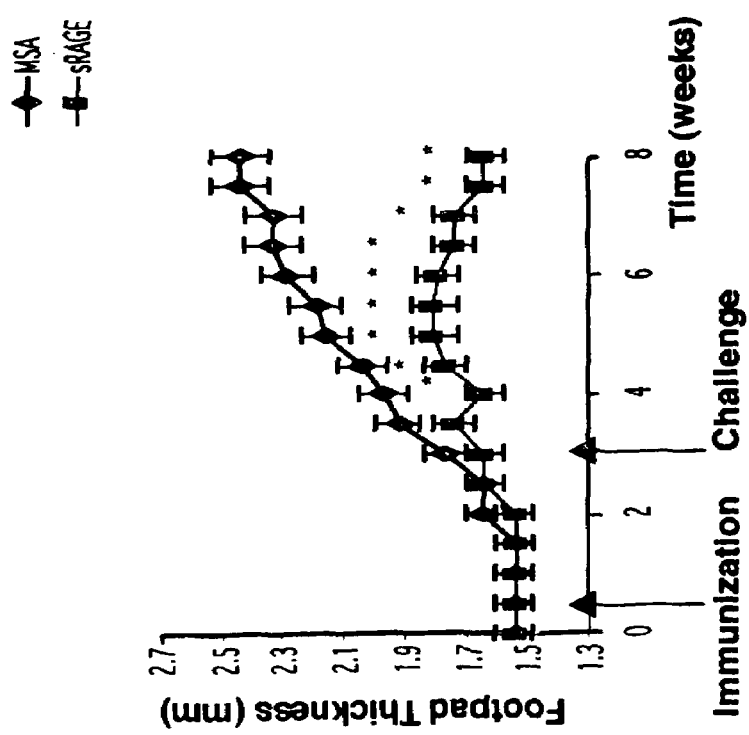
Figure 14C:
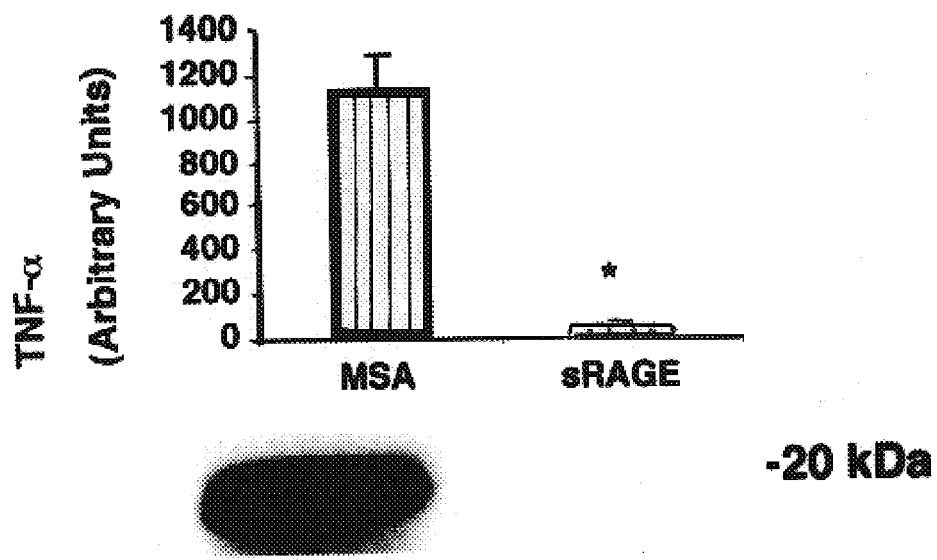
Figure 14D:
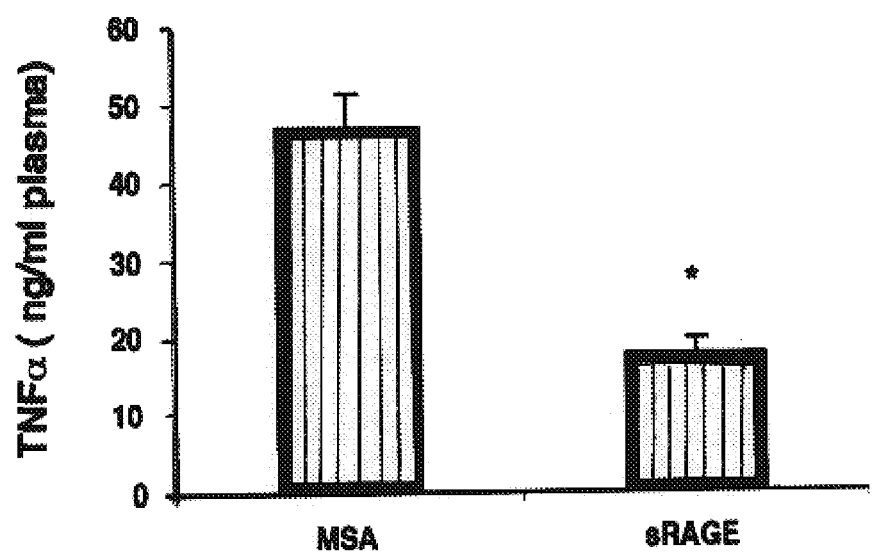
Figure 14F:
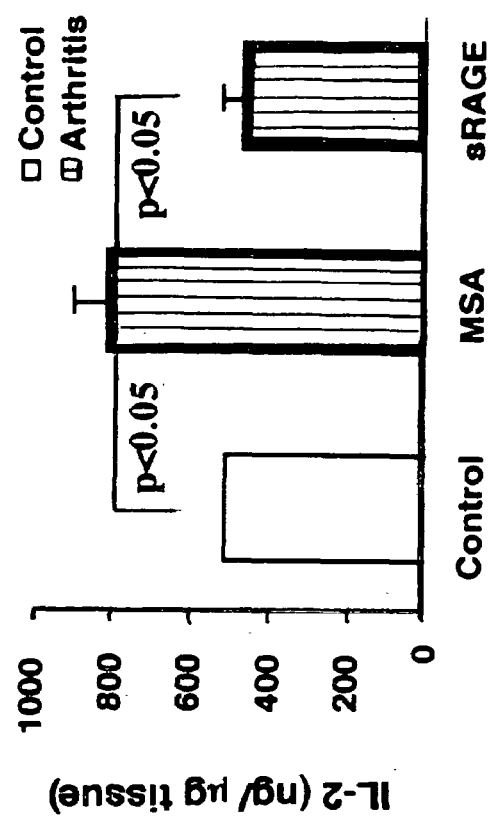
Figure 14E:
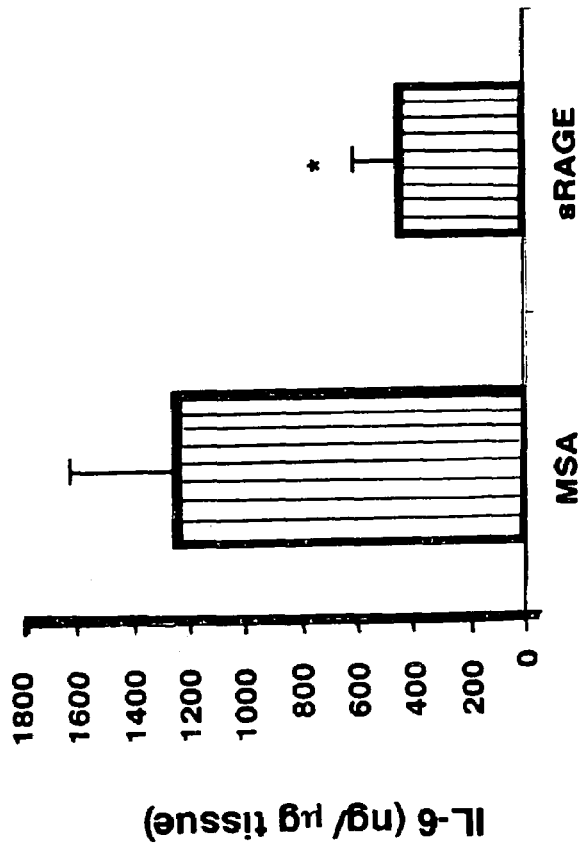

FIGS. 14A–F. Blockade of RAGE suppresses development of arthritis and markers of inflammation in dba/1 mice immunized/challenged with bovine type II collagen. FIGS. 14A–B, Clinical scoring. In FIG. 14A, at the indicated time points after immunization/challenge with bovine type II collagen and treatment with vehicle, murine serum albumin (MSA) or sRAGE, hind foot pad thickness was measured with calipers. The mean±standard deviation (SD) is shown; n=10 mice per group. * indicates $p<0.001$. In FIG. 14B, clinical scoring of wrist joint redness/swelling was performed by a blinded observer 6 weeks after immunization with bovine type II collagen. The mean±SD is shown; n=10 mice per group. * indicates $p=0.0001$. FIGS. 14C–F. Assessment of markers of inflammation. FIGS. 14C–D. TNF-alpha. In FIG. 14C, stifle joint tissue of mice with collagen-induced arthritis was retrieved six weeks after immunization with bovine type II collagen. Lysates were subjected to immunoblotting using anti-murine TNF-alpha IgG (1 µg/ml). In FIG. 14D, plasma from mice with collagen-induced arthritis was subjected to ELISA for levels of TNF-alpha. In FIG. 14C, 3 mice per group; and in FIG. 14D, 10 mice per group, were employed. The mean±SD is shown. In FIG. 14C, * indicates $p=0.001$; and in FIG. 14D, * indicates $p=0.03$. FIGS. 14E–F. IL-6 and IL-2. Stifle joint tissue was retrieved from control mice (clear bars) and mice with collagen-induced arthritis (black bars). Lysates were prepared and ELISA was performed for determination of levels of IL-6 (FIG. 14E) and IL-2 (FIG. 14F). Results are reported as ng/µg tissue. The mean±SD is shown; n=6 mice per group. In FIG. 14E, * indicates $p=0.04$.

Figure 15A:
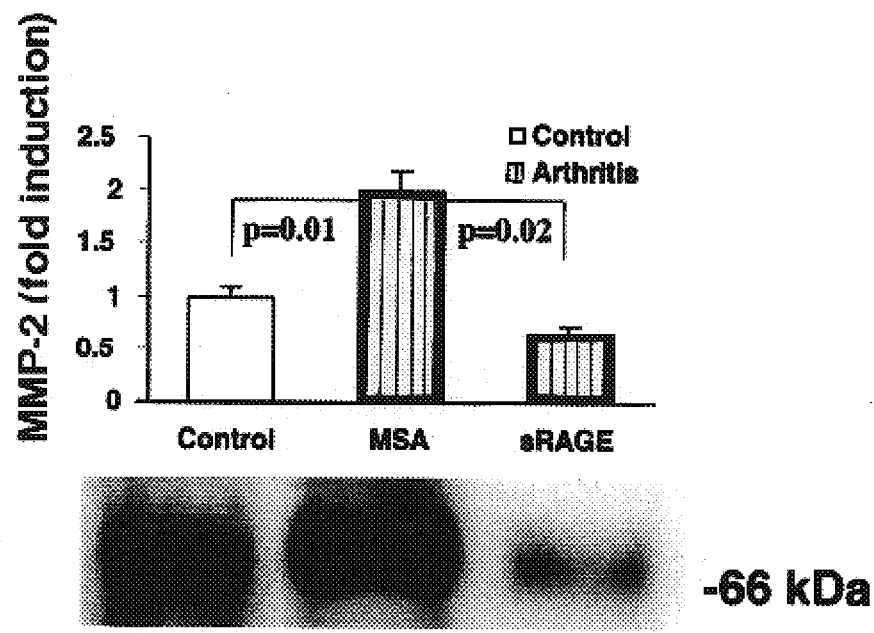
Figure 15B:
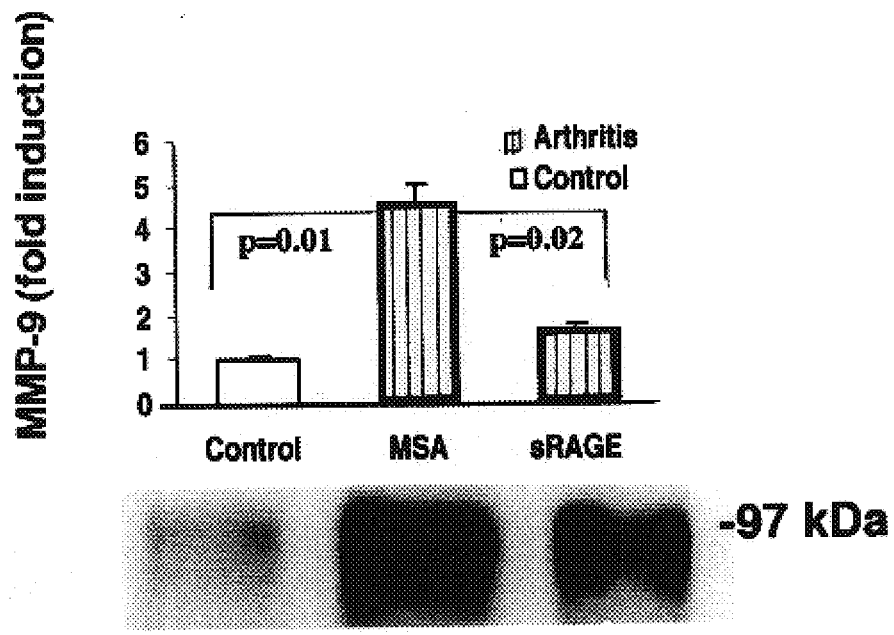

FIGS. 15A–D. Blockade of RAGE suppresses generation of MMPs in dba/1 mice immunized/challenged with bovine type II collagen. FIGS. 15A–B. Immunoblotting. Stifle joint tissue was retrieved from control mice (clear bars) and mice with bovine type II collagen-induced arthritis (black bars) six weeks after initial immunization. Lysates were prepared and subjected to immunoblotting using either anti-MMP-2

Figure 15C:
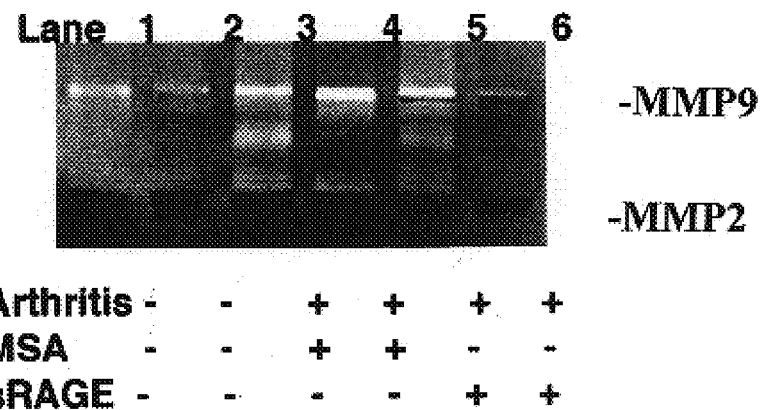
Figure 15D:
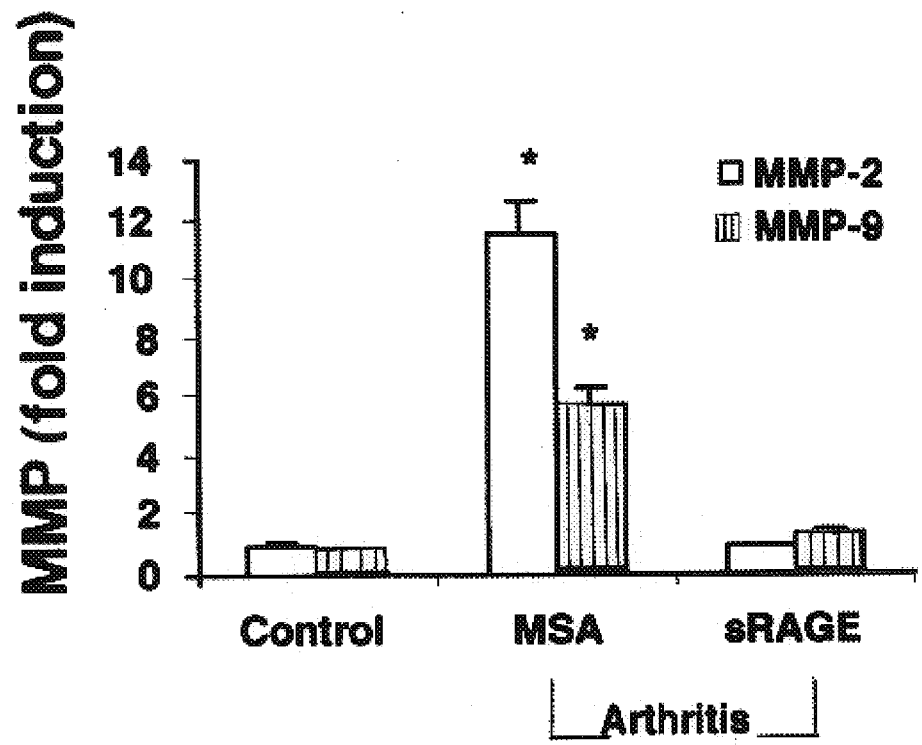

IgG (FIG. 15A) or anti-MMP-9 IgG (FIG. 15B). The mean±SD is shown; n=3 mice per group. FIGS. 15C–D. Zymography. Lysates were prepared from stifle joint tissue of control mice, or mice with collagen-induced arthritis. Zymography was performed and the results subjected to densitometric analysis. The mean±SD is shown; n=3 mice per group. Statistical analyses: MMP-2: * indicates p=0.001 vs control; and p=0.004 vs sRAGE. MMP-9: * indicates p=0.02 vs control; and p=0.005 vs sRAGE.

Figure 16A:
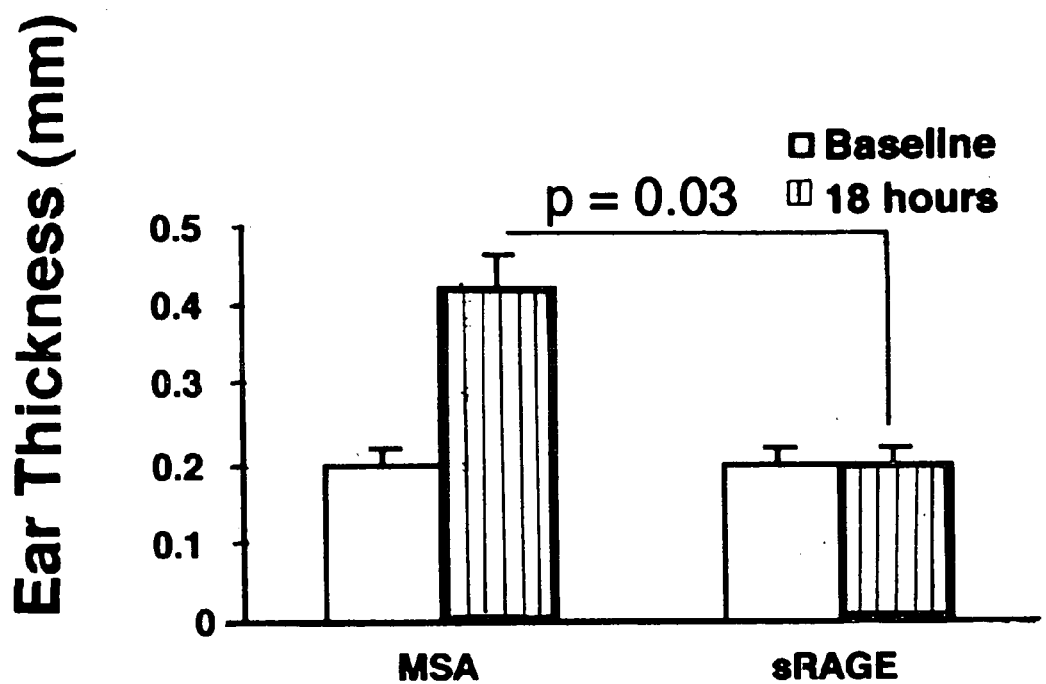
Figure 16B:
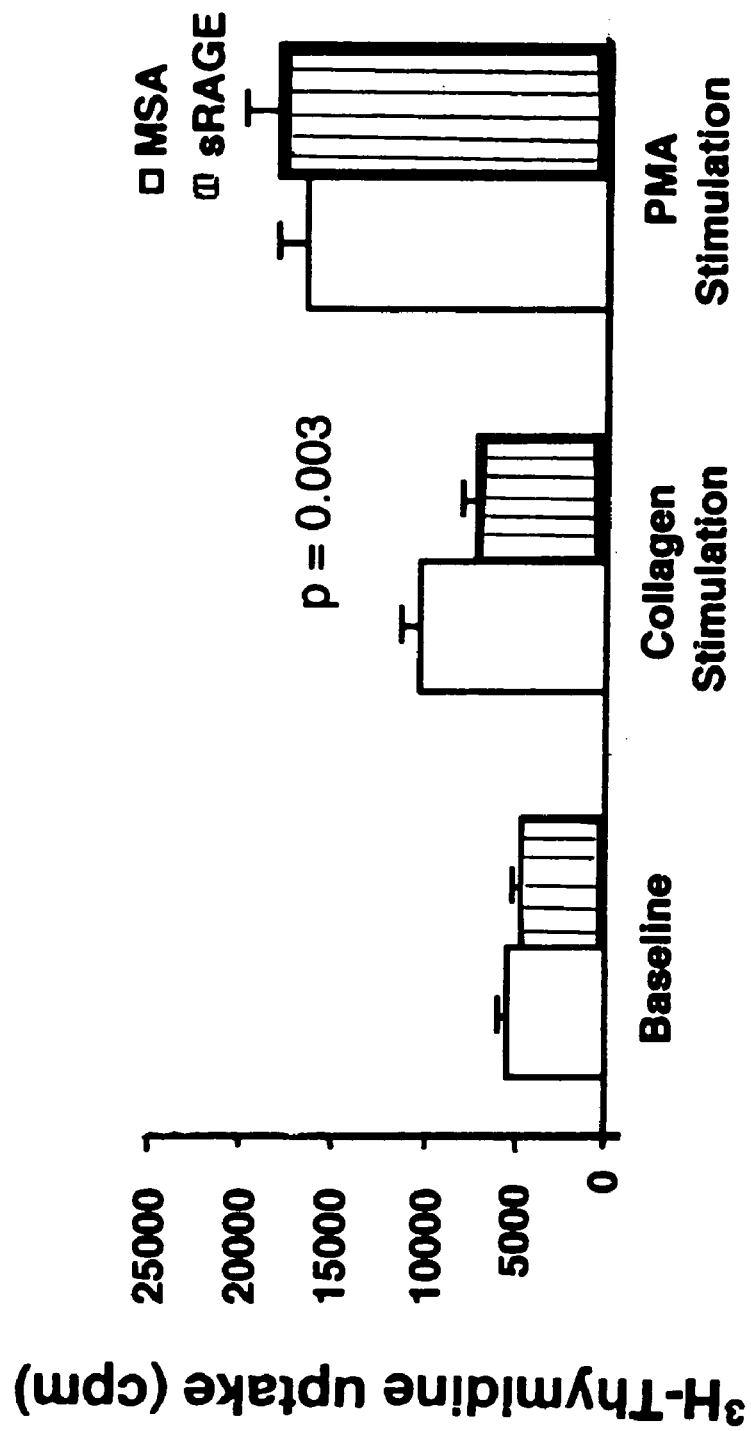

FIGS. 16A–B. Blockade of RAGE suppresses extra-articular inflammatory responses induced by bovine type II collagen. FIG. 16A Ear swelling. Six weeks after immunization with bovine type II collagen, MSA- and sRAGE-treated mice were injected with bovine type II collagen (10 µg) into ear tissue. Ear thickness was measured with calipers by a blinded observer immediately prior to local injection, and 18 hrs later. The mean±SD is shown; n=5 mice per group. FIG. 16B. Splenocyte proliferation. Splenocytes were prepared from the indicated mice at sacrifice, 6 weeks after immunization. Baseline levels of splenocyte proliferation, and proliferation in the presence of bovine type II collagen or PMA (0.1 µg/ml in each case) was determined. Note that no additional MSA or sRAGE was added to the culture system. The mean±SD is shown; n=5 mice per group.

Autoimmune Diseases, EAE

Figure 17:
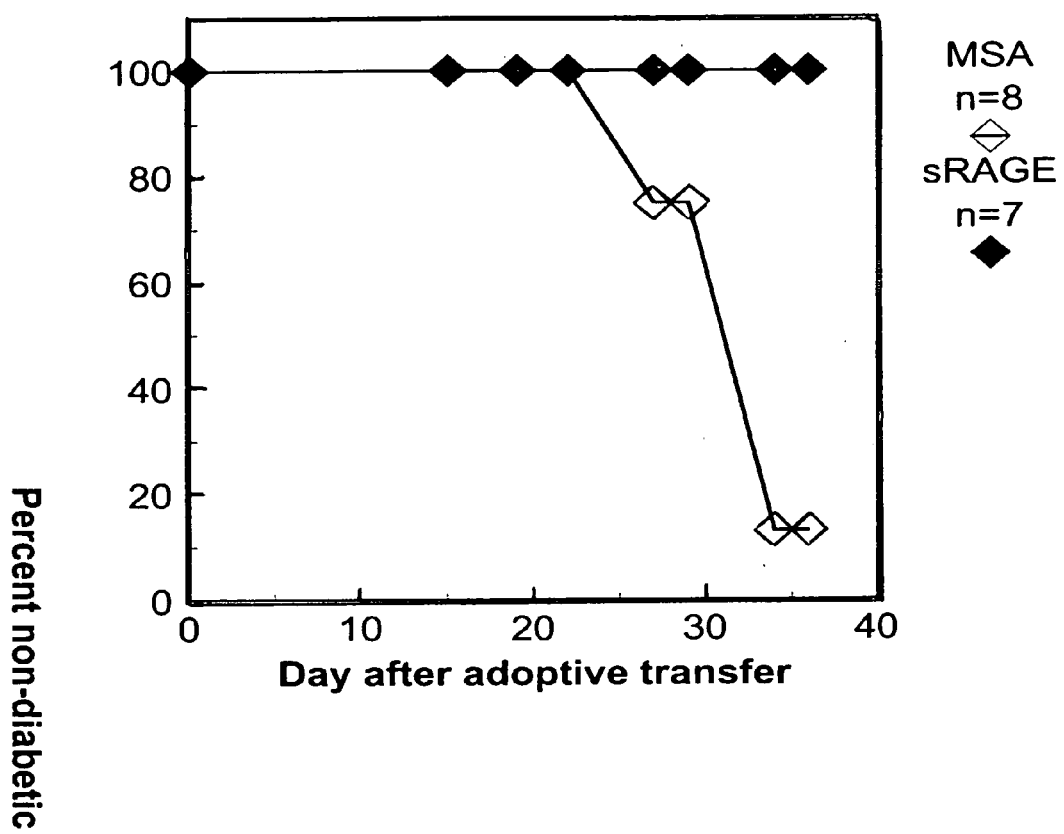

FIG. 17. Life Table analysis of development of diabetes in NOD.SCID recipients with and without treatment with sRAGE. A single experiment representative of 3 is presented. Soluble RAGE treatment reduced the development of diabetes in the NOD.SCID recipients. In pooled experiments (n=12 in sRAGE treated and n=13 controls, the incidence of diabetes at 35 days was 17% and 92%, respectively; p<0.001).

Figure 18:
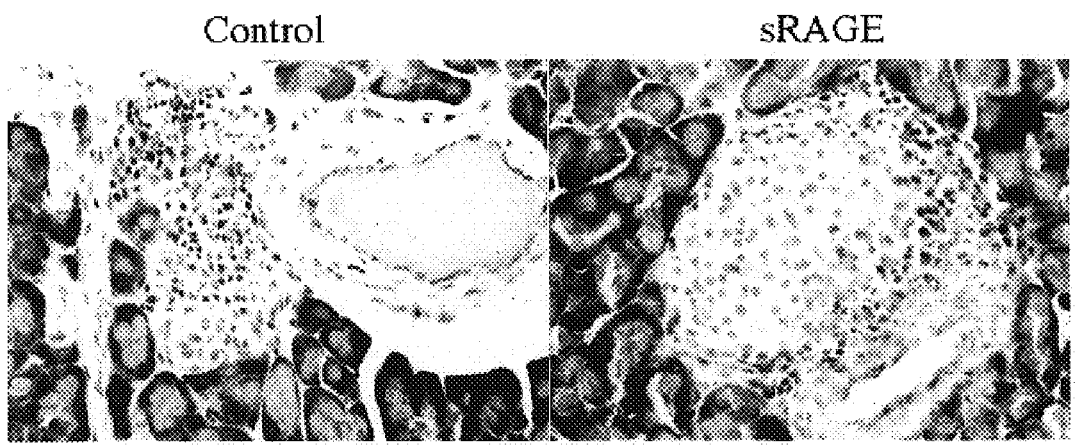

FIG. 18. Histology of islets in control and sRAGE treated recipients of splenocytes (H&E staining).

FIG. 19. Immunostaining for TNF-a and IL-1β in the islets of sRAGE-treated and control mice. Pancreases from untreated (control) or sRAGE-treated recipient mice were stained with antibodies to TNF (a) or IL-1β (b). Expression of these inflammatory cytokines (dark brown) was reduced in sRAGE-treated mice and, in the latter, was predominantly in the area of peri-insulitis.

Figure 20:
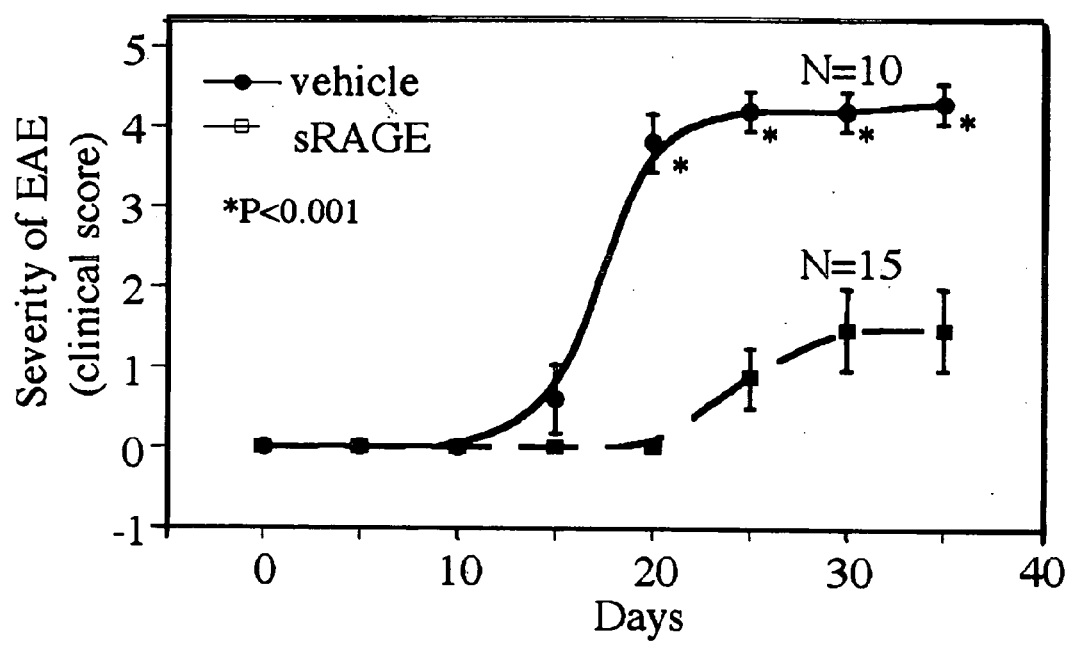

FIG. 20. Symptomatic scoring of EAE in B10.PL mice immunized with MBP-derived peptide and treated with vehicle (mouse serum albumin; 50 µg/day; fatty acid-free, Sigma) or sRAGE (50 µg/day).

Figure 21A:
Figure 21B:
Figure 21C:
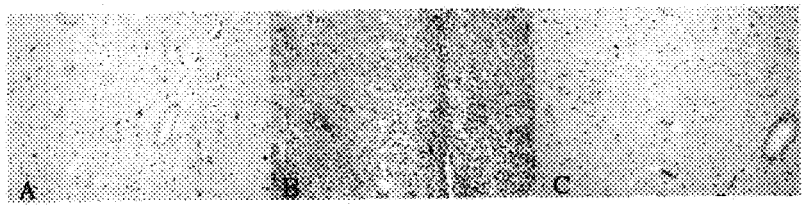
Figure 21D:
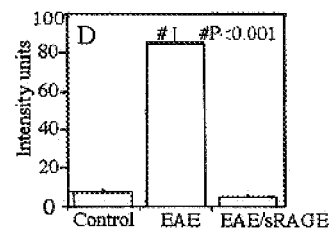

FIGS. 21A–21D. Histologic analysis (H&E) of spinal cord from mice immunized with MBP and treated with vehicle (FIG. 21B; the animal was sacrificed on day 21 with full-blown symptomatic EAE) or sRAGE (FIG. 21C; the animal was sacrificed on day 35 and was asymptomatic) as in FIG. 20. FIG. 21A shows normal mouse spinal cord. FIG. 21D shows quantitation of nuclei in affected areas (this reflects principally cells in the inflammatory infiltrate).

Figure 22:
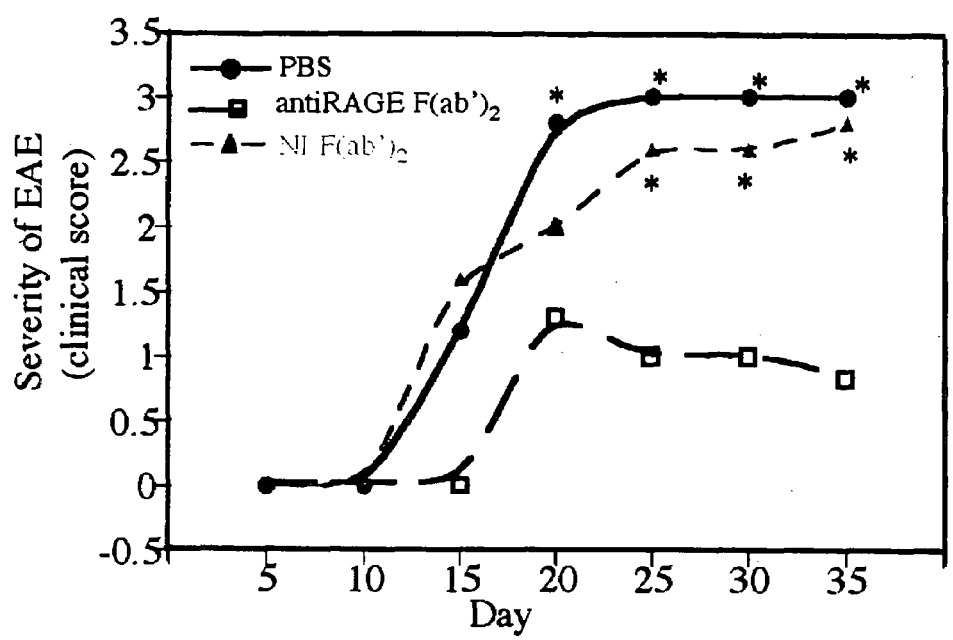

FIG. 22. Symptomatic analysis of B10.PL mice infused with activated 1AE10 cells as described in the text. As indicated, mice received either anti-PAGE IgG or nonimmune IgG for 15 days (see text for details experimental protocol).

DETAILED DESCRIPTION OF THE INVENTION

The present invention provides a method for treating inflammation in a subject which comprises administering to the subject an amount of soluble receptor for advanced glycation endproducts (sRAGE) effective to treat inflammation in the subject.

The present invention also provides a method for treating inflammation in a subject which comprises administering to the subject a therapeutically effective amount of an agent which inhibits binding of advanced glycation endproducts (AGEs) to any receptor for advanced glycation endproducts (RAGE) as to treat inflammation in the subject. The advanced glycation endproduct (AGE) may be a pentosidine, a carboxymethyllysine, a carboxyethyllysine, a pyrallines, an imidizalone, a methylglyoxal, an ethylglyoxal.

The present invention also provides a method for treating arthritis in a human subject which comprises administering to the subject a therapeutically effective amount of an agent which inhibits binding of advanced glycation endproducts (AGEs) to any receptor for advanced glycation endproducts (RAGE) as to treat arthritis in the subject.

Inflammation in the subject may be associated with any one or more of various conditions or diseases. For example, the inflammation in the subject may be due to a wound, to periodontal disease, to delayed-type hypersensitivity, to autoimmune disease, or to arthritis. The subject may be suffering from an autoimmune disease. In one embodiment, the subject is suffering from multiple sclerosis, autoimmune encephalitis, lupus nephritis, or autoimmune complications from diabetes. The subject may be suffering from diabetes, for example, type I diabetes. The subject may be suffering from Behchet's syndrome. The subject may be suffering from Sjogren's syndrome. The subject may be suffering from colitis, ulcerative colitis, inflammatory colitis, Crohn's disease or the like. The subject may be suffering from arthritis which is osteoarthritis, rheumatoid arthritis, collagen-induced arthritis, psoriatic arthritis, lupus-induced arthritis, or trauma-induced arthritis. The subject may be suffering from another overall condition or disease which includes a manifestation of inflammation, such as arthritis. In another embodiment, the subject is suffering from an allergy or is experiencing an allergic response. In one embodiment, the subject is suffering from asthma. The subject may be suffering from allergic asthma. In another embodiment, the subject is suffering from systemic lupus erythematosus, inflammatory lupus nephritis, septic shock or endotoxemia.

In a further embodiment, the subject is suffering from an autoimmune or inflammatory disorder in which recruitment of EN-RAGE-containing inflammatory cells occurs. In another embodiment, the subject is suffering from a bacterial-associated or other pathogen-associated infection.

The inflammation to be treated, in one embodiment of the invention, is caused by the accumulation of the AGEs in certain tissues dependent upon the ongoing biology in a subject. For example, the lesions in the blood vessels which can occur in a subject suffering from diabetes are due to the increased accumulation of AGEs in the presence of higher sugar in the blood. Therefore, the administration of the agent as described herein would reduce the interaction between the AGEs in the blood and the receptor for AGE, thereby reducing inflammation at that site. Therefore, the present invention encompasses inflammation which would occur in a subject at locations where the AGE products accumulate due to the overriding disease or condition.

The present invention also provides for a method for inhibiting periodontal disease in a subject which comprises administering topically to the subject a pharmaceutical composition which comprises sRAGE in an amount effective to accelerate wound healing and thereby inhibit periodontal disease. The pharmaceutical composition may comprise sRAGE in a toothpaste.

The present invention provides for a new proinflammatory cytokine-like molecule (EN-RAGE) (which has some sequence similarity to the family of calgranulin molecules). EN-RAGE is a protein located inside of inflammatory cells (such as neutrophils) and which may be released by such inflammatory cells. EN-RAGE has biological activity that may be responsible for the propagation and sustainment of an inflammatory response by interacting with cellular receptor RAGE.

The subject on which any of the methods of the invention is employed may be any mammal, e.g. a human subject, a murine subject, a bovine subject, a porcine subject, a canine subject, a primate subject, a feline subject, etc. Preferably, the subject is a human subject. However, for methods of identifying a compound or agent which is useful in treating inflammation, preferably, the subject is a primate, or murine subject.

The cell may be a eukaryotic cell. The cell may be a cell of a subject. The subject may be a human. The cell may be a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, a lymphocyte cell, a mesangial cell, a retinal epithelial cell, a retinal vascular cell a ganglion cell or a stem cell. The cell may also be other kinds of cells not explicitly listed herein. The cell may be any human cell. The cell may be a normal cell, an activated cell, a neoplastic cell, a diseased cell or an infected cell.

The Agent

In accordance with the method of this invention, the agent may comprise a polypeptide, a peptidomimetic, an organic molecule, a carbohydrate, a lipid, an antibody or a nucleic acid. The polypeptide may be synthesized chemically or produced by standard recombinant DNA methods. In accordance with the method of this invention, the polypeptide may comprise an advanced glycation endproduct polypeptide or a portion thereof, a receptor for an advanced glycation endproduct polypeptide or a portion thereof, a soluble receptor for advanced glycation endproduct polypeptide (sRAGE) or a portion thereof. In one embodiment of the invention, the portion of sRAGE is the V-domain of RAGE, which is the amino terminal 112 amino acids (not including the leader peptide).

The sequence of the V-domain of mature human RAGE is the following:

Ala Gln Asn Ile Thr Ala Arg Ile Gly Glu Pro Leu Val Leu Lys

Cys Lys Gly Ala Pro Lys Lys Pro Pro Gln Arg Leu Glu Trp Lys

Leu Asn Thr Gly Arg Thr Glu Ala Trp Lys Val Leu Ser Pro Gln

Gly Gly Gly Pro Trp Asp Ser Val Ala Arg Val Leu Pro Asn Gl

Ser Leu Phe Leu Pro Ala Val Gly Ile Gln Asp Glu Gly Ile Phe

Arg Cys Gln Ala Met Asn Arg Asn Gly Lys Glu Thr Lys Ser Asn

Tyr Arg Val Arg Val Tyr Gln Ile Pro Gly Lys Pro Glu Ile Val

Asp Ser Ala Ser Glu Leu Thr (SEQ ID NO:1).

The sequence of mature human RAGE not including the 22 amino acid leader sequence is:

```
Ala Gln Asn Ile Thr Ala Arg Ile Gly Glu Pro Leu Val Leu Lys

Cys Lys Gly Ala Pro Lys Lys Pro Pro Gln Arg Leu Glu Trp Lys

Leu Asn Thr Gly Arg Thr Glu Ala Trp Lys Val Leu Ser Pro Gln

Gly Gly Gly Pro Trp Asp Ser Val Ala Arg Val Leu Pro Asn Gly

Ser Leu Phe Leu Pro Ala Val Gly Ile Gln Asp Glu Gly Ile Phe

Arg Cys Gln Ala Met Asn Arg Asn Gly Lys Glu Thr Lys Ser Asn

Tyr Arg Val Arg Val Tyr Gln Ile Pro Gly Lys Pro Glu Ile Val

Asp Ser Ala Ser Glu Leu Thr Ala Gly Val Pro Asn Lys Val Gly

Thr Cys Val Ser Glu Gly Ser Tyr Pro Ala Gly Thr Leu Ser Trp

His Leu Asp Gly Lys Pro Leu Val Pro Asn Glu Lys Gly Val Ser

Val Lys Glu Gln Thr Arg Arg His Pro Glu Thr Gly Leu Phe Thr

Leu Gln Ser Glu Leu Met Val Thr Pro Ala Arg Gly Gly Asp Pro

Arg Pro Thr Phe Ser Cys Ser Phe Ser Pro Gly Leu Pro Arg His

Arg Ala Leu Arg Thr Ala Pro Ile Gln Pro Arg Val Trp Glu Pro

Val Pro Leu Glu Glu Val Gln Leu Val Val Glu Pro Glu Gly Gly

Ala Val Ala Pro Gly Gly Thr Val Thr Leu Thr Cys Glu Val Pro

Ala Gln Pro Ser Pro Gln Ile His Trp Met Lys Asp Gly Val Pro

Leu Pro Leu Pro Pro Ser Pro Val Leu Ile Leu Pro Glu Ile Gly

Pro Gln Asp Gln Gly Thr Tyr Ser Cys Val Ala Thr His Ser Ser

His Gly Pro Gln Glu Ser Arg Ala Val Ser Ile Ser Ile Ile Glu

Pro Gly Glu Glu Gly Pro Thr Ala Gly Ser Val Gly Gly Ser Gly

Leu Gly Thr Leu Ala Leu Ala Leu Gly Ile Leu Gly Gly Leu Gly

Thr Ala (SEQ ID NO:2).
```

The agent may be a composition which consists essentially of sRAGE. The agent may be a polypeptide which is fragment of sRAGE, for example, a fragment which is the V-domain of sRAGE.

In several embodiments of the present invention, the agent is a peptide having an amino acid sequence corresponding to the amino acid sequence of a V-domain of a RAGE or soluble RAGE is exemplified by the following amino acid sequences:

```
A-Q-N-I-T-A-R-I-G-E-P-L-V-L-K-C-K-G-A-P-K-K-P-P-Q-R-L-E-W-K
(SEQ ID No:3);

G-Q-N-I-T-A-R-I-G-E-P-L-V-L-S-C-K-G-A-P-K-K-P-P-Q-Q-L-E-W-K
(SEQ ID NO:4);

G-Q-N-I-T-A-R-I-G-E-P-L-M-L-S-C-K-A-A-P-K-K-P-T-Q-K-L-E-W-K
(SEQ ID NO:5);

D-Q-N-I-T-A-R-I-G-K-P-L-V-L-N-C-K-G-A-P-K-K-P-P-Q-Q-L-E-W-K
(SEQ ID NO:6).
```

The present invention provides for an isolated peptide having an amino acid sequence which corresponds to the amino acid sequence of the first 1–112 amino acids of human RAGE (which is the V-domain of human RAGE), or which corresponds to amino acids 5–35 of the V-domain of human RAGE, or any other smaller portion of the V-domain of human RAGE. Representative peptides of the present invention include but are not limited to peptides having an amino acid sequence which corresponds to amino acid numbers (2–30), (5–35), (10–40), (15–45), (20–50), (25–55), (30–60), (30–65), (10–60), (8–100), 14–75), (24–80), (33–75), (45–110) of human sRAGE protein.

The agent or inhibitor of the present invention may comprise a peptide having an amino acid sequence corresponding to amino acid numbers 1–30 of the V-domain of sRAGE (soluble receptor for advanced glycation endproducts). The sRAGE may be human, mouse, rat or bovine sRAGE.

The agent may be a peptide, a peptidomimetic, a nucleic acid or a small molecule. The terms "peptide" and "polypeptide" are used interchangably throughout. The peptide may be at least a portion of the sequence from amino acid 1 to amino acid 30 of sRAGE. The peptide may be a peptide consisting essentially of the amino acid sequence of SEQ ID NOS: 1, 2, 3, 4, 5, or 6. The peptide may be smaller than SEQ ID NO:1, retaining amino acid regions necessary to mimic the binding site of sRAGE. The peptide may comprise amino acids 1–112 of a RAGE protein (not including the leader sequence), i.e. the V-domain. The peptide may consist essentially of the V-domain of a RAGE proein (SEQ ID NO:1).

The polypeptide may be a peptidomimetic, a synthetic polypeptide or a polypeptide analog. The polypeptide may be a non-natural polypeptide which has chirality not found in nature, i.e. D-amino acids or L-amino acids.

The polypeptide may be a derivative of a natural polypeptide, a modified polypeptide, a labelled polypeptide, or a polypeptide which includes non-natural peptides. The peptidomimetic may be identified from screening large libraries of different compounds which are peptidomimetics to determine a compound which is capable of inhibiting interaction of an amyloid β peptide with a receptor for advanced glycation endproduct. In another embodiment, the polypeptide may be labeled with a detectable moiety. The detectable moiety may be selected from the group consisting of: a fluorescent label, a digoxigenin, a biotin, an enzyme, a radioactive atom, a paramagnetic ion, and a chemiluminescent label.

In another embodiment, the agent comprises a nucleic acid molecule which is a ribozyme or an antisense nucleic acid molecule.

The agent may comprise a peptide having an amino acid sequence corresponding to the amino acid sequence of a V-domain of a sRAGE linked to a second peptide, wherein the second peptide may be an albumin, a globulin or a peptide chosen from a group of peptides, wherein each peptide of the group comprises a different length peptide, and wherein the sequence of each peptide corresponds to any sequence of amino acids taken from within amino acid number 31 through amino acid number 281 of the human, bovine, mouse or rat sRAGE protein.

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Gutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The peptide or polypeptide of the present invention may comprise alterations to the sequences provided in SEQ ID NOS:1 to 6. The peptide of the present invention may comprise alterations in sequence which do not affect the functionality of the peptide in a negative way, but which may increase the functionality of the peptide in a position way, e.g. increase the potency of the peptide. Some examples of such alterations to the human sequence of the first 30 amino acids (1–30) of the V-domain of sRAGE (SEQ ID NO:1) are listed hereinbelow as examples:

(a) Substitute D-alanine for L-alanine in position 6;
(b) Substitue D-lysine for L-lysine in position 15;
(c) Substitute D-alanine for L-alanine in position 6 and D-lysine for L-lysine in position 15;
(d) Omit amino acids 1–5 of the V domain, making the N-amino end group L-alanine;
(e) Omit amino acids 1–5 of the V domain making the N-amino acid D-alanine;
(f) Substitute D-lysine for the L-lysine in the amino acid number "30" position of the V domain of Sequence I.D. No. 1;
(g) Substitute L-arginine for L-lysine in the 30 position of the V domain;
(h) Substitute L-arginine for L-lysine in the 30 position of the V domain and add glycine as the carboxyl terminal group to produce a 31 amino acid peptide;
(i) Substitute L-arginine for L-lysine in the 30 position of the amino acid peptide containing the amino acid sequence of 6–30 described for the V domaine of sRAGE;
(j) Substitute L-arginine for L-lysine in the 30 position of the amino acid peptide containing the amino acid sequence of 6–30 described for the V domaine of sRAGE and add glycine as the carboxyl terminal group to produce a 25 amino acid sequence peptide;
(k) Substitute D-lysine for L-lysine in the 30 position of the 6–30 amino acid sequence designated for the V domain;
(l) Substitute D-lysine for L-lysine in the 30 position of the 6–30 amino acid sequence designated for the V domaine and add L-alanine at the C-terminal position of the new 26 amino acid peptide;
(m) Substitute D-valine for L-valine in the 13 position of the V domaine 30 amino acid peptide designated 6–30 of the sRAGE V domain;
(n) Substitute D-valine for L-valine in the 13 position of the 25 amino acid peptide designated 6–30 of the sRAGE V domain;
(o) Substitute D-alanine for L-alanine in the 6 position of the 30 amino acid peptide and D-valine for L-valine in the 13 position of the 30 amino acid of the V domain;
(p) Substitute D-alanine for L-alanine in the 6 position and D-valine for L-valine in the 13 position of the 25 amino acid peptide designated 6–30 of the V domain of sRAGE;
(q) the above-listed (a)–(p) peptides derivatized through the carboxylic acid of position 30 with albumin, globulins or different length peptides composed of amino acids contained within positions 31 through 281 of the human, mouse, rat or bovine sRAGE protein.

In addition to naturally-occurring forms of polypeptides derived from sRAGE, the present invention also embraces other polypeptides such as polypeptide analogs of sRAGE which have the equivalent funcationality of the peptide of SEQ ID NO:1 or 2 or a more potent or more positive functionality. Such analogs include fragments of sRAGE. Following the procedures of the published application by Alton et al. (WO 83/04053), one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives of sRAGE polypeptide. Such products share at least one of the biological properties of sRAGE but may differ in others. As examples, products of the invention include those which are foreshortened by e.g., deletions; or those which are more stable to hydrolysis (and, therefore, may have more pronounced or longerlasting effects than naturally-occurring); or which have been altered to delete or to add one or more potential sites for O-glycosylation and/or N-glycosylation or which have one or more cysteine residues deleted or replaced by e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within sRAGE, which fragments may possess one property of sRAGE and not others. It is noteworthy that activity is not necessary for any one or more of the polypeptides of the invention to have therapeutic utility or utility in other contexts, such as in assays of sRAGE antagonism. Competitive antagonists may be quite useful in, for example, cases of overproduction of sRAGE.

Of applicability to polypeptide analogs of the invention are reports of the immunological property of synthetic peptides which substantially duplicate the amino acid sequence in naturally-occurring proteins, glycoproteins and nucleoproteins. More specifically, relatively low molecular weight polypeptides have been shown to participate in immune reactions which are similar in duration and extent to the immune reactions of physiologically-significant proteins such as viral antigens, polypeptide hormones, and the like. Included among the immune reactions of such polypeptides is the provocation of the formation of specific antibodies in immunologically-active animals [Lerner et al., 1981; Ross et al., 1981; Walter et al., 1981; Wong et al., 1982; Baron et al., 1982; Dressman et al., 1982; and Lerner, Scientific American, 1983. See also, Kaiser et al., 1984] relating to biological and immunological properties of synthetic peptides which approximately share secondary structures of peptide hormones but may not share their primary structural conformation.

The polypeptide of the present invention may be a peptidomimetic compound which may be at least partially unnatural. The peptidomimetic compound may be a small molecule mimic of a portion of the amino acid sequence of sRAGE. The compound may have increased stability, efficacy, potency and bioavailability by virtue of the mimic. Further, the compound may have decreased toxicity. The peptidomimetic compound may have enhanced mucosal intestinal permeability. The compound may be synthetically prepared. The compound of the present invention may include L-, D-, DL- or unnatural amino acids, alpha, alpha-disubstituted amino acids, N-alkyl amino acids, lactic acid (an isoelectronic analog of alanine). The peptide backbone of the compound may have at least one bond replaced with PSI-[CH=CH] (Kempf et al. 1991). The compound may further include trifluorotyrosine, p-Cl-phenylalanine, p-Br-phenylalanine, poly-L-propargylglycine, poly-D,L-allyl glycine, or poly-L-allyl glycine.

One embodiment of the present invention is a peptidomimetic compound having the biological activity of preventing accelerated athersclerosis in a subject wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

In accordance with the method of this invention, the agent may comprise a peptide, a peptidomimetic, an organic molecule, a carbohydrate, a lipid, an antibody or a nucleic acid. The peptide of this invention may comprise an advanced glycation endproduct peptide or a portion thereof, a receptor for advanced glycation endproduct peptide or a portion thereof, a soluble receptor for advanced glycation endproduct peptide or a portion thereof. The peptide of the present invention may comprise any part of the first 112 amino acids of the sRAGE protein. The peptide of the present invention may comprise the V-domain of a soluble RAGE protein. The peptide of the present invention may be a smaller portion of the V-domain of a soluble RAGE protein. The peptide of the present invention may be a peptide which corresponds to the V-domain of human RAGE, mouse RAGE, rat RAGE, bovine RAGE or fish RAGE.

In accordance with the method of this invention, the agent may be a peptide (polypeptide), a peptidomimetic, an organic molecule, a carbohydrate, a lipid, an antibody or a nucleic acid. In the case of polypeptides, the polypeptide may be an advanced glycation endproduct (AGE) polypeptide or a portion thereof, a receptor for advanced glycation endproduct polypeptide or a portion thereof, a soluble receptor for advanced glycation endproduct polypeptide or a portion thereof, e.g., soluble RAGE, or a recombinant polypeptide. The polypeptide may be the V-domain of sRAGE, or amino acids 1–30 of the V-domain of sRAGE. The polypeptide of this invention may comprise an advanced glycation endproduct polypeptide or a portion thereof, a receptor for advanced glycation endproduct polypeptide or a portion thereof, a soluble receptor for advanced glycation endproduct polypeptide or a portion thereof. The polypeptide of the present invention may comprise any part of the first 112 amino acids of the sRAGE protein. The polypeptide of the present invention may comprise the V-domain of a soluble RAGE protein. The polypeptide of the present invention may be a smaller portion of the V-domain of a soluble RAGE protein. The polypeptide of the present invention may be a polypeptide which corresponds to the V-domain of human RAGE, mouse RAGE, rat RAGE, bovine RAGE or fish RAGE. The polypeptide may be synthesized chemically or produced by standard recombinant DNA methods. In the case of antibodies, the antibody may be an anti-RAGE antibody or an anti-RAGE F(ab')$_2$ fragment.

Of applicability to polypeptide analogs of the invention are reports of the immunological property of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically-significant proteins such as viral antigens, polypeptide hormones, and the like. Included among the immune reactions of such polypeptides is the provocation of the formation of specific antibodies in immunologically-active animals [Lerner et al., *Cell,* 23, 309–310 (1981); Ross et al., *Nature,* 294, 654–658 (1981); Walter et al., *Proc. Natl. Acad. Sci. USA,* 78, 4882–4886 (1981); Wong et al., Proc. Natl. Sci. USA, 79, 5322–5326 (1982); Baron et al., Cell, 28, 395–404 (1982); Dressman et al., Nature, 295, 185–160 (1982); and Lerner, Scientific American, 248, 66–74 (1983). See also, Kaiser et al. [Science, 223, 249–255 (1984)] relating to biological and immunological properties of synthetic peptides which approximately share secondary structures of peptide hormones but may not share their primary structural conformation.

The present invention also encompasses a pharmaceutical composition which comprises a therapeutically effective amount of the peptide having an amino acid sequence corresponding to the amino acid sequence of a V-domain of a receptor for advanced glycation endproduct (RAGE) and a pharmaceutically acceptable carrier. The carrier may be a diluent, an aerosol, a topical carrier, an aqueous solution, a nonaqueous solution or a solid carrier. The carrier may be a polymer or a toothpaste. The pharmaceutical composition may comprise the peptide having an amino acid sequence corresponding to the amino acid sequence of a V-domain of a RAGE linked to a second peptide, wherein the second peptide may be an albumin, a globulin or a peptide chosen from a group of peptides, wherein each peptide of the group comprises a different length peptide, and wherein the sequence of each peptide corresponds to any sequence of amino acids taken from within amino acid number 31 through amino acid number 281 of the human sRAGE protien.

In one embodiment of the invention, the agent consists essentially of a portion of the peptide consisting of an amino acid sequence corresponding to the amino acid sequence of a V-domain of a receptor for advanced glycation endproduct. In one embodiment, the agent consists of sRAGE. In one embodiment, the agent consists of the V-domain of sRAGE.

In one embodiment of the invention, the agent is an inhibitor of the interaction between RAGE and AGE or RAGE and another binding partner. The inhibitor comprises a peptide, a peptidomimetic compound, a nucleic acid molecule, a small molecule, an organic compound, an inorganic compound, or an antibody or a fragment thereof. The inhibitor may be the isolated peptide having an amino acid sequence corresponding to the amino acid sequence of a V-domain of a receptor for advanced glycation endproduct. In one embodiment, the inhibitor is capable of specifically binding to the amyloid-β peptide. In one embodiment, the agent consists essentially of a peptide having the amino acid sequence A-Q-N-I-T-A-R-I-G-E-P-L-V-L-K-C-K-G-A-P-K-K-P-P-Q-R-L-E-W-K (SEQ ID NO:7). In another embodiment, the agent consists essentially of a peptide consisting of the amino acid sequence A-Q-N-I-T-A-R-I-G-E (SEQ ID NO:8).

In one embodiment of the invention, the agent is an antibody. In accordance with the method of this invention, the antibody may comprise an anti-RAGE antibody or an anti-RAGE F(ab')$_2$ fragment. The fragment of the antibody which is useful in the present invention is that which binds the antigen. Antibodies may be humanized or chimeric. The antibody may be a human antibody, a primate antibody, or a murine antibody. The portion or fragment of the antibody may comprise a complementarity determining region or a variable region. In one embodiment, the antibody may be capable of specifically binding to the receptor for advanced glycation endproduct. The antibody may be a monoclonal antibody, a polyclonal antibody.

The agent may be conjugated to a carrier. The peptide or agent may be linked to an antibody, such as a Fab or a Fc fragment for specifically targeted delivery. The carrier may be a diluent, an aerosol, a topical carrier, an aquous solution, a nonaqueous solution or a solid carrier.

As used herein, the term "suitable pharmaceutically acceptable carrier" encompasses any of the standard pharmaceutically accepted carriers, such as phosphate buffered saline solution, acetate buffered saline solution (a likely vehicle for parenteral administration), water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

When administered orally or topically, such agents and pharmaceutical compositions would be delivered using different carriers. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients. The specific carrier would need to be selected based upon the desired method of deliver, e.g., PBS could be used for intravenous or systemic delivery and vegetable fats, creams, salves, ointments or gels may be used for topical delivery.

This invention also provides for pharmaceutical compositions including therapeutically effective amounts of protein compositions and/or agents capable of inhibiting the binding of an amyloid-β peptide with a receptor for advanced glycation endproduct in the subject of the invention together with suitable diluents, preservatives, solubilizers, emulsifiers, adjuvants and/or carriers useful in treatment of neuronal degradation due to aging, a learning disability, or a neurological disorder. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the agent, complexation with metal ions, or incorporation of the agent into or onto particulate preparations of polymeric agents such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the agent or composition. The choice of compositions will depend on the physical and chemical properties of the agent capable of alleviating the symptoms of the cognitive disorder of memory or the learning disability in the subject.

The agent of the present invention may be delivered locally via a capsule which allows sustained release of the agent or the peptide over a period of time. Controlled or sustained release compositions include formulation in lipophilic depots (e.g., fatty acids, waxes, oils). Also comprehended by the invention are particulate compositions coated with polymers (e.g., poloxamers or poloxamines) and the agent coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Portions of the agent of the invention may be "labeled" by association with a detectable marker substance (e.g., radiolabeled with $^{125}$I or biotinylated) to provide reagents useful in detection and quantification of compound or its receptor bearing cells or its derivatives in solid tissue and fluid samples such as blood, cerebral spinal fluid or urine.

When administered, agents (such as a peptide comprising the V-domain of sRAGE) are often cleared rapidly from the circulation and may therefore elicit relatively short-lived pharmacological activity. Consequently, frequent injections of relatively large doses of bioactive agents may by required to sustain therapeutic efficacy. Agents modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified agents (Abuchowski et al., 1981; Newmark et al., 1982; and Katre et al., 1987). Such modifications may also increase the agent's solubility in aqueous solution, eliminate aggregation, enhance the physical and chemical stability of the agent, and greatly reduce the immunogenicity and reactivity of the agent. As a result, the desired in vivo biological activity may be achieved by the administration of such polymer-agent adducts less frequently or in lower doses than with the unmodified agent.

Attachment of polyethylene glycol (PEG) to agents is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the agent or against cells which may produce the compound. The agent of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

Administration

The administration of the agent may be effected by intralesional, intraperitoneal, intramuscular or intravenous injection; by infusion; or may involve liposome-mediated delivery; or topical, nasal, oral, anal, ocular or otic delivery. The administration may comprise subcutaneous, vaginal, sublingual, uretheral, transdermal, or intrathecal.

The agent may be delivered hourly, daily, weekly, monthly, yearly (e.g. in a time release form) or as a one time delivery. The delivery may be continuous delivery for a period of time, e.g. intravenous delivery. The agent or pharmaceutical composition of the present invention may be delivered intercranially or into the spinal fluid.

In accordance with the method of this invention, the therapeutically effective amount may comprise a dose of from about 200 ng/day/kg body weight to about 200,000 ng/day/kg body weight or from about 50 ng/day/kg to about 500,000 ng/day/kg body weight.

In the practice of the method administration may comprise daily, weekly, monthly or hourly administration, the precise frequency being subject to various variables such as age and condition of the subject, amount to be administered, half-life of the agent in the subject, area of the subject to which administration is desired and the like.

In connection with the method of this invention, a therapeutically effective amount of may include dosages which take into account the size and weight of the subject, the age of the subject, the severity of the symptom, the surface area of the wound, the efficacy of the agent, the method of delivery of the agent and the history of the symptoms in the subject. One of ordinary skill in the art would be readily able to determine the exact dosages and exact times of administration based upon such factors. For example, a therapeutically effective amount may a dose of from about 200 ng/day/kg body weight to about 200,000 ng/day/kg body weight. In this regard, it has been shown that 24 micrograms administered intraperitoneally daily (on days 3–9) to wounded diabetic mice resulted in greatly reduced inflammation. In this regard, the dose may also be administered as a single dose or as a series of doses over a period of time.

The effective amount of the agent may comprise from about 0.000001 mg/kg body weight to about 100 mg/kg body weight. In one embodiment, the effective amount may comprise from about 0.001 mg/kg body weight to about 50 mg/kg body weight. In another embodiment, the effective amount may range from about 0.01 mg/kg body weight to about 10 mg/kg body weight. The actual effective amount will be based upon the size of the agent, the biodegradability of the agent, the bioactivity of the agent and the bioavailability of the agent. The agent may be delivered topically in a creme or salve carrier. It may be reapplied as needed based upon the absorbancy of the carrier to the skin or mucosa or wound. If the agent does not degrade quickly, is bioavailable and highly active, a smaller amount will be required to be effective. The effective amount will be known to one of skill in the art; it will also be dependent upon the form of the agent, the size of the agent and the bioactivity of the agent. One of skill in the art could routinely perform empirical activity tests for a agent to determine the bioactivity in bioassays and thus determine the effective amount.

Wound Healing

One example of inflammation in a subject is that which is associated with a wound in a subject. One embodiment of treating inflammation in a subject is improving wound healing in a subject. The present invention provides a method for improving wound healing in a subject which comprises administering to the subject a therapeutically effective amount of an agent which inhibits binding of advanced glycation endproducts (AGEs) to a receptor for advanced glycation endproducts (RAGE), over a sufficient period of time in a sufficient amount so as to improve wound healing in the subject.

The present invention provides a method for alleviating inflammation in a subject which comprises administering a therapeutically effective amount of an agent which inhibits binding of advanced glycation endproducts to any receptor for advanced glycation endproducts so as to treat symptoms of inflammation in the subject.

There may be other mechanisms by which soluble RAGE may improve inflammation in a subject. Soluble RAGE may have other effects, such as anti-inflammatory effects that are at least in part, independent of binding up AGE's and interfering with their ability to activate cellular RAGE.

The mechanism of reducing inflammation in the subject may be biochemical in nature or competitive in nature.

As used herein "AGE" means an advanced glycation endproduct; "RAGE" means a receptor for an advanced glycation endproduct; "sRAGE" means a soluble form of a receptor for an advanced glycation endproducts, such as the extracellular two-thirds of the RAGE polypeptide.

In the practice of the methods of the invention a "therapeutically effective amount" is an amount of an agent which is capable of inhibiting the binding of AGE to any receptor for advanced glycation endproduct (RAGE). Accordingly, the effective amount will vary with the subject being treated, as well as with the type of inflammation to be treated. For the purposes of this invention, the methods of administration are to include, but are not limited to, administration cutaneously, subcutaneously, intravenously, parenterally, orally, topically, or by aerosol.

Portions of the agent of the invention may be "labeled" by association with a detectable marker substance (e.g., radiolabeled with 125I or biotinylated) to provide reagents useful in detection and quantification of such agent or its receptor bearing cells or its derivatives in solid tissue and fluid samples such as blood, serum, cerebral spinal fluid or urine.

Compositions

The present invention provides compositions consisting essentially of an agent which reduces inflammation and a carrier. The agent may be an inhibitor of the interaction between RAGE and AGEs. The agent may be an inhibitor of the binding activity of RAGE.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of improving wound healing in a subject may be delivered in a microencapsulation device so as to reduce or prevent a host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

The invention also provides a kit which comprises a therapeutic amount of an agent, which agent is capable of inhibiting binding of advanced glycation endproducts to a receptor for advanced glycation endproducts, over a sufficient period of time in a sufficient amount so as to treat chronic symptoms of diabetes in the subject. A kit may include a composition which includes sRAGE or a portion thereof in a form which is previously dose regulated and time regulated so that a subject may easily take such therapeutic at home or away from a clinical setting. The kit also includes a means for administering the agent to the subject.

This invention is illustrated in the Experimental Details section which follows. These sections are set forth to aid in

EXPERIMENTAL DETAILS

Example 1

Treating Wound Healing as an Example of Treating Inflammation

Improved Wound Healing in Diabetic Mice by Treatment with the Soluble Receptor for Advanced Glycation Endproducts (sRAGE)

Ineffective healing of wounds is a serious problem in diabetes, contributing to increased morbidity (Reynolds, 1985; Galloway and Shuman, 1963; and Pearl and Kanat, 1988). The reparative response in wound healing is orchestrated by multiple cellular elements which work together in many ways, including infiltration of the lesion by inflammatory effector cells. Subsequent to this, fibroblastic elements together with inflammatory effector cells provide antibacterial mechanisms and promote removal of necrotic tissue, as well as laying down of new connective tissue. A fundamental disorder of glucose metabolism might perturb these complex and interactive protective processes. Previous work has suggested that cellular dysfunction in diabetic wound healing involves defective neutrophil function (Bagdade et al., 1978; Nolan et al., 1978; and Mowat and Baum, 1971), delayed infiltration of the wound with inflammatory cells (Greenhalgh et al., 1990 and Fahey et al., 1991), decreased production of collagen (Goodson and Hunt, 1977 and Goodson and Hunt, 1986), and diminished activity of endogenous growth factors, such as basic fibroblast growth factor (Giardino et al., 1994), which could provide a basis for the slower formation of granulation tissue and wound closure.

Defective wound healing in diabetes continues to be an important cause of morbidity in the postoperative period, following trauma, and in the repair of cutaneous lesions. Advanced Glycation Endproducts (AGEs) are the result of nonenzymatic glycation/oxidation of proteins/lipids. Accelerated formation and accumulation of AGEs in tissues of patients with diabetes has been linked, in certain situations, to the development of secondary complications. An important means by which AGEs perturb homeostatic processes is through their interaction with cellular binding sites; the best characterized of these is Receptor for AGE or RAGE, an immunoglobulin superfamily molecule expressed by endothelium, monocytes, and smooth muscle cells, as well as mesangial cells and neurons. AGE engagement of RAGE leads to endothelial activation, with expression of adhesion molecules, enhanced procoagulant properties, and diminished barrier function; and perturbation of monocytes, with changes in cell motility and activation, resulting in expression of proinflammatory cytokines. The interaction of AGEs with RAGE-bearing cells, especially endothelium and mononuclear phagocytes, may promote chronic cellular activation thereby preventing optimal wound healing as reflected by formation of granulation tissue and new connective tissue. The data herein are consistent with this concept: using a secondary intention wound model in diabetic mice, wound closure is enhanced following administration of soluble(s) RAGE, the extracellular domain of the receptor. These experiments contribute to a long-term goal and long-felt need, understanding the contribution of cellular interactions of AGEs in the pathogenesis of diabetic complications.

Poor wound healing in diabetes is likely to be a manifestation of a basic defect in the host inflammatory-reparative response, in addition to possible underlying vascular insufficiency. Exposure of macromolecules to aldose sugars results in nonenzymatic glycation and oxidation (Baynes, 1991; Sell and Monnier, 1989; Ruderman et al., 1992; and Vlassara et al., 1994), initially the reversible early glycation adducts, Schiff bases and Amadori products, form. Following further complex molecular rearrangements, the irreversible AGEs come about. The latter comprise a heterogenous group of structures characterized by fluorescence, propensity to form cross-links, generation of reactive oxygen intermediates (ROIs) and interaction with cellular receptors, the best characterized of which is Receptor for AGE, or RAGE (Schmidt et al., 1992; Neeper et al., 1992; and Schmidt et al., 1994a). AGEs accumulated in the tissues in diabetes influence end-organ function by two general mechanisms: directly, via effects on tissue architecture, consequent to the formation of cross-links and trapping of plasma proteins, and indirectly, by interaction with cellular elements, such as endothelial cells (Ecs) mononuclear phagocytes (Mps), central to homeostasis as well as the host response to pathophysiologically relevant stimuli.

Studies have suggested that the extracellular two-thirds of the molecule, soluble or sRAGE, appeared to be able to inhibit the interaction of circulating AGEs with cellular surfaces (Schmidt et al., 1994b). For example, binding of radiolabelled AGE albumin, a prototypic ligand developed in the laboratory, to cultured endothelial cells or peripheral blood-derived mononuclear phagocytes, was inhibited in the presence of increasing doses of sRAGE. In vivo, clearance of radiolabelled AGE albumin from the circulation of a normal mouse after intravenous injection, was delayed upon treatment with sRAGE. Extrapolation of these findings was attempted to the setting of wound healing. The goal in these studies was to assess the role of AGE-RAGE interaction in the setting of the host response to wounding.

In order to assess the contribution of AGE-RAGE interaction to defective wound healing in diabetes, the wound healing response in diabetic was compared to normal animals, and to determine if blockade of RAGE would ameliorate wound closure in diabetes. In these studies, it was found that administration of soluble RAGE improved wound healing in genetically-diabetic mice. These data support the hypothesis that RAGE blockade may represent a feasible target for intervention in diabetic wound healing as well as other complications of diabetes, such as renal, retinal, neurological, cardiovascular, cerebrovascular and peripheral vascular diseases. Diabetic subjects experience increased restenosis and local problems after angioplasty which suggests that soluble RAGE may be beneficial in reducing restenosis after balloon/stent injury.

Materials and Methods

Murine model of diabetes. A genetic model of insulin-resistant/hyperglycemic diabetes (db+/db+ mice) due to an autosomal recessive trait (chromosome 4) which results in abnormalities of glucose metabolism and obesity in homozygote mice was employed. Heterozygote mice (db+/+m) do not develop these abnormalities, and are employed as controls (Coleman, 1982 and Wyse and Dulin, 1970). Diabetic animals are hyperglycemic (glucose>400 mg/dl by age 3 months), and develop abnormalities similar to human complications, including a defective wound repair. Life expectancy of homozygote mice is 6–8 months. Wounding studies began when mice reached 8 weeks of age, as AGEs are present by that time.

Model of wound healing. For analysis of wound healing in diabetes, a secondary intention wound model was employed (Greenhalgh et al., 1990), as it stimulates, in part, the clinical situation following breakdown of skin in an ulcerated area. A full-thickness 1.5×1.5 cm wound was created on the back of the mouse which was subsequently covered by TEGADERM (clear, plastic closure). The initial area of the wound was measured by placing a sterile glass slide over the area, and tracing the edges of the wound. The area was then determined by using a computer program (NIH Image 157). Serial measurement of the wound dimensions were made on days 3, 5, 7, 10, 14 and 17. This data, consistent with those of previous studies (Greenhalgh et al., 1990), showed significant delay of wound repair in the diabetic mouse especially within the first 2–3 weeks after creation of the wound. Animals in each group were sacrificed at days 17 for analysis. Studies began when mice reached 8–10 weeks of age. In certain experiments, mice were treated with soluble RAGE (the extracellular two-thirds of the molecule) under the TEGADERM on days 3 through 9 after the initial wounding procedure.

Immunohistochemistry for Detection of Advanced Glycation Endproducts.

At the time of the wounding procedure, 1.5×1.5 cm wounds were excised, fixed in formalin (10%) and then processed for immunohistochemistry using affinity-purified anti-AGE IgG (Miyata et al., 1996).

Results

Figure 1:
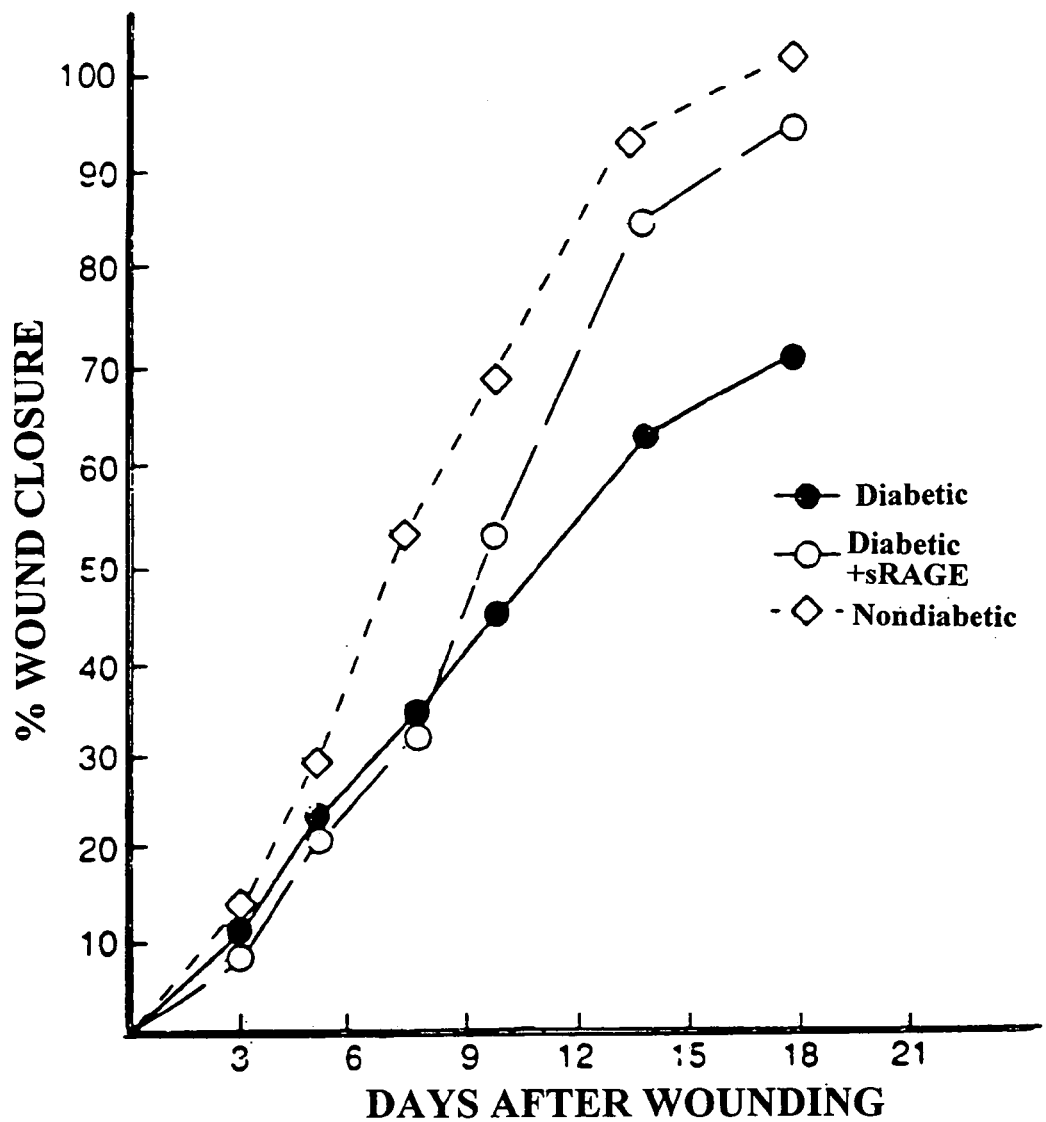
FIG. 1. Effect of sRAGE on wound healing in the genetically-diabetic db+/db+ mouse. A full-thickness 1.5×1.5 cm wound was created on the backs of db+/db+ mice or control, heterozygote db+/m+ mice and covered with TEGAD-ERM®. Diabetic wounds were treated with either phosphate-buffered saline (PBS) directly under the TEGAD-ERM® daily for 7 days commencing on day 3 following surgery or with sRAGE (200 ng). Wound area was measured at baseline through day 21 by placing a glass slide over the wound area, tracing the wound area, and placing this information into a computer in order to calculate the percentage of wound closure as a function of time. Left axis represents percent wound closure.

In order to understand the role of PAGE in diabetic wound healing, 1.5×1.5 cm wounds were created on the backs of db+/db+ or db+/m+ mice. It was first determined that there was no statistically-significant difference in original wound area among the groups of mice receiving the various treatment regimens. When sRAGE (200 ng/day) was administered under the TEGADERM daily from days 3 through 9, the wound healing observed in diabetic mice was significantly enhanced compared with diabetic mice treated with vehicle (phosphate buffered saline; p<0.05; FIG. 1). Furthermore, the healing observed in diabetic mice treated with sRAGE approximated that observed in control, db+/m+ mice treated with vehicle (differences were not statistically significant). (FIG. 1).

Figure 2:
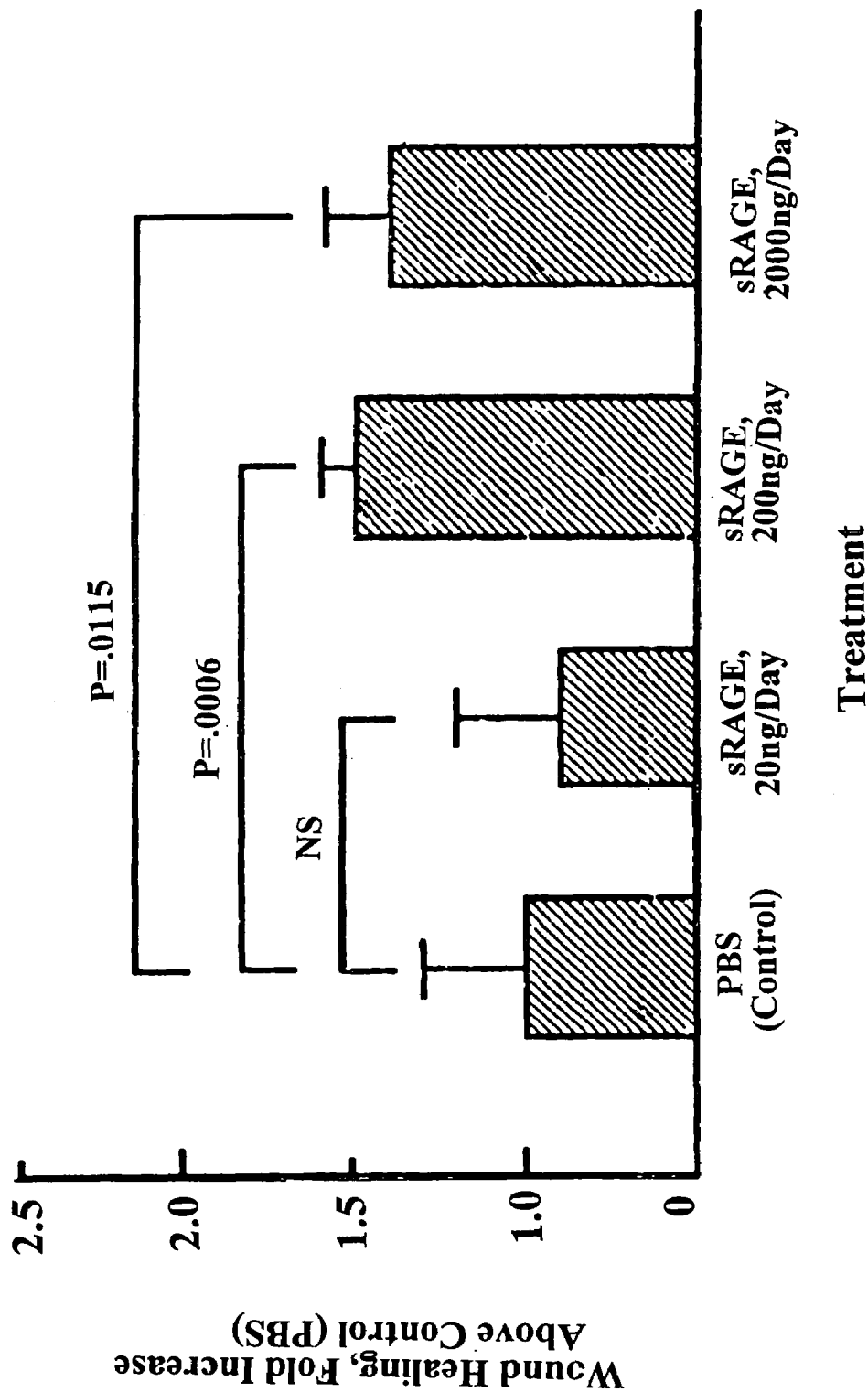
FIG. 2. Administration of sRAGE to the genetically-diabetic db+/db+ mouse improves wound healing: dose-response studies. Wounds were created as above and treated from days 3 through 9 with sRAGE (either 2,000, 200, or 20 ng/day) or with phosphate-buffered saline. At day 10, wound area was measured and compared with initial wound area as above. Results are presented as fold increase in percent wound healing compared with mice treated with phosphate buffered saline (defined as one in figure). All statistical analyses are shown comparing wound healing in the presence of different doses of sRAGE vs. treatment of diabetic wounds with phosphate-buffered saline.

Consistent with the hypothesis that these findings were due to receptor-mediated mechanisms, dose-response studies revealed that there was no enhancement of diabetic wound healing upon administration of sRAGE, 2,000 ng/day, compared with a daily dose of 200 ng/day (differences were not significant; FIG. 2). However, consistent with the studies described herein in diabetic mice, treatment with either 200 or 2,000 ng/day sRAGE (administered on days 3 through 9) was significantly superior to treatment of these mice with phosphate buffered saline when the final wound area was measured on day ten after creation of the wound (FIG. 2). However, at a daily dose of sRAGE of 20 ng/day, there was no significant difference in wound healing in the diabetic mice receiving sRAGE versus those diabetic mice receiving vehicle. (FIG. 2).

Figures 3A, 3B:
FIGS. 3A and 3B. AGE-immunoreactive epitopes in the wounds of diabetic (db+/db+) mice. 1.5×1.5 cm full-thickness wounds created in the backs of diabetic mice(db+/db+ mice.

In order to determine if diabetic wounds were enriched in AGE-immunoreactive material, immunohistochemistry was performed of diabetic versus control mice wounds using affinity-purified anti-AGE IgG. These studies demonstrated that there was a significant increase in AGE-reactive material in the wound tissue of the diabetic mice (FIG. 3A) compared with the nondiabetic control animals (FIG. 3B).

Discussion

The results of these studies indicate that in diabetic tissue such as wounds, there is increased deposition/formation of AGEs. Such AGEs, upon interaction with their cellular receptor RAGE, result in the generation of a sustained inflammatory environment in which healing and quiescence of the potent effector cells and mediators is markedly delayed. It was hypothesized that interference with AGE-RAGE interaction might result in accelerated healing. In these studies, it was demonstrated that local administration of soluble RAGE improved diabetic wound healing in a dose-dependent manner. The specific mechanisms which underlie the efficacy of administration of sRAGE is important. It is possible that administration of sRAGE improves any one of a number of important steps in physiologic wound healing such as inflammation, angiogenesis and/or formation and deposition of new granulation tissue, specifically collagen.

Taken together, these data suggest that in an AGE-enriched environment such as that observed in diabetes, interference with AGE-cellular RAGE interaction might result in amelioration of the chronic complications of diabetes. Given that RAGE is expressed in the endothelium and smooth muscle of the vasculature, in mesangial cells, in certain neural and vascular cells of the retina, and in certain neurons of both the central and peripheral nervous systems as well as other cells, it is likely that blockade of cellular RAGE might result in improved diabetic complications that might otherwise lead to heart attacks, stroke, peripheral vascular disease, amputation of the extremities, kidney disease/failure, blindness, impotence and neuropathy. RAGE is found in monocytes and macrophages and may be present in other cell types wherein therapeutic intervention may also be possible. The present studies support the concept that administration of sRAGE (or other forms of RAGE blockade; such as recombinant sRAGE, RAGE-based peptides, anti-RAGE IgG or anti-RAGE F(ab')$_2$) might present a novel form of therapeutic intervention in this chronic, debilitating disorder.

REFERENCES FOR EXAMPLE 1

Bagdade, J. et al. (1978) Impaired granulocyte adherence. A reversible defect in host defense in patients with poorly controlled diabetes. Diabetes 27:677–681.

Baynes, J. (1991) Role of oxidative stress in development of complications in diabetes. Diabetes 40:405–412.

Coleman, D. (1982) Diabetes-obesity syndromes in mice. Diabetes 31 (Suppl.):1–6.

Fahey, T. et al. (1991) Diabetes impairs the late inflammatory response to wound healing. Surg. Res. 50:308–313.

Galloway, J. and Shuman, D. (1963) Diabetes and Surgery. Am. J. Med. 34:177–191.

Giardino, I. et al. (1994) Nonenzymatic glycosylation in vitro and in bovine endothelial cells after basic fibroblast growth factor activity. J. Clin. Invest. 94:110–117.

Goodson, W. and Hunt T. (1977) Studies of wound healing in experimental diabetes mellitus. J. Surg. Res. 22:221–227.

Goodson, W. and Hunt T. (1986) Wound collagen accumulation in obese hyperglycemic mice. Diabetes 35:491–495.

Greenhalgh, D. et al. (1990) PDGF and FGF stimulate wound healing in the genetically diabetic mouse. Am. J. Pathol. 136:1235–1246.

Mowat, A. and Baum, J. (1971) Chemotaxis of polymorphonuclear leukocytes from patients with diabetes mellitus. NEJM 284:621–627.

Neeper, M. et al. (1992) Cloning and expression of RAGE: a cell surface receptor for AGEs. J. Biol. Chem. 267: 14998–15004.

Nolan, C. et al. (1978) Further characterization of the impaired bactericidal function of granulocytes in patients with poorly controlled diabetes. Diabetes 27:889–894.

Pearl, S. and Kanat, I. (1988) Diabetes and healing: a review of the literature. J. Foot Surg. 27:268–273.

Reynolds, C. (1985) Management of the diabetic surgical patient. A systematic but flexible plan is the key. Postgrad. Med. 77:265–279.

Ruderman, N. et al. (1992) Glucose and diabetic vascular disease. FASEB J. 6:2905–2914.

Schmidt, A-M et al. (1994a) Cellular receptors for AGEs. Arterioscler. Thromb. 14:1521–1528.

Schmidt, A-M. et al. (1994b) RAGE has a central role in vessel wall interactions and gene activation in response to AGESs. PNAS, USA 91:8807–8811.

Schmidt, A-M et al. (1992) Isolation and characterization of binding proteins for AGEs from lung tissue which are present on the endothelial surface. J. Biol. Chem. 267: 14987–14997.

Sell, D. and Monnier, V. (1989) Structure elucidation of senescence cross-link from human extracellular matrix. J. Biol. Chem. 264:21597–21602.

Vlassara, H. et al. (1994) Pathogenic effects of AGEs: biochemical, biologic, and clinical implications for diabetes and aging. Lab. Invest. 70:138–151.

Wyse, B. and Dulin, W. (1970) The influence of age and dietary conditions on diabetes in the Db mouse. Diabetologia 6:268–273.

Example 2

Treating Periodontal Disease as an Example of Treating Inflammation sRAGE Suppresses Accelerated Periodontal Disease in Diabetic Mice.

A model of accelerated periodontal disease in diabetic mice and the effects of sRAGE were studied. Efficacy of sRAGE is shown in diabetic (streptozotocin C57BL6/J mice). Administration of soluble RAGE (full-length extracellular form of approximately 40 kDa) inhibits accelerated alveolar bone loss, which is the hallmark of periodontal disease.

Intraperitoneal injection of soluble RAGE suppresses bone loss in diabetic mice (db+/db+).

Administration of Soluble (s) RAGE Suppresses Alveolar Bone Loss in a Murine Model of Accelerated Periodontal Disease in Diabetes.

Diabetes was induced in C57BL6/J mice by administration of streptozotocin. Diabetes was defined as two serial measurements of serum glucose≧300 mg/dl. Alternatively, an equal number of mice were treated with vehicle for streptozotocin, phosphate buffered saline. One month after induction of diabetes, mice were treated every other day for four consecutive days with oral/anal administration of the human periodontal pathogen, *Porphyromonas gingivalis* (Pg) or vehicle, phosphate-buffered saline. Two months later, mice were sacrificed and decapitated. The mandibles were isolated and, under a dissecting microscope (Olympus), and using curved microdissecting forceps (2 ¾ inches, 0.6 mm wide) and a scalpel with a No. 15C blade, the lingual gingival tissue from the posterior area of each quadrant was dissected. Beginning with a horizontal sulcular incision at the gingival margin of the posterior teeth, the gingiva was reflected (full thickness) with the scalpel blade. Vertical release incisions were made and the tissue was removed (separating the tissue with a horizontal incision just below the mucogingival junction). Tissue was then placed in formalin (10%) for further analysis.

After the above procedures, mandibles were exposed to KOH (2%) for three days and then mechanically defleshed. The jaws (exposure of the lingual surfaces of each ½ mandible) were then embedded in lab putty. In order to remove angulation as a variable, the buccal and lingual cusps of the posterior teeth in the ½ mandible were superimposed during embedding and viewed from the lingual surface prior to photography. The defleshed jaws were photographed using the magnifying dissecting microscope and Ektachrome® 160T film (color slides).

These slides, at a magnification of 40×, were then magnified further 4×. Images were then traced onto standard tracing paper. For each mouse, a total area of the distance between the cemento-enamel junction (CEJ) and alveolar bone crest (BC) for a total of 6 posterior teeth was measured by scanning the tracing into a Macintosh® computer/scanner and the images analyzed using the program NIH Image 157® (along with Adobe Photoshop® photography program). Total area (in arbitrary pixel units) is reported for each mouse (6 teeth) as indicated in FIG. 4. Statistical analysis was performed using one way analysis of variance. At two months, a significant 1.55-fold increase in alveolar bone loss was observed in diabetic mice compared with nondiabetic controls (see specific data below). Similar results were observed in db+/db+ mice (genetically-diabetic/insulin-resistant) one month after infection with Pg compared with nondiabetic controls (m+/db+).

In order to test if administration of sRAGE would ameliorate alveolar bone loss in Pg-treated C57BL6/J mice, certain diabetic mice were treated with sRAGE (MSR; either 35 µg IP/day for two months or 3.5 µg IP/day for two months) Control diabetic mice were treated with equimolar concentrations of mouse serum albumin (70 µg IP/day for two months). All mice were treated with Pg. At the end of that time, measurements of alveolar bone loss were made. The results are as follows:

| | Condition | Alveolar bone loss (CEJ to alveolar BC) |
|---|---|---|
| (I) | Diabetic/albumin | 6,222 ± 406 pixels (SD) |
| (II) | Nondiabetic/albumin | 4,018 ± 501 pixels (SD) |
| (III) | Diabetic/MSR(35 µg/day) | 5,242 ± 463 pixels (SD) |
| (IV) | Diabetic/MSR(3.5 µg/day) | 6,198 ± 427 pixels (SD) |

Many diabetic complications may result from the interaction of AGE's with RAGE to cause cellular perturbation. AGE acts as a ligand for the V-domain of RAGE to mediate such cellular perturbation. This invention provides a method for inhibiting cellular perturbation in a subject associated with a diabetic condition which comprises administering to the subject an amount of an inhibitor of the interation of AGE's with RAGE on the surface of a cell effective to inhibit the interaction and thereby inhibit the cellular perturbation in the subject and treat the diabetic condition.

AGE (advanced glycation endproducts) are a heterogeneous group of compounds. A single or specific pathogenic AGE compound (s) are being identified. Examples of AGEs include but are not limited to: pentosidine (alone or protein-bound modification); carboxymethyllysine (alone or protein-bound modification); carboxyethyllysine (alone or protein-bound modification); pyrallines (alone or protein-bound modification); methylglyoxal (alone or protein-bound modification) and ethylglyoxal (alone or protein-bound modification). One of these AGE's may be a pathogenic ligand for a specific cellular perturbation due to an interaction of the AGE with the V-domain of RAGE. This interaction may be a critical contributory factor in many complications associated with diabetes. This invention provides for inhibitors of such an interaction which may be administered to subjects with diabetic complications.

Cells which may be acted upon by this binding of AGE's to RAGE on the cell surface include endothelial cells, vascular smooth muscle cells, neuronal cells, macrophages, lymphocytes, retinal vascular cells, retinal neuronal cells, mesangial cells and connective tissue cells and cells associated with connective tissue such as cells associated with gingiva and skin. Cells which may be acted upon by this binding of AGE's to RAGE are not limited to this list but may include other cells present in a human body. The present invention provides compounds and compositions which may be useful in inhibiting this interaction, thereby ameliorating the cellular perturbation and ultimately the symptoms associated with diabetes.

Cellular perturbations in those cells that sRAGE, or other peptides or agents provided for by the present invention include but are not limited to: oxidant stress, hyperpermeability, enhanced expression of adhesion molecules such as Vascular Cell Adhesion Moleucle—1; enhanced expression of tissue factor; enhanced macrophage chemotaxis and activation, such as with increased production of cytokines and growth factors; enhanced migration of smooth muscle cells, activation of smooth muscle cells, neuronal oxidant stress and apoptosis. Advanced glycation endproducts (AGE) are the irreversible result of nonenxymatic glycation and oxidation. These AGE's form in the connection with a number of conditions such as: aging, diabetes, inflammation, renal failure, amyloidoses, and hyperlipidemia. AGE's also form in connection with other disease states and abnormal conditions which are not explicitly listed herein but which are encompassed by the present invention.

Therapeutic Agents Identified Through in vitro Means, Are Shown to Be Effective in vivo for Inhibition of Symptoms Associated with Diabetic Complications.

The therapeutic agent identified may be shown to be effective in wound healing. In wound healing experiments, the secondary intention wound model in genetically diabetic mice would be used. The agent (or peptide or pharmaceutical composition) is applied topically to the wounded area, and wound closure (change in wound area), epithelialization and other histologic indices (such as collagen production, extracellular matrix production, fibrin, etc.) is measured. Each of these measurements are indices of the effectiveness of the agent on increasing wound healing.

In periodontal disease, genetically diabetic and streptozotocin-treated mice are utilized as animal model systems to examine bone loss after treatment with peptides having the sequence of Seq I.D. No. 1. Bone loss is measured quantitatively via histological methods and geometrical area determinations. The peptide of Seq. ID No. 1, V-domain peptide, agent or pharmaceutical composition is administered locally (e.g. "painting on" the agent) and/or systemically. Reduced bone loss is an indication of an effective agent.

In accelerated atherosclerosis, streptozotocin-treated apoE "knock-out" mice on a normal chow diet are employed as animal models of this disease condition. The agent (or peptide or pharmaceutical composition) is administered systemically, and quantitative data is gathered by measuring lesion area in the animals after treatment. This data gives an indication of the effectiveness of each agent. The smaller the lesion area as compared to non-treated controls, the more effective the agent.

In diabetic impotence, a rat model with streptozotocin-treated animals is employed in which erections are monitored following administration of apomorphine. The number and frequency of erections is measured in the presence and in the absence of the agent and such data is compared so as to evaluate the effectiveness of the agent to inhibit symptoms of impotence.

In diabetic retinopathy, diabetic rat and mouse models are used as animal model systems to measure changes in blood flow and retinal pathology. Again, the agent (or peptide or pharmaceutical composition) is administered systemically, and quantitative data is gathered by blood flow and qualitative data is gathered by examining retinal pathology in the animals after treatment.

In diabetic nephropathy, diabetic mice and rat models are employed as animal models of diabetic nephropathy. Changes in glomerular filtration rate and renal blood flow are measured in animals given a therapeutic agent and measured in animals given a placebo. In addition, the appearance of protein in the urine and histologic changes in glomeruli are determined in each animal. The effectiveness of the agent is evaluated based upon these measurements in inhibiting diabetic nephropathy.

In diabetic neuropathy, genetically diabetic mice are utilized as an animal model for the determination of the effectiveness of the agent of the present invention. The mice are treated with the compound systemically. The mice are then observed to determine changes in nerve conduction velocity and changes in the number of myelinated peripheral nerve fibers. Such data compared with equivalent measurements determined in an untreated animal will provide an indication of the effectiveness of the agent of the present invention.

REFERENCES FOR EXAMPLE 2

Abraham, C., et al. (1988) Cell 52, 487–501;

Baron et al., Cell, 28, 395–404 (1982);

Baynes, J. Role of oxidative stress in development of complications in diabetes. Diabetes 40:405–412, 1991;

Behl, C., et al. (1994) Cell 77, 817–827;

Breslow. Mouse Models of Atherosclerosis, Science 272: 685 (1996);

Brett, J., Schmidt, A-M., Zou, Y-S, Yan, S-D, Weidman, E., Pinsky, D., Neeper, M., Przysiecki, M., Shaw, A., Migheli, A., and Stern, D., Tissue distribution of the receptor for advanced glycosylation endproducts (RAGE): expression in smooth muscle, cardiac myocytes, and neural tissue in addition to the vasculature. Am. J. Pathol. 143:1699–1712, 1993;

Brownlee, M., Cerami, A., and Vlassara, H. Advanced glycosylation end products in tissue and the biochemical basis of diabetic complication. N. Engl. J. Med. 318: 1315–1320, 1988;

Calligaro, D., et al. (1993) J. Neurochem. 60:2297–2303;

Carpenter, et al. (1971) Toxicol. Appl. Pharmacol., 18:35–40;

Crall F V J and W C Roberts. The extramural and intramural coronary arteries in juvenile diabetes mellitus: analysis of nine necropsy patients aged 19 to 38 years with onset of diabetes before age 15 years. Am. J. Med. 64:221–230, 1978;

Davis, J., et al. (1992) BBRC 189:1096–1100;

Dressman et al., Nature, 295, 185–160 (1982);

Fraser, P., et al. (1992) J. Neurochem. 59:1531–1540;

Fraser, P., et al. (1993) J. Neurochem. 61:298–305;

Ghiso, J., et al. (1993) Biochem. J. 293:27–30;

Gibbons and Szau. Molecular Therapies for Vascular Disease. Science 272:689–693 (1996);

Goedert, M. (1993) Trends Neurosci. 16:460–465;

Haass, C. and Selkoe, D. (1994) Cell 7:1039–1042;

Hamby R I et al. Reappraisal of the role of the diabetic state in coronary artery disease. Chest 2:251–257, 1976;

Harper's Biochemistry, R. K. Murray et al. (Editors) 21st Edition, (1988) Appelton & Lange, East Norwalk, Conn.;

Hensley, K., et al. (1994) PNAS(USA) 91:3270–3274;

Hicks, M., Delbridge, L., Yue, D. And Reeve, R. Catalysis of lipid peroxidation by glucose and glycosylated proteins. Biochem. Biophys. Res. Commun. 151:649–655, 1988;

Joslin, G., et al. (1991) J. Biol. Chem. 266:21897–21902;

Kaiser et al. Science, 223, 249–255 (1984);

Kannel W B and D L McGee. Diabetes and cardiovascular disease: the Framingham study. J. Am. Med. Assoc. 241:2035–2038, 1979;

Kimura, H., and Schubert, D. (1993) PNAS(USA) 90:7508–7512;

Kisilevsky, R., et al. (1995) Nature Med. 1:143–148;

Koh, J-Y., et al. (1990) Brain Res. 533:315–320;

Koo, E., et al. (1993) PNAS(USA) 90:4748–4752;

Kosik, K. (1994) J. Cell. Biol. 127:1501–1504;

Lander, H. L., Tauras, J. M., Ogiste, J. S., Moss, R. A., and A. M. Schmidt. Activation of the Receptor for Advanced Glycation Endproducts triggers a MAP Kinase pathway regulated by oxidant stress. J. Biol. Chem. 272:17810–17814, 1997;

Lerner et al., Cell, 23, 309–310 (1981);

Lerner, Scientific American, 248, 66–74 (1983);

Loo, D., et al. (1993) PNAS(USA) 90:7951–7955;

Manson J E et al. A prospective study of maturity-onset diabetes mellitus and risk of coronary heart disease and stroke in women. Arch. Of. Int. Med. 151:1141–1137, 1991;

Meda, L., et al. (1995) Nature 374, 647–650;

Mitsuhashi, M., et al. (1991) Mol. Brain. Rs. 11:177–180;

Miyata, T.,O. Hori, J. H. Zhang, S. D. Yan, L. Ferran, Y. Iida, and A. M. Schmidt. The Receptor for Advanced Glycation Endproducts (RAGE) mediates the interaction of AGE-$\beta_2$-Microglobulin with human mononuclear phagocytes via an oxidant-sensitive pathway: implications for the pathogenesis of dialysis-related amyloidoses. J. Clin. Invest. 98: 1088–1094, 1996;

Neeper, M., Schmidt, A. M., Brett, J., Yan, S. D., Wang, F., Pan, Y. C., Elliston, K., Stern, D., and Shaw, A. Cloning and expression of RAGE: a cell surface receptor for advanced glycosylation end products of proteins. J. Biol. Chem. 267:14998–15004, 1992;

Park, L., Raman, K. G., Lee, K. J., Lu, Y., Ginsberg, M. D., Ferran, L., Stern, D. and Schmidt, A. M. A murine model of accelerated diabetic atherosclerosis: suppression by soluble receptor for advanced glycation endproducts. Circulation Supplement, 1997;

Pike, C., et al. (1993) Neurosci. 13:1676–1687;

Porte and Schwartz. Diabetes Complications: Why is Glucose Potentially Toxic? Science 272: 699–700 (1996);

Pyorala K M, M Laasko and M Uusitupa. Diabetes and atherosclerosis: an epidemiologic view. Diab. Metab. Rev. 3:463–524, 1987;

Robertson W B and J B Strong. Atherosclerosis in persons with hypertension and diabetes mellitus. Lab. Invest. 18: 538–551, 1968;

Ross et al., Nature, 294, 654–658 (1981);

Ruderman, N., Williamson, J., and Brownlee, M. Glucose and diabetic vascular disease. FASEB J. 6:2905–2914, 1992;

Schmidt, A. M., O. Hori, J. Chen, J. F. Li, J. Crandall, J. Zhang, R. Cao, S. D. Yan, J. Brett and D. Stern. Advanced glycation endproducts interacting with their endothelial receptor induce expression of vascular cell adhesion molecule-1 (VCAM-1): a potential mechanism for the accelerated vasculopathy of diabetes. J. Clin. Invest. 96:1395–1403, 1995;

Schmidt, A. M., Yan, S. D., Brett, J., Mora, R., and Stern, D. Regulation of mononuclear phagocyte migration by cell surface binding proteins for advanced glycosylation endproducts. J. Clin. Invest. 92:2155–2168, 1993;

Schmidt, A. M., Hasu, M., Popov, D., Zhang, J. H., Yan, S. D., Brett, J., Cao, R., Kuwabara, K., Costache, G., Simionescu, N., Simonescu, M., and Stern, D. The receptor for Advanced Glycation Endproducts (AGES) has a central role in vessel wall interactions and gene activation in response to AGEs in the intravascular space. PNAS(USA) 91: 8807–8811, 1994;

Schmidt, A. M., Vianna, M., Gerlach, M., Brett, J., Ryan, J., Kao, J., Esposito, C., Hegary, H., Hurley, W., Clauss, M., Wang, F., Pan, Y. C., Tsang, T. C., and Stern, D. Isolation and characterization of binding proteins for advanced glycosylation endproducts from lung tissue which are present on the endothelial cell surface. J. Biol. Chem. 267:14987–14997, 1992;

Schwarzman, A., et al.(1994) PNAS(USA) 91, 8368–8372;

Sell, D. and Monnier, V. Structure elucidation of a senescence cross-link from human extracellular matrix: implication of pentoses in the aging process. J. Biol. Chem. 264:21597–21602, 1989;

Snow, A., et al. (1994) Neuron 12, 219–234;

Strittmatter, W. (1993a) PNAS(USA) 90, 1977–1981;

Strittmatter, W. (1993b) Exptl. Neurol. 122, 327–334;

Trojanowski, J. and Lee, V. (1994) Am. J. Pathol. 144: 449–453.

Wailer B F et al. Status of the coronary arteries at necropsy in diabetes mellitus with onset after age 30 yrs: analysis of 229 diabetic patients with and without clinical evidence of coronary heart disease and comparison to 183 control subjects. Am. J. Med. 69:498–506, 1980;

Walter et al., Proc. Natl. Acad. Sci. USA, 78, 4882–4886 (1981);

Wautier, J. L., C. Zoukourian, 0. Chappey, M. P. Wautier, P. J. Guillausseau, R. Cao, 0. Hori, D. Stern and A. M. Schmidt. Receptor-mediated endothelial cell dysfunction in diabetic vasculopathy: soluble receptor for advanced glycation endproducts blocks hyperpermeability. J. Clin. Invest. 97:238–243, 1996;

Wishik, C. (1989) Curr. Opin. Cell Biol. 1, 115–122;

Wong et al., Proc. Natl. Sci. USA, 79, 5322–5326 (1982);

Wu, J., Rogers, L., Stern, D., Schmidt, A. M. and Chiu, D. T. W. The soluble receptor for Advanced Glycation Endproducts (sRAGE) ameliorates impaired wound healing in diabetic mice. Abstract booklet, Plastic Surgery Research Council. Abstract #77, p. 43, 1997;

Yan, S. D., Schmidt, A. M. Anderson, G., Zhang, J., Brett, J., Zou, Y. S., Pinsky, D., and Stern, D. Enhanced cellular oxidant stress by the interaction of advanced glycation endproducts with their receptors/binding proteins. J. Biol. Chem. 269:9889–9897, 1994;

Yan, S D, X. Chen, J. Fu, M. Chen, H. Zhu, A. Roher, T. Slattery, M. Nagashima, J. Morser, A. Migheli, P. Nawroth, G. Godman, D. Stern and A. M. Schmidt. RAGE and amyloid-β peptide neurotoxicity in Alzheimer's disease. Nature 382:685–691, 1996;

Yan, S D, Zhu, H., Fu, J., Yan, S. F., Roher, A., Tourtellotte, W., Rajavashisth, T., Chen, X., Stern, D. and Schmidt, A. M. Amyloid-beta peptide-RAGE interaction elicits nauronal expression of M-CSF: a proinflammatory pathway in Alzheimer's disease. Proc. Natl. Acad. Sci. 94:5296–5301, 1997;

Yankner, B., et al. (1990) Science 250:279–282, 1990.

Example 3

Treating Delayed Type Hypersensitivity as an Example of Treating Inflammation

Interaction of EN-RAGE (Extracellular Novel Rage Binding Protein) with Receptor for AGE (RAGE) Perpetuates Inflammatory Responses: Suppression of Delayed-type Hypersensitivity Reactions with Soluble Receptor for Age (sRAGE)

Expression of RAGE, the Receptor for Advanced Glycation Endproducts, is increased in the setting of inflammation. Here we report a new member of the calgranulin family of proinflammatory cytokines called EN-RAGE (or Extracellular Novel RAGE-binding protein), which interacts with RAGE on cells such as endothelial cells, to alter cellular properties in a manner consistent with perturbation. Administration of soluble RAGE (the extracellular ligand binding domain of RAGE; sRAGE) or anti-RAGE or anti-EN-RAGE F(ab')$_2$ fragments markedly attenuated inflammation in a model of delayed hypersensitivity. These data link RAGE to the inflammatory response and identify EN-RAGE and RAGE as novel targets for anti-inflammatory intervention. Soluble RAGE, furthermore, is thus a prototypic structure for the design of a new class of anti-inflammatory agents.

The Receptor for AGE (RAGE) is a member of the immunoglobulin superfamily of cell-surface molecules (1–2). Originally identified and characterized as a cellular receptor for glucose (aldose sugar)-modified proteins, or Advanced Glycation Endproducts (AGEs) (3–13), RAGE has subsequently been reported to interact with other ligands, in both settings of normal development and in Alzheimer's disease (14–16). In normal development, RAGE interacts with amphoterin, a polypeptide which mediates neurite outgrowth in cultured embryonic neurons. In those studies, either anti-RAGE F(ab')$_2$ or soluble RAGE (sRAGE) inhibited neurite outgrowth on amphoterin-coated matrices, but not on matrices coated with other substrates such as laminin or poly-l-lysine (3). In later studies, RAGE was identified as a receptor on neurons and microglia for amyloid-β-peptide, a polypeptide linked to the pathogenesis of neuronal toxicity and death in Alzheimer's disease.

In unpublished observations from our laboratory, we identified that increased RAGE expression was noted in the vascular and inflammatory cells of inflammatory lesions, such as in the kidney tissue from patients with active lupus nephritis (FIG. 5). We therefore hypothesized that RAGE might interact with alternative ligand(s) in that setting in order to, perhaps, participate in the inflammatory response.

Herein, the findings demonstrate that RAGE interacts with a molecule with close homology to calgranulin C. We have termed this molecule, EN-RAGE (Extracellular Novel RAGE binding protein) and show that EN-RAGE:RAGE interaction activates cells such as endothelial cells which are importantly involved in the inflammatory response. In a model of murine delayed hypersensitivity, administration of soluble RAGE (sRAGE), which contains the ligand interaction domain, inhibits the development of cellular activation and inflammation. These findings identify RAGE as a new target for anti-inflammatory intervention.

Materials and Methods

Isolation and Purification of EN-RAGE.

Bovine lung acetone powder (SIGMA®) was subjected to solubilization in buffer containing tris (0.02M, pH 7.4); NaCl (0.15M); octyl-β-glucoside (1%); and protease inhibitors (PMSF and aprotinin). After serial chromatography onto SP sepharose (Pharmacia LKB®), and affi-gel 10 resin (BIO-RAD®) to which had been adsorbed purified soluble human RAGE (prepared from a baculovirus expression system), RAGE-binding proteins were identified based on a screening assay employing immobilized column fraction (Nunc Maxisorp dishes) (NUNC®) and $^{125}$-I-labelled sRAGE as above. After elution with heparin-containing buffer (1 mg/ml), positive fractions were identified. RAGE-binding proteins were subjected to sequence analysis.

Cloning of EN-RAGE. The cDNA for EN-RAGE was cloned from a bovine lung library and placed into a baculovirus expression system. In this system, EN-RAGE, which lacks a leader sequence, was synthesized within Sf9 cells. EN-RAGE was then purified after solubilization of the cells in detergent-containing buffer, and sequential purification on hydroxylapatite and heparin-containing resins. The final product displayed a single band on Coomassie-stained SDS-PAGE gels and was devoid of endotoxin after chromatography onto Detoxi-gel columns (PIERCE®). Absence of detectable endotoxin was confirmed using limulus amebocyte assay (SIGMA®).

Sequence analysis. After SDS-PAGE identified an ≈12 kDa polypeptide with RAGE-binding activity, the gel band was eluted according to previously-published methods (17). The published method was modified by addition of a final wash of two aliquots (0.1 ml each) of guanidine (5.0M), urea (5.0 M), trifluoroacetic acid (0.2%), acetonitrile (10%), and Zwittergent 3-08 (1.0%) (Calbiochem) to ensure that protein was completely washed from the filter. Amino-terminal sequence analysis was performed. Automated Edman degradation was carried out employing an HP-G1005A sequencer (Hewlett Packard Analytical Instruments). In order to obtain internal sequence, the gel bands were treated as above for elution, except that the extraction buffer contained half the usual amount of SDS (1). Endoproteinase Lys-C (1 μg) (Boehringer Mannheim) was added and the sample incubated overnight. The digest was then fractionated by microbore HPLC (Michrom Bioresources) on a 1 mm×50 mm PLRP-S column (Polymer Laboratories, Ltd.). The gradient utilized was 2% per minute from acetonitrile (5–75%) in trifluoroacetic acid (0.1%) and fractions were collected at 30 second intervals. Absorbance was monitored at 214 nm and fractions that corresponded to chromatographic peaks were then subjected to sequence analysis.

Endothelial cell activation. Human umbilical vein endothelial cells were isolated, characterized and maintained as previously described (18). Cells were cultured in serum-free RPMI 1640 without endothelial cell growth factor for 24 hrs and then stimulated with the indicated concentrations of EN-RAGE. Where indicated, cells were pretreated with rabbit anti-human RAGE IgG, nonimmune rabbit IgG; in certain cases, EN-RAGE was pretreated with the indicated concentration of soluble RAGE (sRAGE) for 2 hrs prior to stimulation with EN-RAGE. After eight hrs stimulation with EN-RAGE, cells were fixed with paraformaldehyde (26) for 30 mins, washed twice with PBS, treated with PBS containing non-fat dry milk (5%) and BSA (2.5%) to block non-specific binding sites on the cell surface. Cell surface ELISA employing anti-VCAM-1 IgG (Santa Cruz Biotechnologies, Santa Cruz, Calif.) was performed. Assessment of functional VCAM-1 activity was determined using $^{51}$Cr-labelled Molt-4 cells (ATCC) as previously described (10).

Delayed hypersensitivity model. A murine model of delayed hypersensitivity was established based on previously-published studies (19). Female CF-1 mice (Charles River laboratories), 6 weeks of age, were sensitized by subcutaneous injection over the left inguinal lymph node of an emulsion (0.1 ml) containing methylated BSA (mBSA; 25 mg/ml; SIGMA®), NaCl (0.9%), dextran (5–40×10$^6$ MW; 50 mg/ml; SIGMA®) and Freund's incomplete adjuvant (50%; ICN Biomedical). Three weeks later, the left plantar hind paw was injected subcutaneously with mBSA (0.4 mg/ml; 0.050 ml). Where indicated, mice were pretreated by intraperitoneal injection with sRAGE (indicated dose), mouse serum albumin (SIGMA®), immune or non-immune F(ab')$_2$ fragments (prepared using a kit from Pierce) 24 and 12 hrs prior to, and 6 and 12 hrs after local challenge with mBSA. 24 hrs after injection of foot pad with mBSA, clinical score of foot pad was performed; mice were then humanely sacrificed and feet fixed in formalin (10l) or frozen for further analysis. Histologic score was performed on sections of foot stained with hematoxylin and eosin (SIGMA®). The clinical score was defined as follows (scale; 1–5): 1=no inflammation and thus identical to untreated foot; 2=slight rubor and edema; 3=severe rubor and edema with wrinkling of the skin of the foot pad; 4=severe rubor and edema without wrinkling of the skin of the foot pad; and 5=severe rubor and edema resulting in spreading of the toes. The histologic score after hematoxylin and eosin staining was defined as follows (scale; 1–5): 1=no leukocytic infiltration with slight subcutaneous edema; 2=slight perivascular leukocytic infiltration with slight subcutaneous edema; 3=severe leukocytic infiltration without granulomata; and 4=severe leukocytic infiltration with granulomata.

Results

Identification of EN-RAGE. After a serial series of experiments designed to identify RAGE-binding proteins from bovine lung extract (from where RAGE was originally purified), an ≈12 kDa polypeptide was identified. Upon sequence analysis, this polypeptide was found to bear significant homology to members of the calgranulin C family of proteins (Table 1) (20–21). This class of proteins exist intracellularly within inflammatory cells. Upon release in inflamed loci, we postulated they might be able to, in turn, engage and activate other cells already recruited into the inflammatory response. Thus, this might represent an important means by which the inflammatory response might be propagated and sustained, thereby increasing the probability of cellular injury.

EN-RAGE activates endothelial cells in a RAGE-dependent manner. To test this hypothesis, EN-RAGE was purified as described above and incubated with endothelial cells. Incubation of EN-RAGE with HUVEC resulted in increased cell surface Vascular Cell Adhesion Molecule-1 (VCAM-1) in a RAGE-dependent manner (FIG. 6). These data suggested that in an inflammatory focus, interaction of EN-RAGE with EC RAGE might represent a means by which to further propagate an inflammatory response. Consistent with increased VCAM-1 antigen on the surface of EN-RAGE-treated ECs, increased binding for Molt-4 cells (which bear the ligand for VCAM-1, VLA-4), ensued (FIG. 7). While incubation with either BSA or non-immune IgG did not affect the ability of EN-RAGE to activate EC VCAM-1, incubation with either sRAGE or anti-RAGE F(ab')$_2$ significantly attenuated the ability of EN-RAGE to increase Molt-4 binding to treated HUVEC.

We sought to test these hypotheses in in vivo models. We demonstrated that in diabetic mice, in which the ligand for RAGE is likely to be, at least in part, products of glycation/oxidation of proteins/lipids, the Advanced Glycation Endproducts, or AGEs, administration of the soluble, ligand-binding portion of RAGE (soluble or sRAGE), suppressed accelerated atherosclerosis in diabetic apolipoprotein E null mice (12) and improved wound healing in genetically-diabetic db+/db+ mice (22). Thus, the biologic effects of EN-RAGE in highly-inflammatory foci, such as those characterized by models of granulomatous inflammatory lesions (delayed hypersensitivity), could be suppressed in the presence of sRAGE.

To test this, we studied a model of delayed hypersensitivity (DH) in which mice were first sensitized by injection of methylated BSA (mBSA; which does not bind RAGE) over the inguinal lymph nodes of female CF-1 mice. Three weeks after sensitization, mice were challenged with mBSA by injection into the hind foot pad. An inflammation score was designed on a scale of 1–9 which included both clinical score (1–4) and histologic score (1–5) as indicated in FIG. 8.

Consistent with our hypothesis, administration of sRAGE suppressed inflammation upon injection of mBSA into the foot pad of mice previously-sensitized with mBSA over the lymph nodes, in a dose-dependent manner (FIG. 8). At a dose of 100 μg sRAGE, inflammation was markedly suppressed (p<0.01). In contrast, administration of mouse serum albumin, had no effect on the appearance of the inflammatory lesion (FIG. 8). Consistent with an important role for EN-RAGE and RAGE in the development of inflammation in this model, treatment of the mice with either anti-EN-RAGE F(ab')$_2$ or anti-RAGE F(ab')$_2$ considerably suppressed inflammation (p<0.05 in each case compared with treatment with nonimmune F(ab')$_2$. When mice were treated with both anti-EN-RAGE and anti-RAGE F(ab')$_2$, even further suppression of the inflammatory response eventuated (p<0.05 compared with treatment with nonimmune F(ab')$_2$ (FIG. 8).

Discussion

The inflammation phenotype observed in delayed-type hypersensitivity reactions certainly represent the culmination of a complex interplay and contribution of multiple cell types and their cellular mediators. In the development of inflammation, an important source of the stimuli may be from the inflammatory cells themselves. Upon initial recruitment into an inflammatory locus, cells such as neutrophils and macrophages may release mediators such as those of the calgranulin family, including EN-RAGE, and propagate and sustain the inflammatory response. Such mediators, such as EN-RAGE, likely require cellular receptors to initiate events that will culminate in altered gene expression.

Our data strongly suggest that EN-RAGE-RAGE interaction is an important factor in these processes. Nearly complete suppression of inflammation was noted in the presence of sRAGE, in a dose-dependent manner. Based upon our studies, sRAGE may act as a decoy in this setting to bind EN-RAGE prior to its ability to engage RAGE-bearing cells implicated in the inflammatory response. Furthermore, in the presence of anti-RAGE/anti-EN-RAGE or anti-RAGE+anti-EN-RAGE F(ab')$_2$, substantial suppression of inflammation was observed, further indicating a role of these factors in the modulation of the inflammatory response.

It is important to note, of course, that alternate mechanisms underlying the beneficial effects of sRAGE may be operative in these settings. However, the studies noted above employing the indicated F(ab')$_2$ fragments, strongly implicate EN-RAGE and RAGE in the evolution of the inflammatory response in this setting.

In conclusion, the studies presented herein implicate RAGE centrally in the inflammatory response and identify soluble RAGE as a prototypic structure for the development of novel, anti-inflammatory agents.

Note: FIG. 9 shows the nucleic acid sequence (cDNA sequence) of bovine EN-RAGE.

EN-RAGE (Extracellular Novel-RAGE Binding Protein) Activated Endothelial Cells to Mediate Inflammatory Responses.

The expression of Receptor for AGE (RAGE) is enhanced in inflammatory settings such as atherosclerosis and autoimmune vasculitities. We hypothesized that Receptor for AGE (RAGE) might interact with alternative ligands beyond Advanced Glycation Endproducts (AGES) in such settings. We isolated and purified an ≈12 kDa polypeptide from extract of bovine lung which bore homology to the calgranulin family of proinflammatory mediators. This polypeptide, called EN-RAGE, binds immobilized RAGE and endothelial (EC)/macrophage (MP) RAGE in culture wells with Kd ≈75 nM, processes blocked in the presence of anti-RAGE IgG or soluble (sRAGE; the extracellular two-thirds of RAGE). In vitro, exposure of cultured ECs to EN-RAGE increased activation of NF-kB, expression of cell-surface VCAM-1 (4.3-fold compared to treatment with bovine serum albumin BSA), and adhesion of Molt-4 cells (which bear VLA-4, the counter-ligand for VCAM-1) (7-fold compared with BSA), all in a manner inhibited in the presence of anti-RAGE IgG or sRAGE. Exposure of macrophages to EN-RAGE resulted in increased chemotaxis in a RAGE-dependent manner. To test these concepts in vivo, we utilized a model of delayed hypersensitivity in mice in which footpad injections of methylated BSA (mBSA) induce localized inflammation. Pre-treatment (intraperitoneal; IP) with sRAGE prevented mESA-mediated inflammation in a dose-dependent manner. At 100 µg IP sRAGE, the mBSA-treated foot manifested no inflammation and markedly diminished activation of NF-kB compared with mice treated with vehicle, mouse serum albumin (MSA); further, elaboration of TNF-alpha into the serum was com-

TABLE 1

Sequence analysis of EN-RAGE and comparison with related proteins.

```
                    1              10             20             30
EN-RAGE         T K L E D H L E G I I N I G H Q Y S V R V G H F D T L N K Y
N-TERM
Endo Lys C
B—COAg          T K L E D H L E G I I N I F H Q Y S V R V G H F D T L N K R

B—CAAFI         T K L E D H L E G I I N I F H Q Y S V R V G H F D T L N K R 31             40             50             60
EN-RAGE         E L K Q L G T K E L P K T L Q N   K D Q
N-TERM
Endo Lys C B—COAg          E L K Q L I T K E L P K T L Q N T K D Q P T I D K I F Q D L

B—CAAFI         E L K Q L I T K E L P K T L Q N T K D Q P T I D K I F Q D L 61             70             80             90
EN-RAGE
N-TERM
Endo Lys C              D G A V S F E E F V V L V S R V L K B—COAg          D A D K D G A V S F E E F V V L V S R V L K T A H I D I H K

B—CAAFI         D A D K D G A V S F E E F V V L V S R V L K T A H I D I H K (SEQ ID NOS:9, 10, 11, 12, respectively).
``` pletely prevented. Partial anti-inflammatory responses were observed upon treatment of the mice with either anti-RAGE or anti-EN-RAGE F(ab')2. Nonimmune F(ab')2 was without effect. Taken together, these findings indicate that ligands alternative to AGEs such as EN-RAGE activate ECs and MPs, thereby linking RAGE to the generalized inflammatory response.

sRAGE Results in Diminished Mortality After Endotoxemia: A Potential Treatment for Septic Shock The use of sRAGE or compounds which are capable of inhibiting the interaction of EN-RAGE and RAGE could be useful agents for the treatment of septic shock or sepsis in subjects. It has been shown that a subject given lethal doses of LPS has reduced mortality when the LPS is given in the presence of sRAGE.

sRAGE and Endotoxemia

Soluble Receptor for AGE (sRAGE) has been shown to prevent inflammation in a model of delayed-type hypersensitivity. Unlike certain anti-inflammatory-type agents, it was believed that sRAGE might exert beneficial effects when administered in the setting of endotoxemia, a prototypic result of, for example, profound gram negative bacteremia.

When uniformly lethal doses of LPS were administered to Balb/C mice (≈750 μg), administration of sRAGE (pre or post LPS injection) prevented death in ≈50% of the mice in pilot studies.

These data underscore the proposition that the potent anti-inflammatory effects of sRAGE are not associated with an untoward inclination toward morbidity/mortality due to the presence of septicemia/endotoxemia. SRAGE, therefore, may be a selective anti-inflammatory agent with selective protective effects against maladaptive inflammatory responses.

REFERENCES FOR EXAMPLE 3

1. Schmidt, A. M., Vianna, M., Gerlach, M., Brett, J., Ryan, J., Kao, J., Esposito, C., Hegarty, H., Hurley, W., Clauss, M., Wang, F., Pan, Y. C., Tsang, T. C., and Stern, D. Isolation and characterization of binding proteins for advanced glycosylation endproducts from lung tissue which are present on the endothelial cell surface. J. Biol. Chem. 267:14987–14997, 1992.
2. Neeper, M., Schmidt, A. M., Brett, J., Yan, S. D., Wang, F., Pan, Y. C., Elliston, K., Stern, D., and Shaw, A. Cloning and expression of RAGE: a cell surface receptor for advanced glycosylation end products of proteins. J. Biol. Chem. 267: 14998–15004, 1992.
3. Schmidt, A-M, Hori, O, Brett, J, Yan, S-D, Wautier, J-L, and Stern D. Cellular receptors for advanced glycation end products. Arterioscler. Thromb. 14:1521–1528, 1994.
4. Schmidt, A. M., S D Yan, and D. Stern. The Dark Side of Glucose (News and Views). Nature Medicine 1:1002–1004, 1995.
5. Yan, S-D, Schmidt, A-M, Anderson, G, Zhang, J, Brett, J, Zou, Y-S, Pinsky, D, and Stern, D. Enhanced cellular oxidant stress by the interaction of advanced glycation endproducts with their receptors/binding proteins. J. Biol. Chem. 269:9889–9897, 1994.
6. Schmidt, A-M, Yan, S-D, Brett, J, Mora, R, Nowygrod, R, and Stern D. Regulation of mononuclear phagocyte migration by cell surface binding proteins for advanced glycosylation endproducts. J. Clin. Invest. 92:2155–2168, 1993.
7. Wautier, J L, Chappey, O, Wautier, M P, Hori, O, Stern, D, and Schmidt A M. Receptor-mediated endothelial dysfunction in diabetic vasculopathy: sRAGE blocks hyperpermeability. J. Clin. Invest. 97:238–243, 1996.
8. Miyata, T., Hori, O, Zhang, J H, Yan, S D, Ferran, L, Iida, Y, and Schmidt, A M. The Receptor for Advanced Glycation Endproducts (RAGE) mediates the interaction of AGE-b$^2$-Microglobulin with human mononuclear phagocytes via an oxidant-sensitive pathway: implications for the pathogenesis of dialysis-related amyloidosis. J. Clin. Invest. 98:1088–1094, 1996.
9. Schmidt, A-M, Hasu, M, Popov, D, Zhang, J-H, Chen, J, Yan, S-D, Brett, J, Cao, R, Kuwabara, K, Gabriela, C, Simionescu, N, Simionescu, M, and Stern D. Receptor for advanced glycation endproducts (AGEs) has a central role in vessel wall interactions and gene activation in response to circulating AGE proteins. PNAS(USA) 91:8807–8811, 1994.
10. Schmidt, A M, Hori, O, Chen, J, Brett, J, and Stern, D. AGE interaction with their endothelial receptor induce expression of VCAM-1: a potential mechanism for the accelerated vasculopathy of diabetes. J. Clin. Invest. 96:1395–1403, 1995.
11. Lander, H. L., Tauras, J. M., Ogiste, J. S., Moss, R. A., and A. M. Schmidt. Activation of the Receptor for Advanced Glycation Endproducts triggers a MAP Kinase pathway regulated by oxidant stress. J. Biol. Chem. 272:17810–17814, 1997.
12. Park, L., Raman, K. G., Lee, K. J., Yan, L., Ferran, L. J., Chow, W. S., Stern, D., and Schmidt, A. M. Suppression of accelerated diabetic atherosclerosis by soluble Receptor for AGE (sRAGE). Nature Medicine 4:1025–1031, 1998.
13. Wautier J L, Chappey O, Wautier M P, Boval B, Stern D and AM Schmidt. Interaction of diabetic erythrocytes bearing advanced glycation endproducts with the endothelial receptor RAGE induces generation of reactive oxygen intermediates and cellular dysfunction. Circ. 94 (8):#4139, 1996.
14. Hori, O., J. Brett, T. Slattery, R. Cao, J. Zhang, J. Chen, M. Nagashima, D. Nitecki, J. Morser, D. Stern, A. M. Schmidt. The Receptor for Advanced Glycation Endproducts (RAGE) is a cellular binding site for amphoterin: mediation of neurite outgrowth and co-expression of RAGE and amphoterin in the developing nervous system. J. Biol. Chem. 270:25752–25761, 1995.
15. Yan, S D, X. Chen, J. Fu, M. Chen, H. Zhu, A. Roher, T. Slattery, M. Nagashima, J. Morser, A. Migheli, P. Nawroth, G. Godman, D. Stern, and A. M. Schmidt. RAGE and amyloid-b peptide neurotoxicity in Alzheimer's disease. Nature 382:685–691, 1996.
16. Yan, S-D., Zhu, H., Fu, J., Yan, S-F., Roher, A., Tourtellotte, W., Rajavashisth, T., Chen, X., Stern, D. and Schmidt, A-M. Amyloid-beta peptide-RAGE interaction elicits neuronal expression of M-CSF: a proinflammatory pathway in Alzheimer's disease. Proc. Natl. Acad. Sci. 94:5296–5301, 1997.
17. Slattery, T. K. and Harkins, R. N. Techniques in protein chemistry IV, ed. Angeletti, R. H., Academic Press, San Diego, Calif., 1992.
18. Jaffe, E., Nachman, R., Becker, C., and Minick, R. Culture of human endothelial cells derived from umbilical veins. Identification by morphologic and immunologic criteria. J. Clin. Invest. 52:2745–2756, 1973.
19. Dunn, C. J., Galinet, L. A., Wu, H., Nugent, R. A., Schlachter, S. T., Staite, N. D., Aspar, D. G., Elliott, G. A., Essani, N. A., Rohloff, N. A., and Smith, R. J. Demonstration of novel anti-arthritic and anti-inflammatory effects of diphosphonates. J. Pharmacology and Experimental Therapeutics 266: 1691–1698, 1993.
20. Wicki, R., Marenholz, I., Mischke, D., Schafer, B. W., and Heizmann, C. W. Characterization of the human S100A12 (calgranulin C, p6, CAAF1, CGRP) gene, a new member of the S100 gene cluster on chromosome 1q21. Cell Calcium 20:459–464, 1996.
21. Dell'Angelica, E. C., Schleicher, C. H., and Santome, J. A. Primary structure and binding properties of calgranulin C, a novel S100-like calcium-binding protein from pig granulocytes. J. Biol. Chem. 269:28929–28936, 1994.
22. Wu J, Rogers L, Stern D, Schmidt A M and Chiu D T W. The soluble receptor for Advanced Glycation Endproducts (sRAGE) ameliorates impaired wound healing in diabetic mice. Plastic Surgery Research Council, Abstract #77, p. 43, 1997.

Example 4

Treatment of Collagen-Induced Arthritis as an Example of Treating Inflammation

Rage (G82S) and Rheumatoid Arthritis: Increased Susceptibility and Upregulation of the Inflammatory Response Receptor for Advanced Glycation Endproducts (RAGE) and its proinflammatory S100/calgranulin ligands (1) are enriched in joints of patients with rheumatoid arthritis (RA) (2–4). Linkage disequilibrium with an RA-associated HLA-DR4 haplotype (5–6), and a polymorphism of the RAGE gene (G82S) (7–9), suggested a role for RAGE in RA. We demonstrate here that the prevalence of RAGE (G82S) is significantly increased in RA compared with controls, even in DR4-negative subjects. Cells bearing mutant RAGE (82S), either stably-transfected CHO cells or patient-derived mononuclear phagocytes, display enhanced responses following engagement of a prototypic S100/calgranulin, compared with cells expressing wild-type RAGE. Blockade of RAGE in a collagen-induced arthritis model (10–12) suppressed clinical and histologic evidence of arthritis, in parallel with diminished levels of proinflammatory mediators and markers of tissue degradation. These findings associate RAGE (G82S) with increased susceptibility to RA, and suggest that RAGE (G82S) primes joint tissue for enhanced inflammation and destruction in evolving arthritis.

MHC-linked genes are widely accepted contributors to susceptibility in autoimmune/inflammatory disorders, though the identity of these genes has yet to be fully elucidated. Indeed, it is highly likely that multiple genes within the MHC, and, perhaps, outside this complex, are involved in human autoimmunity. Specifically, in rheumatoid arthritis (RA), polymorphisms at the HLA-DRB1 locus, particularly within the DRB1*04 and DRB1*01 groups of alleles, have been most strongly associated with development of disease (5–6, 13). However, despite intense investigation, a definitive understanding of the link between these alleles and their involvement in susceptibility and/or evolution of proinflammatory phenomena in RA has not been achieved. The gene encoding RAGE, a multi-ligand member of the immunoglobulin superfamily of cell surface molecules, is located approximately 400 kb from HLA-DRB1 and 300 kb from HLA-DRA, near the junction of MHC Class II and Class III (7). Furthermore, expression of RAGE and its proinflammatory ligands of the S100/calgranulin family (termed EN-RAGEs or Extracellular, Newly-identified RAGE binding proteins) (1) is enhanced in affected rheumatoid synovial tissue (2–4). These considerations led us to test whether the RAGE polymorphism (G82S), predictably increasing hydrophilicity of a critical portion of the receptor's extracellular domain involved in ligand binding, might confer increased susceptibility to RA, as well as enhanced generation of proinflammatory and tissue destructive mediators important in the evolution of arthritis.

Genomic DNA from RA patients and controls was analyzed using PCR amplification of RAGE exon 3 followed by digestion of the product with Alu I in order to identify subjects bearing the GG, GS and SS genotypes (FIG. 10). Among Caucasian subjects, 76/345 (22%) of patients with RA carried the S allele, compared with 10/190 (5.3%) control subjects, thus yielding a highly-significant association of RAGE (G82S) with RA, with an estimated relative risk (RR) of 5.0 (95% confidence interval [CI] 2.5–10.0), and p<0.001 (Table 2). Since the (G82S) polymorphism has recently been found to be in linkage disequilibrium with a common RA-associated haplotype (9), DRB*0401-DQA1*0301-DQB1*0301, it is difficult to definitively establish whether RAGE itself contributes to disease risk in the context of this haplotype. Therefore, we focussed on the subset of patients and controls who do not carry HLA-DR4 haplotypes. As shown in Table 2, when only DR4 negative subjects are considered, the RAGE (G82S) allele continues to exhibit a significant association with RA, which an estimated RR=5.9, (95% CI 1.3–28), and p=0.011. These observations indicate that presence of the RAGE G82S allele confers enhanced susceptibility to RA, even in DR4 negative subjects. Interestingly, no evidence of linkage disequilibrium between RAGE (G82S) and DRB1*0101 was seen.

RA joints display high levels of S100/calgranulins, a family of polypeptides associated with inflammatory processes, which transduce their signal of cellular activation via RAGE. To move from genetic associations to changes in cell function associated with inflammatory pathways underlying RA, we investigated whether RAGE (G82S) would display altered affinity and activation of signal transduction pathways, compared with the wild-type receptor, when exposed to a prototypic S100/calgranulin that we previously termed EN-RAGE (1). Chinese hamster ovary (CHO) cells provide a convenient model, as they are devoid of detectable RAGE prior to, or after stable transfection with pcDNA3.1 vector alone (FIG. 11A). Stably-transfected CHO cells were made with pcDNA3.1 containing either wild-type RAGE or mutant RAGE (82S) (FIG. 11A). Radioligand binding studies showed dose-dependent binding of $^{125}$I-EN-RAGE to CHO cells expressing wild-type ($\approx$122±31 nM) and mutant receptor (Kd$\approx$77±21 nM), though the affinity of binding was greater with the mutant receptor (FIG. 2b; p=0.008). In contrast, CHO cells stably transfected with the empty vector (mock) displayed no specific binding of $^{125}$-I-EN-RAGE (FIG. 11B). That the interaction of RAGE-bearing CHO cells with $^{125}$I-EN-RAGE was specific for interaction with RAGE was shown by inhibition of specific binding in the presence of an excess of soluble extracellular domain of the receptor (sRAGE), or anti-RAGE IgG (FIG. 11C). In contrast, addition of bovine serum albumin (BSA) or nonimmune IgG was without effect.

These observations led us to test the concept that engagement of RAGE (82S) on transfected CHO cells by EN-RAGE might amplify cellular activation beyond that seen in cells bearing wild-type RAGE. Incubation of mock-transfected CHO cells with EN-RAGE (10 µg/ml) did not increase intensity of the bands corresponding to phosphorylated p44/42 MAP kinases (14–15) (FIG. 11D, lanes 1–5). However, exposure of wild-type RAGE CHO transfectants to EN-RAGE increased by ≈2-fold phosphorylated p44/42 MAP kinases, compared with cultures incubated with BSA alone (FIG. 11D, lanes 7 & 6, respectively; p<0.01). CHO transfectants bearing RAGE (82S) incubated with EN-RAGE displayed ≈3.9-fold increase in phosphorylated p44/42 compared with BSA (FIG. 11D, lanes 12 & 11, respectively; p<0.01). Compared with cells expressing wild-type RAGE, CHO cells expressing mutant RAGE displayed significantly increased phosphorylation of p44/p42 MAP kinases (FIG. 11D, lanes 12 & 7, respectively; p<0.05). In both wild-type RAGE- and mutant RAGE-transfected cells, cellular activation by EN-RAGE was due to engagement of RAGE as demonstrated by suppression of phosphorylation of p44/p42 in the presence of excess sRAGE (FIG. 11D, lanes 8 & 13, respectively), or anti-RAGE IgG (FIG. 11D, lanes 9 & 14, respectively). Nonimmune IgG was without effect (FIG. 11D, lanes 10 & 15, respectively). In all cases, levels of nonphosphorylated p44/p42 MAP kinases were identical.

To further support the hypothesis that the presence of mutant RAGE (82S) enhanced activation of key proinflammatory signal transduction pathways, we assessed nuclear translocation of NF-kB in CHO transfectants exposed to EN-RAGE. Electrophoretic mobility shift assays (EMSA) using $^{32}$P-labelled consensus NF-κB probe and nuclear extracts from mock-transfected CHO cells showed no increase in intensity of the gel shift band after cultures were exposed to EN-RAGE (FIG. 11E, lane 2). When these experiments were repeated with CHO transfectants expressing wild-type RAGE, there was a prominent ≈5.4-fold increase in intensity in nuclear binding activity following incubation of cultures with EN-RAGE compared to BSA (FIG. 11E, lanes 7 & 6, respectively). NF-κB activation was even more striking when RAGE (82S) was substituted for wild-type RAGE; RAGE (82S) CHO transfectants displayed ≈11.3-fold increased intensity of the gel shift band consequent to the presence of EN-RAGE, compared to incubation with BSA (FIG. 11E, lanes 12 & 11, respectively). Thus, RAGE-mediated NF-κB activation due to EN-RAGE was enhanced by ≈2.1-fold comparing mutant to wild-type receptor. That activation of NF-κB in transfected CHO cells by EN-RAGE resulted from ligation of wild-type or mutant RAGE was confirmed by its inhibition in the presence of sRAGE (FIG. 11E, lanes 8&13, respectively), or anti-RAGE IgG (FIG. 11E, lanes 9 & 14, respectively). Incubation with nonimmune IgG had no effect (FIG. 11E, lanes 10 & 15, respectively).

A critical test of these concepts was whether mononuclear phagocytes (MPs) retrieved from human subjects bearing a mutant RAGE allele displayed enhanced activation and generation of proinflammatory mediators in the presence of EN-RAGE. Immunoblotting revealed that basal levels of RAGE did not differ between MPs bearing wild-type (G82G), (G82S) or (S82S) alleles. Signaling was compared in MPs from patients with RAGE (G82G) and RAGE (G82S)/(S82S) by assessing activation of p44/p42 MAP kinases. In the presence of EN-RAGE, MPs isolated from individuals bearing mutant RAGE displayed an ≈4.8-fold increase in phosphorylated p44 and p42 MAP kinases compared with unstimulated cells (FIGS. 12A&B). However, MPs bearing wild-type RAGE exposed to EN-RAGE revealed a significant, although smaller (≈2.2-fold) increase in activation of p44/p42 MAP kinases (FIGS. 12A & B). The differences between EN-RAGE-mediated activation of p44/p42 MAP kinases in mutant vs. wild-type RAGE-expressing MPs were significant, p<0.05 (FIG. 12B).

In order to assess the functional consequences of enhanced activation of signal transduction molecules stimulated upon ligation of RAGE, we examined production of key inflammatory and tissue-degradative mediators linked to RA (16–19) by MPs bearing wild-type RAGE or the mutant allele. Exposure of wild-type RAGE-bearing MPs to EN-RAGE caused an ≈4-fold increase in generation of TNF-alpha detected in culture supernatant compared with quiescent cultures (322±51 vs 81±8.3 ng/ml; p<0.001) (FIG. 12C). However, upon incubation of human MPs bearing GS or SS RAGE, an ≈17.8-fold increase in elaborated TNF-alpha was observed in culture supernatants compared to basal levels (1,623±98 vs 91±11.1 ng/ml; p<0.001) (FIG. 12C) Importantly, although basal levels of TNF-alpha did not differ between wild-type RAGE- and mutant RAGE-bearing MPs, levels of TNF-alpha were ≈4.5-fold more in the presence of RAGE (G82S)/(S82S) compared with wild-type RAGE, p<0.01 (FIG. 12C). Similarly, wild-type RAGE-bearing MPs exposed to EN-RAGE displayed a small, but significant ≈1.5-fold increase in generation of IL-6 compared with basal expression (29.2±4.1 vs 20.2±3.2 ng/ml; p<0.05) (FIG. 12D). However, MPs bearing GS or SS revealed an Å10.9-fold augmented generation of IL-6 upon incubation with EN-RAGE compared with unstimulated controls (229.3±26.8 vs 21±1.8 ng/ml; p<0.001) (FIG. 12D). Again, MPs bearing mutant RAGE generated increased amounts of IL-6 compared with cells from wild-type individuals (≈7.3-fold; p<0.01) (FIG. 12D). In these studies, no significant differences between cellular activation induced by EN-RAGE in MPs bearing (G82S) or (S82S) RAGE were observed.

A central means by which structural elements of joints, such as cartilage and bone, are degraded in unchecked RA is by generation of matrix metalloproteinases (MMP), such as MMP-9. We hypothesized that RAGE-mediated MP activation would augment generation of MMP-9 activity on cells bearing mutant receptor (G82S, S82S) versus those expressing wild-type RAGE. MPs retrieved from subjects bearing wild-type RAGE displayed an ≈2.3-fold increase in MMP-9 activity in the presence of EN-RAGE compared with basal expression (p<0.01; FIGS. 12E & F). However, MPs isolated from individuals bearing RAGE (G82S)/(S82S) demonstrated an ≈4.7-fold increase in EN-RAGE-mediated MMP-9 activity compared with basal levels of expression, p<0.01. Although basal levels of MMP-9 activity did not differ among GG- or GS/SS-bearing MPs, the extent of EN-RAGE-mediated enhanced MMP-9 activity was significantly enhanced, ≈2-fold, in MPs bearing mutant RAGE allele vs. wild-type receptor (p<0.01; FIGS. 12E & F).

These findings strongly suggest that in human subjects, the presence of the 82S allele contributes, at least in part, to enhanced susceptibility to RA, as well as to EN-RAGE-mediated increased expression of proinflammatory and tissue-destructive mediators highly-prevalent in rheumatoid synovium. To determine if the interaction of EN-RAGE with RAGE modulated joint inflammation and destruction in vivo, we employed a murine model of polyarticular inflammatory arthritis induced by sensitization and challenge with bovine type II collagen (10–12), the predominant protein of articular cartilage, in dba/1 mice. Bovine type II collagen was emulsified in incomplete Freund's adjuvant and injected intradermally at the base of the tail (time 0; immunization). Three weeks later, mice were challenged with a second intradermal injection of bovine collagen type II/incomplete Freund's adjuvant (time 3 weeks; challenge). The contribution of RAGE to the pathogenesis of arthritis was studied by treating animals with sRAGE (20). The administered exogenous sRAGE functions as a decoy by engaging RAGE ligands and preventing their access to cell surface receptor. Treatment with sRAGE, 100 μg/day, was started at three weeks (time of challenge with bovine type II collagen). In previous studies, blockade of RAGE at this dose affected the greatest decrease in the proinflammatory phenotype in a murine model of delayed-type hypersensitivity (1).

The relevance of RAGE-ligand interaction in collagen-induced arthritis was underscored by the increased expression of RAGE and EN-RAGE in joint tissues. At six weeks, compared with control mice, joint tissue from the hindpaw of mice immunized/challenged with type II collagen demonstrated hypertrophy and hyperplasia of synovial cells (FIGS. 13A & B, respectively). RAGE and EN-RAGE expression was increased in joint tissue from mice with arthritis compared with controls (RAGE, FIGS. 13C & D; EN-RAGE, FIGS. 13E & F, respectively). Immunoblots of joint tissue from control animals and those with arthritis to detect RAGE and EN-RAGEs showed increased expression in each case. RAGE levels were enhanced ≈2.2-fold ($p<0.001$) in arthritis versus control joints (FIG. 13I). Although EN-RAGEs were not detectable in joint tissue of control mice, expression of these proinflammatory mediators was induced in vehicle (murine serum albumin [MSA])-treated mice immunized/challenged with bovine type II collagen (FIG. 13J). In mice treated with sRAGE, levels of RAGE and EN-RAGE antigen by immunoblotting were significantly reduced compared to mice treated with MSA (FIG. 13I & J, respectively).

Consistent with the observation that blockade of RAGE in this model of inflammatory arthritis reduced expression of RAGE and accumulation/expression of proinflammatory EN-RAGEs, mice treated with sRAGE displayed little evidence of foot pad swelling/thickening in contrast to prominent swelling observed in MSA-treated mice evaluated at multiple time points between 3.5–8 weeks after immunization; $p<0.001$ (FIG. 14A). Similarly, clinical scoring of inflammatory arthritis at the wrist joint of immunized/challenged mice revealed a significant reduction in mice treated with sRAGE versus MSA ($p=0.001$; FIG. 14B).

In order to dissect the molecular mechanisms underlying the apparent protection afforded by preventing ligands from engaging cell surface RAGE by administration of sRAGE, we assessed plasma and joint tissue markers of inflammation. Immunoblots revealed undetectable TNF-alpha in joint tissue of control mice, whereas a striking induction was observed in MSA-treated mice immunized/challenged with bovine type II collagen (FIG. 14C). Animals subjected to the arthritis protocol and treated with sRAGE showed striking reduction in TNF-alpha (≈25.7-fold; $p=0.001$). Similarly, plasma TNF-alpha antigen, although undetectable in control mice, was markedly induced in plasma retrieved from mice immunized/challenged mice with type II collagen and treated with MSA (FIG. 14D). Plasma TNF-alpha was suppressed ≈2.4-fold in samples from mice treated with sRAGE (46±6.2 vs 19±1.2 ng/ml, respectively; $p=0.03$). IL-6 antigen in joint tissue increased in MSA-treated mice immunized/challenged with type II collagen compared with those animals receiving sRAGE (1,260±465 vs 478±153 ng/μg tissue; $p=0.04$) (FIG. 14E). No measurable levels of IL-6 were detected in tissue retrieved from control mice. Similarly, levels of IL-2 were reduced in joint tissue of mice treated with sRAGE (FIG. 14F).

As induction of TNF-alpha and other inflammatory cytokines sets in motion events leading to activation of latent/proenzyme MMPs (21), we assessed MMP antigen and activity in stifle joint tissue retrieved from the mice employed in this model. Compared with control joint tissue, that retrieved from MSA-treated mice undergoing the collagen-induced arthritis protocol revealed ≈2.4-fold increase in MMP-2 antigen by immunoblotting ($p=0.01$; FIG. 15A). That activation of RAGE was critical in this process was demonstrated by the significant reduction in MMP-2 expression in joint tissue of sRAGE-treated mice, to levels observed in unaffected mice ($p=0.02$; FIG. 15A). In addition, expression of MMP-9 antigen was increased ≈4.6-fold in joint tissue retrieved from MSA-treated mice compared with animals without arthritis ($p=0.01$; FIG. 15B). Levels of MMP-9 antigen were significantly reduced in mice receiving sRAGE compared with those mice receiving MSA; $p=0.02$ (FIG. 15B). In order to determine the extent of activity of MMPs 2 and 9 in the joint tissue, we performed zymography. Consistent with increased levels of MMP-2 and MMP-9 antigen in mice with arthritis, an ≈11.6- and ≈5.5-fold increase in activity of MMP-2 and MMP-9, respectively, was observed in joint tissue from vehicle, MSA-treated mice compared with unafffected mice; $p=0.001$ and $p=0.02$, respectively (FIG. 15C–D). In the presence of sRAGE, levels of MMP-2 and MMP-9 activity were reduced by ≈2.2- and 4.2-fold, respectively, compared with mice receiving MSA; $p=0.004$ and $p=0.005$, respectively (FIG. 15C–D).

Lastly, in order to determine if blockade of RAGE suppressed immune/inflammatory responses to bovine type II collagen at extra-articular sites, at 6 weeks after immunization, immediately prior to sacrifice, mice receiving either MSA or sRAGE were injected with bovine type II collagen (10 μg) into ear tissue. Although baseline ear thickness was essentially identical in both groups of mice, 18 hrs after injection, mice receiving MSA revealed an ≈2.1-fold increase in ear thickness compared with those mice injected with sRAGE ($p=0.03$; FIG. 16A). Consistent with these observations, splenocytes retrieved from MSA-treated mice at six weeks revealed significantly increased proliferation, as measured by incorporation of tritiated thymidine, upon stimulation with bovine type II collagen compared with mice treated with sRAGE; $p=0.003$ (FIG. 16B). However, no significant differences in basal levels of proliferation, or proliferation in the presence of PMA, were observed between mice treated MSA vs sRAGE (FIG. 16B).

The S100/calgranulin family of proinflammatory molecules, long-associated with classic immune/inflammatory disorders (22–23), has been mechanistically linked to cellular activation resulting in an inflammatory phenotype by the observation that these molecules are signal-transducing ligands of RAGE. Their release by activated inflammatory effector cells, and accumulation in synovial fluid and plasma of patients with RA has been linked to indices of disease severity (4), such as bony erosions. In this context, Czech subjects with psoriasis vulgaris, an immune/inflammatory disease of the skin, displayed enrichment for the RAGE (G82S) allele compared with age-matched subjects without this skin disorder (24). Furthermore, strongly increased expression of a member of the S100 family of proinflammatory molecules, "psoriasin", has been demonstrated in psoriatic lesions compared with adjacent unaffected skin (25). These observations further support the premise that S100/calgranulin-RAGE interaction may provide a mechanism contributing to immune/inflammatory disorders. Finally, the data presented herein suggests the possibility that the RAGE (G82S) allele might prime affected tissues for exaggerated inflammatory processes.

Previous studies demonstrated that the ligands of RAGE identified thus far, each effectively cross-compete in radioligand binding assays (1). These ligands include EN-RAGE (S100A12) and related members of the S100/calgranulin family of proinflammatory cytokines (1); Advanced Glycation Endproducts (AGEs) and, particularly, carboxy(methyl lysine) (CML) adducts of proteins and lipids (26–27); amyloid-β peptide (28); and amphoterin (15,29). Our studies support the contention that the primary binding site for each of these ligands is within the V-domain (27), the same region in which the (G82S) substitution occurs. Indeed, substitution of glycine with serine at this site is likely to alter polarity within that region. Consistent with this concept, we demonstrated enhanced affinity and cellular activation mediated by one of the receptor's ligands, EN-RAGE, on interaction with mutant RAGE (82S) compared with wild-type RAGE. Although studies to identify and characterize the tertiary structure of RAGE are underway, it is nevertheless certain that altered properties of ligand engagement ensue in the face of this polymorphism.

The present studies have demonstrated an association between the (G82S) RAGE polymorphism and susceptibility to RA, including those without an HLA-DR4 allele, thus providing critical evidence that our findings do not solely reflect the known linkage disequilibrium between this polymorphism and HLA-DRB1*04 haplotypes. In the future, a detailed haplotypic analysis of the MHC (30) may provide further evidence of genetic heterogeneity underlying MHC-linked susceptibility to RA. Studies are ongoing to define the precise molecular cues triggered by this polymorphism that appear to augur enhanced susceptibility to, and, possibly, accelerated evolution of proinflammatory and tissue-degradative properties in rheumatoid synovium. Certainly, improved understanding of these complex relationships may refine not only diagnostic criteria, but, ultimately, optimal means of therapeutic intervention in this perplexing class of human disorders.

Experimental Methods

Patient population. The rheumatoid arthritis patients used for association studies meet the criteria of the American College of Rheumatology (31) and were taken from patient populations (32) collected by the North America Rheumatoid Arthritis Consortium and the Arthritis Research Center in Wichita, Kansas.

Detection of Gly82Ser polymorphism. The following primers were synthesized for detection of the glycine82serine (G82S) polymorphism of the RAGE gene (8): sense primer: 5' GTAAGCGGGGCTCCTGTTGCA-3' (SEQ ID NO:13) and the antisense primer: 5'GGCCAAG-GCTGGGGTTGAAGG-3' (SEQ ID NO:14). Whole blood (20 /µl) was obtained from human volunteers in accordance with the standards and policies of the Institutional Review Boards of the participating institutions. Genomic DNA was prepared according to the manufacturer's instructions using a kit from QIAGEN™ (Valencia, Calif.); 10 ng was amplified using Taq I polymerase (Life Technologies, Grand Island, N.Y.) in a final volume of 25 µl. PCR conditions were as follows: 94° C. for 30 secs, 62° C. for 45 secs, and 72° C. for 60 secs for a total of 35 cycles. PCR product (25 µl) was then digested with Alu 1 (Life Technologies), 3 U for 16 hrs at 37° C., followed by gel electrophoresis on agarose gels (2%).

Chinese Hamster Ovary (CHO) cell studies. Chinese hamster ovary (CHO) cells were obtained from the American Type Culture Collection (ATCC) (Manassas, Va.) and cultured in F12 medium containing fetal bovine serum (10%) (Life Technologies). In order to generate the mutant 82S allele, the cDNA encoding human RAGE33 was cloned using the TOPO TA™ cloning system into pCR2.1TOPO vector for mutagenesis (Invitrogen, Carlsbad, Calif.). Site-directed mutagenesis to insert the (Gly82) (wild-type) to (Ser82) (mutant) change was performed using the GENE-EDITOR™ In Vitro SDM System (Promega, Madison, Wis.) according to the manufacturer's instructions. Sequencing was performed using an ABI310 automated DNA sequencer (Perkin Elmer Biosystems, Foster City, Calif.) to confirm the inserted sequence changes and to ensure that no other mutations were created during any of the mutagenesis reactions. Both wild-type and mutant RAGE cDNA were excised from pCR2.1TOPO using EcoR I and subcloned into the pcDNA3.1 expression vector (Invitrogen). Cells were transfected with plasmid DNA using lipofectamine (Life Technologies) encoding the following: pcDNA3.1 containing full-length wild-type RAGE cDNA (Gly82), pcDNA3.1 containing mutant RAGE cDNA (Ser82) or pcDNA3.1 containing no insert (mock-transfectant). 24 hrs after transfection, selection was begun using G418 (1 mg/ml) (Life Technologies). RAGE expression was assessed by immonoblotting in stably-transfected cells after 6 weeks. Cells were incubated with the indicated mediators (BSA or EN-RAGE1) and assessed for activation of phosphorylated p44/p42 MAP kinase, or for nuclear translocation of NF-kB.

Radioligand binding assays. Purified EN-RAGE was radiolabelled using $^{125}$-I and Iodobeads (Pierce, Arlington Heights, Ill.) to a specific activity of approximately 5,000 cpm/ng. Radioligand binding assays were performed in 96-well tissue culture dishes containing the indicated transfected CHO cells. A radioligand binding assay was performed in the presence of the indicated concentration of radiolabelled EN-RAGE±an 50-fold molar excess of unlabelled EN-RAGE in PBS containing calcium/magnesium and BSA, 0.2%, for 3 hrs at 37¡ C. Wells were washed rapidly with washing buffer (PBS containing Tween 20 (0.05%)). Elution of bound material was performed in a solution containing heparin, 1 mg/ml. Solution was aspirated from the wells and counted in a gamma counter (LKB, Gaithersburg, Md). Equilibrium binding data were analyzed according to the equation of Klotz and Hunston (34): B=nKA/1+KA, where B=specifically bound ligand (total binding, wells incubated with tracer alone, minus nonspecific binding, wells incubated with tracer in the presence of excess unlabeled material), n=sites/cell, K=the dissociation constant, and A=free ligand concentration) using nonlinear least-squares analysis (Prism; San Diego, Calif.). Where indicated, pretreatment with either antibodies, or human soluble RAGE, was performed.

Activation of p44/p42 MAP kinases. CHO cells were incubated with EN-PAGE, 10 µg/ml, for one hr. Cells were lysed in lysis buffer (New England Biolabs, Beverly, Mass.). Cell lysate was subjected to centrifugation and protein concentration of the supernatant determined using the Bio-Rad assay (Bio-Rad, Hercules, Calif.). Equal amounts of protein were subjected to SDS-PAGE (Novex/Invitrogen, Carlsbad, Calif.). Contents of the gels were transferred to nitrocellulose and immunblotting performed using anti-phosphorylated p44/p42 MAP kinase (New England Biolabs). Bands were scanned into a densitometer, and band density was quantified using IMAGEQUANT™ (Molecular Dynamics, Foster City, Calif.).

Electrophoretic mobility shift assay. Nuclear extracts were prepared and EMSA performed employing consensus $^{32}$P-labeled probe for NF-kB as described (1). Where indicated, cells were treated with either nonimmune/anti-RAGE F(ab')2, or soluble RAGE, as described (1,20).

Peripheral Blood-derived Mononuclear Phagocyte (MPs) Studies

Cellular isolation. Whole venous blood was obtained from healthy volunteers (30 ml) bearing G82G, G82S, and S82S RAGE. Mononuclear cells were isolated using Histopaque 1077 (Sigma, St. Louis, Mo.) and cultured on plastic dishes for 3 hrs at 37¡ C. Nonadherent cells were removed by washing in phosphate buffered saline (PBS). Adherent cells (MPs) were removed by incubation with EDTA (2 mM) for 15 mins at 37° C. Cells were seeded in tissue-cultured coated wells for study.

Activation of p44/p42 MAP kinases. MPs were seeded into the wells of 24-well tissue culture plates at a density of $5\times10^5$ cells per well. Cells were stimulated with either BSA or EN-RAGE, and immunoblotting for detection of phosphorylated p44/p42 MAP kinases performed as above.

Detection of IL-6 and TNF-alpha. MPs were seeded into the wells of 24-well tissue culture plates at a density of $5\times10^5$ cells per well. Cells were stimulated with either BSA or EN-RAGE (10 µg/ml). Supernatant was assayed for IL-6 and TNF-alpha using ELISA kits from R&D systems (Minneapolis, Minn.) according to the manufacturer's instructions.

Murine studies: induction of bovine collagen type II-induced arthritis. Male dba/1 mice were purchased from the Jackson Laboratories (Bar Harbor, Me.). Mice weighing 20–30 gms were injected intradermally at the base of the tail with bovine type II collagen, 200 µg (Sigma) dissolved in acetic acid (0.10M) and emulsified in incomplete Freund's adjuvant (Sigma). Three weeks after sensitization, mice were challenged by injection of bovine collagen type II (200 µg) as above in incomplete Freund's adjuvant at the base of the tail. Beginning at three weeks after immunization (at the time of challenge), mice were treated with either murine soluble RAGE (20), or vehicle, murine serum albumin (Sigma), both at 100 µg per day by intraperitoneal injection. Treatment was continued daily until sacrifice.

Assessment of arthritis. Evidence of arthritis was evaluated at the indicated time points after initial immunization by an observer blinded to the experimental conditions. Severity of arthritis in the wrist joints was assessed according to the following scale: 0=no redness or swelling; 1=slight/moderate redness and swelling; and 2=severe redness and swelling. At the same time points, extent of swelling in the distal footpads was assessed by measurement of foot pad diameter using calipers. In each case, the mean of score/footpad diameter was obtained and reported.

Injection of bovine collagen II into the ear. Six weeks after initial sensitization, bovine type II collagen (10 µg) was injected into the ear of each mouse. 18 hrs later, thickness of the ear was assessed using calipers by an observer blinded to the experimental conditions.

Retrieval of tissues at sacrifice. Mice were sacrificed 3 or 6 weeks after challenge. The stifle joint was removed and homogenized in Tris-buffered saline containing protease inhibitors (Complete Protease Inhibitor, Boehringer-Mannheim, Indianapolis, Ind.). From each animal, joints from the wrist and foot paw were fixed in formalin (10%) for 16 hrs followed by storage in PBS for studies using hematoxylin and eosin (H&E) or the indicated antibodies.

Assessment of splenocyte proliferation. Spleens were removed at sacrifice and meshed in RPMI medium (Life Technologies) and diluted in 10 ml of the same medium. The solution was subjected to centrifugation at 1,200 rpm at 4° C. for 10 mins. The pellet was dissolved in RPMI medium (15 ml) and aliquoted. Bovine type II collagen, or PMA, (0.1 µg/ml in each case) was added for 24 hrs. Tritiated thymidine (0.02 ml) was then added for an additional 18 hrs. Cells were retrieved and counted in a beta counter (LKB).

Assessment of plasma TNF-alpha. Upon sacrifice, plasma was obtained and assessed by ELISA for levels of murine TNF-alpha using a kit from R&D Systems according to the manufacturer's instructions.

Immunoblotting and ELISA. SDS-PAGE and immunoblotting were performed on extracts of stifle joint tissue using the following antibodies: anti-RAGE IgG and anti-EN-RAGE IgG as previously described1 (4.7 and 2.0 µg/ml, respectively); anti-MMP 2 and anti-MMP 9 IgG (1 µg/ml; Chemicon (Temecula, Calif.); and anti-TNF-alpha IgG (1 µg/ml; R&D Systems). Bands were scanned into a densitometer, and band density was quantified using IMAGEQUANT™. In other experiments, assessment of joint tissue levels of IL-6 and IL-2 was performed by subjecting joint tissue lysates to ELISA using kits from R&D systems.

Zymography. Zymography for detection of MMP-2 and MMP-9 activity were determined using gelatin-laden gels from Novex/Invitrogen according to the manufacturer instructions.

Bands were scanned into a densitometer, and band density was quantified as above.

Statistical analysis. Statistical comparisons among groups were determined using one-way analysis of variance (ANOVA); where indicated, individual comparisons were performed using students' t-test.

REFERENCES FOR EXAMPLE 4

1. Hofmann, M. A., et al. RAGE mediates a novel proinflammatory axis: a central cell surface receptor for S100/calgranulin polypeptides. Cell 97, 889–901 (1999).
2. Chilosi, M., et al. Multimarker immunohistochemical staining of calgranulin, chloroacetate esterase, and S100 for simultaneous demonstration of inflammatory cells on paraffin sections. J. Histochem. Cytochem. 38, 1669–1675 (1990).
3. Youssef, P., et al. Expression of myeloid related proteins (MRP) 8 and 14 and the MRP8/14 heterodimer in rheumatoid arthritis synovial membrane. J. Rheumatol. 26, 2523–2528 (1999).
4. Frosch, M., et al. Myeloid-related proteins 8 and 14 are specifically secreted during interaction of phagocytes and activated endothelium and are useful markers for monitoring disease activity in pauciarticular-onset juvenile rheumatoid arthritis. Arthritis Rheum. 43, 628–637 (2000).
5. Gregersen, P. K., Silver, J., and Winchester, R. J. The shared epitope hypothesis. An approach to understanding the molecular genetics of susceptibility to rheumatoid arthritis. Arthritis Rheum. 30, 1205–1213 (1987).
6. Stastny, P. Association of the B-cell autoantigen DRW4 with rheumatoid arthritis. N. Engl. J. Med. 298, 869–871 (1978).
7. Sugaya, K., et al. Three genes in the MHC Class III region near the junction with the class II: gene for Receptor of Advanced Glycosylation End Products, PBX2 homeobox gene and a notch homolog, human counterpart of mouse mammary tumor gene int-3. Genomics 23, 408–419 (1994).

8. Hudson, B. I., Strickland, M. H., and Grant, P. J. Identification of polymorphisms in the Receptor for Advanced Glycation End Products (RAGE) gene. Diabetes 47, 1155–1157.
9. Prevost, G., Fajardy, I., Fontaine, P., Danze, P. M., and Besmond, C. Human RAGE Gly82Ser dimorphism and HLA class II DRB1-DqA1-DQB1 haplotypes in type 1 diabetes. European J. Immunogenetics 28, 343–348 (1999).
10. Courtenay, J. S, Dallman, M. J., Dayan, A. D., Martin, A., and Mosedale, B. Immunization against heterologous type II collagen induces arthritis in mice. Nature 283, 666–668 (1980).
11. Trentham, D. E., Townes, A. S., and Kang, A. H. Autoimmunity to type II collagen an experimental model of arthritis. J. Exp. Med. 146, 857–868 (1977).
12. Cathcart, E. S., Hayes, K. C., Gonnerman, W. A., Lazzari, A. A., and Franzblau, C. Experimental arthritis in a nonhuman primate. I. Induction by bovine type II collagen. Lab. Invest. 54, 26–31 (1986).
13. Schiff, B., Mizrachi, Y., Orgad, S., Yaron, M., and Gazit, I. Association of HLA-Aw31 and HLA-DR1 with adult rheumatoid arthritis. Ann. Rheum. Dis. 41, 403–406 (1991).
14. Lander, H. L., Tauras, J. M., Ogiste, J. S., Moss, R. A., and A. M. Schmidt. Activation of the Receptor for Advanced Glycation Endproducts triggers a MAP Kinase pathway regulated by oxidant stress. J. Biol. Chem. 272,17810–17814 (1997).
15. Taguchi, A., et al. Blockade of amphoterin/RAGE signalling suppresses tumor growth and metastases. Nature 405, 354–360 (2000).
16. Pisetsky, D. S. Tumor necrosis factor blockers in rheumatoid arthritis. N. Engl. J. Med. 342, 810–811 (2000).
17. Boe, A., Baiocchi, M., Carbonatto, M., Papoian, R., and Serlupi-Crescenzi, O. Interleukin-6 knock-out mice are resistant to antigen-induced experimental arthritis. Cytokine 11, 1057–1064 (1999).
18. Robak, T., Gladalska, A., Stepien, H., and Robak, E. Serum levels of interleukin-6 type cytokines and soluble interleukin-6 receptor in patients with rheumatoid arthritis. Mediators Inflamm. 7, 347–353 (1998).
19. Keyszer, G., et al. Circulating levels of matrix metalloproteinases MMP-3 and MMP-1, tissue inhibitor of metalloproteinases 1 (TIMP-1), and MMP-1/TIMP-1 complex in rheumatic disease. Correlation with clinical activity of rheumatoid arthritis versus other surrogate markers. J. Rheumatol. 26, 251–258 (1999).
20. Park, L., et al. Suppression of accelerated diabetic atherosclerosis by soluble Receptor for AGE (sRAGE). Nature Medicine 4,1025–1031 (1998).
21. Pugin, J., et al. Human neutrophils secrete gelatinase B in vitro and in vivo in response to endotoxin and proinflammatory mediators. Am. J. Respir. Cell. Mol. Biol. 20, 458–464 (1999).
22. Zimmer, D. B., Cornwall, E. H., Landar, A., and Song, W. The S100 protein family: history, function, and expression. Brain Research Bulletin 37, 417–429 (1995).
23. Schafer, B. W., and Heinzmann, C. W. The S100 family of EF-hand calcium-binding proteins: functions and pathology. TIBS 21, 134–140 (1996).
24. Kankova, K., Vasku, A., Hajek, D., Zahejsky, J., and Vasku, V. Association of G82S polymorphism in the RAGE gene with skin complications in type 2 diabetes. Diabetes Care 22, 1745 (1999).
25. Madsen, P. Molecular cloning, occurrence and expression of a novel partially secreted protein ÒpsoriasinÓ that is highly up-regulated in psoriatic skin. J. Invest. Dermatol. 97, 701–712 (1991).
26. Schmidt, A. M., et al. Isolation and characterization of binding proteins for advanced glycosylation endproducts from lung tissue which are present on the endothelial cell surface. J. Biol. Chem. 267, 14987–14997 (1992).
27. Kislinger, T., et al. Ne (carboxymethyl)lysine modifications of proteins are ligands for RAGE that activate cell signalling pathways and modulate gene expression. J. Biol. Chemistry 274, 31740–31749 (1999).
28. Yan, S. D., et al. RAGE and amyloid beta peptide neurotoxicity in AlzheimerÕs disease. Nature 382, 685–691 (1996).
29. Hori, O., et al. The receptor for advanced glycation endproducts (RAGE) is a cellular binding site for amphoterin: mediation of neurite outgrowth and coexpression of RAGE and amphoterin in the developing nervous system. J. Biol. Chem. 270, 25752–25761 (1995).
30. Nair, R. P., et al. Localization of psoriasis-susceptibility locus PSORS1 to a 60-kb interval telomeric to HLA-C. Am. J. Human Genet. 66, 1833–1844 (2000).
31. Arnett, F. C., et al. The American Rheumatism Association 1987 revised criteria for the classification of rheumatoid arthritis. Arthritis and Rheumatism 31, 315–324 (1988).
32. Seldin, M. F., Amos, C. I., Ward, R., and Gregersen, P. K. The genetics revolution and the assault on rheumatoid arthritis. Arthritis and Rheumatism 42, 1071–1079 (1999).
33. Neeper, M., et al. Cloning and expression of RAGE: a cell surface receptor for advanced glycosylation end products of proteins. J. Biol. Chem. 267, 14998–15004 (1992).
34. Klotz, I., and Hunston, D. Mathematical models for ligand-receptor binding. J. Biol. Chem. 259, 10060–10062 (1984).

TABLE 2

Prevalence of the RAGE 82S allele in patients with rheumatoid arthritis (RA) and controls.

| | RA patients | Controls | p value |
| --- | --- | --- | --- |
| All subjects | 76/345 (22%) | 10/190 (5.3%) | <0.001 |
| DR4 negative subjects | 9/114 (7.9%) | 2/141 (1.4%) | 0.011 |

Example 5

Treatment of Autoimmune Diseases as an Example of Treating Inflammation, EAE

Uses of Soluble RAGE Related to Models of Autoimmune: Experimental Autoimmune Encephalitis and Adoptive Transfer Diabetes The experiments below describe the use of soluble (s) RAGE (Receptor for advanced glycation endproducts) to inhibit the development of autoimmune (type I) diabetes in an adoptive transfer model and the occurrence of experimental autoimmune encephalitis (EAE) both in murine systems.

The adoptive transfer model of diabetes involves transfer of splenocytes from diabetic NOD (non-obese diabetic)

mice to NOD mice with severe combined immunodeficiency (scid) (1–2). The latter mice are termed NOD/scid animals, and they do not develop diabetes spontaneously. Rather, they require the presence of immunocytes capable of destroying islet cells for induction of diabetes. This model was selected for study because: 1) the kinetics of disease in this model allows for a rapid determination of efficacy; and, 2) the model is relevant to human disease, especially in the clinical settings in which future immune therapies and islet transplantation is likely to occur (1–3). These settings include: arresting the loss of β-cell function in individuals with new onset of Type 1 diabetes, prevention of diabetes in individuals at high risk for development of disease, and blockade of disease recurrence in patients with Type 1 diabetes who received islet transplants. Many immune and non-specific treatments have been found to prevent the spontaneous development of diabetes in the NOD mouse, but with very few exceptions, these approaches have not prevented disease at its late stages or recurrent disease (3). A notable exception to this general statement includes treatment with anti-CD3 monoclonal antibody that can prevent recurrent autoimmune diabetes in recipients of islet transplants. This drug is now in clinical trials.

The myelin basic protein (MBP) model of EAE is a widely accepted system for studying the pathogenesis of multiple sclerosis (4–6). Our studies have employed the B10.PL mouse strain and two means of inducing EAE: immunization with a peptide derived from MBP and transfer of an encephalitogenic T-cell clone isolated from mice previously immunized with MBP (1AE10 cells). Preparation of such encephalitogenic T-cell clones is standard in the literature and has been described (7–10). Whereas the MBP immunization model provides a situation to study early disease, including the initial phase of sensitization to MBP, the adoptive transfer model simulates a later phase. Namely, the latter is a situation in which CD4+ lymphocytes already sensitized to MBP and activated (i.e., fully capable of causing disease) are administered to an irradiated recipient mouse which has very limited capacity to resist the destructive properties of the transferred immunocytes.

Methods

RAGE-blocking reagents. Two methods were used to prevent access of RAGE ligands to the receptor. According to the first method, soluble RAGE (sRAGE) was prepared using recombinant DNA technology (11). The murine form of sRAGE was expressed in the baculovirus system and purified to homogeneity based on a single band on SDS-PAGE. This material was required to have an undetectable level of lipopolysaccharide using the Limulus amebocyte assay (Sigma) at an sRAGE concentration of 2 mg/ml. Polyclonal antibody to RAGE was prepared in rabbits, the IgG was purified and characterized as described (11). Non-immune IgG was prepared from rabbits not sensitized to a particular antigen. This material was similarly characterized for its content of lipopolysaccharide.

Adoptive transfer model of Type 1 diabetes: NOD and NOD/scid mice were purchased from Jackson Laboratories (Bar Harbor, Me.) and housed in a pathogen-free facility in the Institute for Comparative Medicine at Columbia University. Animals were monitored for development of diabetes by screening for glycosuria. Plasma glucose levels were measured in mice found to have glycosuria. Mice with diabetes (two glucose values>250 mg/dl) were sacrificed by humane euthanasia and a single cell suspension of red blood cell-depleted splenocytes was prepared. These cells were given intravenously (IV) to NOD/scid recipients ($1.5 \times 10^7$ cells/recipient). In addition, recipients were then treated with either sRAGE (100 μg/day, intraperitoneally [ip]) or mouse serum albumin. Plasma glucose levels were measured in capillary blood from tail veins. Mice with two values>250 mg/dl were considered to have diabetes.

Once diabetes was documented, the mice were sacrificed by humane euthanasia, and the pancreas was fixed in formalin and embedded in paraffin. Immunohistologic studies were then performed on histologic sections according to standard techniques (12). Antibodies employed for immunohistologic studies were rabbit anti-tumor necrosis factor-alpha (TNF-a) IgG and rabbit anti-Interleuin (IL)-1β IgG (Santa Cruz).

The protocol for these studies involved incubation of tissue sections with primary antibodies (5 μg/ml) overnight at 4° C., followed by addition of a secondary biotin-conjugated antibody (affinity purified anti-rabbit IgG; ExtrAvidin kit from Sigma). The incubation with secondary antibody was for 30 min a 37° C., and then substrate (aminoethylcarbazole; AEC) was added (all procedures were performed according to the manufacturer's instructions; Sigma). Sections were counterstained with Mayer's hematoxylin. In other cases, sections were stained with hematoxylin and eosin (H&E) according to standard procedures (12).

EAE. Induction of EAE Involved Two Model Systems:

MBP immunization. A peptide comprising the N-terminal nine amino acids of MBP (sequence: Acetylated-Ala-Ser-Gln-Arg-Lys-Pro-Ser-Gln-Arg) (SEQ ID NO:15) (13–14) was prepared in the Peptide Chemistry Core Laboratory of Columbia University using standard techniques. The peptide (100 μg/animal) was emulsified with complete Freund's adjuvant and injected subcutaneously (the total volume was 0.1 ml). Animals (B10.PL mice from Jackson Laboratory) then received two injections of pertussis toxin (total of 1 μg/mouse) intravenously (Liss Laboratories) 24 and 72 hours after inoculation with MBP peptide. Animals were then observed for about 8 weeks for the development of symptoms of EAE. Following this period, animals were sacrificed by humane euthanasia. Where indicated, mice were treated with sRAGE starting at the time of MBP injection. Scoring of symptoms was according to the following criteria (9): 0, no signs; 1, weakness of tail; 2, mild paresis of hind limbs (paraparesis); 3, severe paresis of hind limbs; 4, complete paralysis of him limbs (paraplegia) or the limbs of one side (hemiplegia); 5, death. At the time of symptoms, or as indicated, animals were sacrificed, and the spinal cord was studied histologically. Spinal cord tissue was fixed in formalin, embedded in paraffin and sections were cut for H&E staining.

Transfer of an activated encephalitogenic T-cell clone. For this model, B10.PL mice were sublethally irradiated (350 R) and were then subject to adoptive transfer of an MBP-sensitized and in vitro activated MBP-specific $CD4^+V\beta8^+$, Th1 clone termed 1AE10 ($10-15\times10^6$ cells/animal). The in vitro activation protocol involved culturing cells with MBP peptide (10 μg/ml) in the presence of antigen presenting cells (the adherent population of splenocytes from B10.PL mice; 2:1 ratio of antigen presenting cells to 1AE10 cells) for four days and addition of IL-2 (20 U/ml; Hoffmann-LaRoche) during the last 48 hrs to increase cell number. Animals received intravenous pertussis toxin 24 and 72 hrs (as above) after infusion of activated 1AE10 cells. Similar T-cell clones and their use to induce EAE in mice have been described in the literature (7–10). This T-cell clone has been termed 1AE10 cells. RAGE blockade was achieved using rabbit anti-RAGE IgG (50 μg/animal/day) administered intraperitoneally) for fifteen days. Control animals were treated identically except that nonimmune rabbit IgG was used in place of anti-RAGE IgG. Mice were observed for 4–6 weeks for the development of symptoms (as above).

Results

Adoptive transfer model of diabetes. Treatment of NOD/scid recipients of splenocytes from diabetic NOD mice demonstrated a strong protective effect of sRAGE against the development of diabetes (FIG. 17). The islet-sparing effect of sRAGE was reversible, as discontinuance of sRAGE in 4/4 mice resulted in subsequent development of diabetes in two separate experiments. The latter result suggests that diabetogenic splenocytes that had been transferred to NOD/scid recipients retained their capacity to induce β-cell destruction, but, in the presence of sRAGE, their pathogenic immune/inflammatory potential was held in abeyance.

Histology analysis of islets demonstrated a striking reduction in inflammatory infiltrates in animals treated with sRAGE compared with controls. Immune/inflammatory cells were consistently confined to the periphery of islets in sRAGE-treated animals (FIGS. 18A–B). Immunohistology showed strong expression of TNF-a and IL-1β in inflamed islets from control animals after the onset of diabetes, whereas sRAGE-treated animals displayed only low levels of these inflammatory markers constrained to the outermost periphery of islets (i.e., peri-insulitis) (FIGS. 19A–B). Both TNF-α and IL-1β have been shown to have direct toxic effects on β-cells (15), hence the reduced expression of these mediators may account, at least in part, for the protective effect observed in sRAGE-treated animals.

EAE models. The data shown in FIG. 20 demonstrate strongly symptomatic EAE in the vehicle-treated group, whereas sRAGE-treated mice showed suppression of symptoms (all mice were immunized with MBP (maltose binding protein) as described under Methods). Histologic analysis of these mice displayed scant infiltrates in the spinal cord of MBP-immunized mice treated with sRAGE (FIG. 21C; this sample was obtained on day 35 postimmunization with MBP peptide, and the mouse was asymptomatic), compared with greater evidence of inflammatory infiltrates in the MBP-immunized group receiving vehicle alone (FIG. 21B [this sample was obtained 35 days after immunization with MBP and the mouse had symptoms of full-blown EAE]; FIG. 21A shows a mouse not immunized with MBP as a control). Semiquantitation of inflammatory infiltrates was determined by counting nuclei per high power field (10 fields per slide were counted) from representative spinal cord; sections from vehicle-treated mice demonstrated a dramatic increase in nuclei coinciding with inflammatory infiltrates, whereas administration of sRAGE caused the number of nuclei/cells per high power field to remain at the level present in normal spinal cord (FIG. 21D).

To provide a model of later-stage disease, B10. PL mice were infused with 1AE10 cells. Animals developed symptoms of EAE during weeks 3–4 following cell transfer whether receiving nonimmune IgG (FIG. 22) or vehicle (saline) alone (not shown). In contrast, mice treated with anti-RAGE IgG showed strong suppression of symptomatic EAE.

Discussion

The results of these studies demonstrate that blockade of RAGE, with sRAGE (which prevents access of ligands to the receptor by acting as a soluble decoy) or anti-RAGE IgG prevents the development of disease in murine models simulating type I diabetes and multiple sclerosis (EAE). The advantage of this method is its lack of toxicity and apparent effectiveness. An important caveat is that is difficult to be certain that the results of our experiments can be directly extrapolated to successful treatment of the human conditions. A common feature of the pathologic features of each model concerns the inability of immune/inflammatory cells to reach the target tissue (pancreatic islets or spinal cord) in the presence of RAGE blockade. In the autoimmune diabetes model, this was demonstrated to be a reversible phenomenon, as stopping sRAGE resulted in the occurrence of diabetes.

REFERENCES FOR EXAMPLE 5

1. Castano, L. and G. S. Eisenbarth, Type-I diabetes: a chronic autoimmune disease of human, mouse, and rat. Annu Rev Immunol, 1990. 8: p. 647–79
2. Pakala, S. V., M. O. Kurrer, and J. D. Katz, T helper 2 (Th2) T cells induce acute pancreatitis and diabetes in immune-compromised nonobese diabetic (NOD) mice. J Exp Med, 1997. 186(2): p. 299–306.
3. Atkinson, M. A. and E. H. Leiter, The NOD mouse model of type 1 diabetes: as good as it gets? Nat Med, 1999. 5(6): p. 601–4.
4. Lafaille, J., Nagashima, K., Katsuki, M., and Tonegawa, S. High incidence of spontaneous EAE in immunodeficient anti-MBP T-cell receptor transgenic mice. Cell 78:399–408, 1994.
5. Chen, Y., Hancock., Marks, R., Gonnella, P., and Weiner H. Mechanisms of recovery from EAE: T cell deletion and immune deviation in MBP T cell receptor transgenic mice.
6. Graesser, D., Mahooti, S., and Madri, J. Distinct roles for matrix metalloproteinase-2 and alpha-4 integrin in autoimmune T-cell extravasation and residency in brain parenchyma during EAE. J. Neuroimmunol. 109:121–131, 200.
7. Cher D, Mosmann T: Two types of murine helper T cell clones. II. Delayed type hypersensitivity is mediated by Th1 clones. J Immunol 1987;138:3688–3694.
8. Mosmann T, Cherwinski H, Bond M, Giedlin M, Coffman R: Two types of murine helper T cell clones. I. Definition according to profiles of lymphokine activities and secreted proteins. J Immunol 1986;136:2348–2357
9. Zamvil S, Nelson P, Trotter J, MItchell D, Knobler R, Fritz R, Steinman L: T cell clones specific for myelin basic protein induce chronic relapsing paralysis and demyelination. Nature 1985;317:355–358
10. Raine C, Mokhtarian F, McFarlin D: Adoptively transferrred chronic relapsing EAE in the mouse: neuropathologic analysis. Lab Invest 1984;51:534–536
11. Hofmann M, Drury S, Caifeng F, Qu W, Lu Y, Avila C, Kambhan N, RAGE mediates a novel proinflammatory axis: the cell surface receptor for S100/calgranulin polypeptides. Cell 1999;97:889–901
12. Brett, J., Schmidt, A-M., Zou, Y-S., Yan, S-D., Weidman, E., Pinsky, D., Neeper, M., Przysiecki, M., Shaw, A., Migheli, A., and Stern, D. Tissue distribution of the receptor for advanced glycation endproducts (RAGE): expression in smooth muscle, cardiac myocytes, and neural tissue in addition to the vasculature. Am. J. Pathol. 143:1699–1712, 1993.
13. Tabira T: Cellular and molecular aspects of the pathomechanism and therapy of murine EAE. Crit Rev Neurobiol 1989;5:113–142

14. Raine C: Experimental allergic encephalomyelitis, in Koetsier J (ed): Handbook of Clinical Neurology. Amsterdam, Elsevier, 1985, pp 429–466

15. Rabinovitch, A., An update on cytokines in the pathogenesis of insulin-dependent diabetes mellitus. Diabetes Metab Rev, 1998. 14(2): p. 129–51.

What is claimed is:

1. A method for treating inflammation in a subject which comprises administering to the subject an agent selected from the group consisting of soluble receptor for advanced glycation endproduct (sRAGE) or anti-RAGE antibody or anti-EN-RAGE F(ab')₂ fragment in an amount which inhibits the interaction between receptor for advanced glycation endproduct (RAGE) and EN-RAGE, thereby treating inflammation in the subject.

2. The method of claim 1 wherein the subject is a mammal.

3. The method of claim 2, wherein the mammal is a human.

4. The method of claim 1, wherein the administration comprises intralesional, intraperitoneal, intramuscular or intravenous injection; infusion; liposome-mediated delivery; topical, nasal, oral, anal, ocular or otic delivery.

5. The method of claim 1, wherein the agent is administered daily.

6. The method of claim 1, wherein the amount comprises a dose of from about 200 ng/day/kg body weight to about 200,000 ng/day/kg body weight.

7. The method of claim 1, wherein the inflammation is associated with a wound in the subject.

8. The method of claim 1, wherein the inflammation is associated with periodontal disease in the subject.

9. The method of claim 1, wherein the inflammation is associated with delayed-type hypersensitivity of a subject.

10. The method of claim 1, wherein the inflammation is associated with arthritis in a subject.

11. The method of claim 10, wherein the arthritis comprises collagen-induced arthritis, rheumatoid arthritis, psoriatic arthritis, osteoarthritis, arthritis due to Behchet's Syndrome, arthritis due to Sjogren's Syndrome, or arthritis induced by lupus.

* * * * *